US010413617B2

(12) United States Patent
Lemanski et al.

(10) Patent No.: US 10,413,617 B2
(45) Date of Patent: Sep. 17, 2019

(54) CARDIAC MYOFIBRIL INDUCTION

(71) Applicant: The Texas A&M University System, College Station, TX (US)

(72) Inventors: Larry F. Lemanski, Commerce, TX (US); Ashley Arms, Kempner, TX (US); Andrei Kochegarov, Commerce, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/034,484

(22) PCT Filed: Nov. 6, 2014

(86) PCT No.: PCT/US2014/064303
§ 371 (c)(1),
(2) Date: May 4, 2016

(87) PCT Pub. No.: WO2015/069866
PCT Pub. Date: May 14, 2015

(65) Prior Publication Data

US 2016/0331808 A1 Nov. 17, 2016

Related U.S. Application Data

(60) Provisional application No. 61/900,904, filed on Nov. 6, 2013.

(51) Int. Cl.

| | |
|---|---|
| ***A61K 48/00*** | (2006.01) |
| ***A61K 38/18*** | (2006.01) |
| ***C12N 5/077*** | (2010.01) |
| ***C12N 15/113*** | (2010.01) |

(52) U.S. Cl.
CPC .............. *A61K 48/00* (2013.01); *A61K 38/18* (2013.01); *A61K 48/005* (2013.01); *A61K 48/0075* (2013.01); *C12N 5/0657* (2013.01); *C12N 15/1136* (2013.01); *C12N 2310/11* (2013.01)

(58) Field of Classification Search
CPC ...................................................... A61K 38/18
See application file for complete search history.

(56) References Cited

U.S. PATENT DOCUMENTS

2002/0164735 A1* 11/2002 Olson ................ C07K 14/4702 435/183

OTHER PUBLICATIONS

Khaw et al. Circulation 74(2):239-244,1986.*
Kochegarov et al. presented another abstract the 2015 Annual Meetings of the American Society for Cell Biology (Molecular Biology of the Cell. Dec. 2015, vol. 26, No. 25, Abstract No. P718). (Year: 2015).*
Kochegarov et al. presented an abstract at 2012 Experimental Biology Meetings (FASEB Journal. Apr. 2012. vol. 26; see abstract) (Year: 2012).*
Fumoto et al. (Novel Gene Therapy Approaches. Ed. Ming Wei. InTech publications. 2013. Chapter 1:Targeted Gene Delivery: Importance of Administration Routes.pp. 3-31) (Year: 2013).*

* cited by examiner

*Primary Examiner* — Marcia S Noble
(74) *Attorney, Agent, or Firm* — Winstead PC

(57) ABSTRACT

Methods and products for altering or promoting the development of heart tissue are disclosed. The methods include the use of nucleic acids of cardiogenic inducing factor for treating a subject having heart disease.

3 Claims, 49 Drawing Sheets

Specification includes a Sequence Listing.

TGACCTGTTCGTTGCAACAAATTGATGAGCAATGCTTTTTTATAATGCCAACTTTGTACAAAAAAGT
TGGCGCCCTCATAATCATTTTCCTTATCTGCTTCCTAGTCCTGTATGCCCTTTTCCTAACACTCACA
ACAAAACTAACTAATACTAACATCTCAGACGCTCAGGAAATAGAAACCGTCTGAACTATCCTGCCCG
CCATCATCCTAGTCCTCATCGCCCTCCCATCCCTACGCATCCTTTACATAACAGACGAGGTCAACGA
TCCCTCCCTTACCATCAAATCAATTGGCCACCAATGGTACTGAACCTACGAGTACACCGACTACGGC
GGACTAATCTTCAACTCCTACATACTTCCCCCATTATTCCTAGAACCAGGCGACCTGCGACTCCTTG
ACGTTGACAATCGAGTAGTACTCCCGATTGAAGCCCCCATTCGTATAATAATTACATCACAAGACGT
CTTGCACTCATGAGCTGTCCCCACATTAGGCTTAAAAACAGATGCAATTCCCGGACGTCTAAACCAA
ACCACTTTCACCGCTACACGACCGGGGGTATACTACGGTCAATGCTCTGAAATCTGTGGAGCAAACC
ACAGTTTCATGCCCATCGTCCTAGAATTAATTCCCCTAAAAATCTTTGAAATAGGGCCCGTATTTAC
CCTATAGCACCCCCTCTACCCCCTCTAGAGCC*AAanaAAAAAAAAAAAAAAAAAAAAAAA*
*AAAAAAAAAAAAAAAAAAAAAA*.

FIG. 11 atggcacatgcagcgcaagtaggtctacaagacgctacttcccctatcatagaagagcttatcacct
ttcatgatcacgccctcataatcattttccttatctgcttcctagtcctgtatgcccttttcctaac
actcacaacaaaactaactaatactaacatctcagacgctcaggaaatagaaaccgtctgaactatc
ctgcccgccatcatcctagtcctcatcgccctcccatccctacgcatcctttacataacagacgagg
tcaacgatccctcccttaccatcaaatcaattggccaccaatggtactgaacctacgagtacaccga
ctacggcggactaatcttcaactcctacatacttcccccattattcctagaaccaggcgacctgcga
ctccttgacgttgacaatcgagtagtactcccgattgaagcccccattcgtataataattacatcac
aagacgtcttgcactcatgagctgtccccacattaggcttaaaaacagatgcaattcccggacgtct
aaaccaaaccactttcaccgctacacgaccgggggtatactacggtcaatgctctgaaatctgtgga
gcaaaccacagtttcatgcccatcgtcctagaattaattcccctaaaaatctttgaaatagggcccg
tatttaccctatagcacccccctctacccccctctagagcc

Download ⌄ GenBank Graphics

Homo sapiens, Similar to cytochrome c oxidase II, clone IMAGE: 3681696, mRNA

Sequence ID: gb|BC013388.1| Length: 747 Number of Matches: 1

Range 1: 81 to 747 GenBank Graphics ▽ Next Match △ Previous Match

| Score | Expect | Identities | Gaps | Strand |
|---|---|---|---|---|
| 1212 bits(656) | 0.0 | 663/667(99%) | 0/667(0%) | Plus/Plus |

```
Query  1    CGCCCTCATAATCATTTTCCTTATCTGCTTCCTAGTCCTGTATGCCCTTTTCCTAACACT  60
            ||||||||||||||||||||||||||||| ||||||||||||||||||||||||||||||
Sbjct  81   CGCCCTCATAATCATTTTCCTTATCTGCTCCCTAGTCCTGTATGCCCTTTTCCTAACACT  140

Query  61   CACAACAAAACTAACTAATACTAACATCTCAGACGCTCAGGAAATAGAAACCGTCTGAAC  120
            ||||||||||||||||||||||||||||||||||||||||||||||||||||||||||||
Sbjct  141  CACAACAAAACTAACTAATACTAACATCTCAGACGCTCAGGAAATAGAAACCGTCTGAAC  200

Query  121  TATCCTGCCCGCCATCATCCTAGTCCTCATCGCCCTCCCATCCCTACGCATCCTTTACAT  180
            ||||||||||||||||||||||||||||||||||||||||||||||||||||||||||||
Sbjct  201  TATCCTGCCCGCCATCATCCTAGTCCTCATCGCCCTCCCATCCCTACGCATCCTTTACAT  260

Query  181  AACAGACGAGGTCAACGATCCCTCCCTTACCATCAAATCAATTGGCCACCAATGGTACTG  240
            ||||||||||||||||||||||||||||||||||||||||||||||||||||||||||||
Sbjct  261  AACAGACGAGGTCAACGATCCCTCCCTTACCATCAAATCAATTGGCCACCAATGGTACTG  320
```

```
Query  241  AACCTACGAGTACACCGACTACGGCGGACTAATCTTCAACTCCTACATACTTCCCCCATT  300
            ||||||||||||||||||||||||||||||||||||||||||||||||||||||||||||
Sbjct  321  AACCTACGAGTACACCGACTACGGCGGACTAATCTTCAACTCCTACATACTTCCCCCATT  380

Query  301  ATTCCTAGAACCAGGCGACCTGCGACTCCTTGACGTTGACAATCGAGTAGTACTCCCGAT  360
            ||||||||||||||||||||||||||||||||||||||||||||||||||||||||||||
Sbjct  381  ATTCCTAGAACCAGGCGACCTGCGACTCCTTGACGTTGACAATCGAGTAGTACTCCCGAT  440

Query  361  TGAAGCCCCCATTCGTATAATAATTACATCACAAGACGTCTTGCACTCATGAGCTGTCCC  420
            ||||||||||||||||||||||||||||||||||||||||||||||||||||||||||||
Sbjct  441  TGAAGCCCCCATTCGTATAATAATTACATCACAAGACGTCTTGCACTCATGAGCTGTCCC  500

Query  421  CACATTAGGCTTAAAAACAGATGCAATTCCCGGACGTCTAAACCAAACCACTTTCACCGC  480
            ||||||||||||||||||||||||||||||||||||||||||||||||||||||||||||
Sbjct  501  CACATTAGGCTTAAAAACAGATGCAATTCCCGGACGTCTAAACCAAACCACTTTCACCGC  560

Query  481  TACACGACCGGGGGTATACTACGGTCAATGCTCTGAAATCTGTGGAGCAAACCACAGTTT  540
            ||||||||||||||||||||||||||||||||||||||||||||||||||||||||||||
Sbjct  561  TACACGACCGGGGGTATACTACGGTCAATGCTCTGAAATCTGTGGAGCAAACCACAGTTT  620

Query  541  CATGCCCATCGTCCTAGAATTAATTCCCCTAAAAATCTTTGAAATAGGGCCCGTATTTAC  600
            ||||||||||||||||||||||||||||||||||||||||||||||||||||||||||||
Sbjct  621  CATGCCCATCGTCCTAGAATTAATTCCCCTAAAAATCTTTGAAATAGGGCCCGTATTTAC  680

Query  601  CCTATAGCACCCCCTCTACCCCCTCTAGAGCCaaanaaaaaaaaaaaaaaaaaaaaaaaa  660
            |||||||||||||||||||||||| |||||||||  ||||||||||||||||||||||||
Sbjct  681  CCTATAGCACCCCCTCTACCCCCTTTAGAGCCAACCAAAAAAAAAAAAAAAAAAAAAAAA  740

Query  661  aaaaaaa  667
            |||||||
Sbjct  741  AAAAAAA  747
```

FIG. 17 (continued)

FIG. 24A
DNA

TTCTTGGATG ACGTCGGCGT TGCTGGGAGA ATGTGCCGTT CCTGCCCTGC CTCCACCCAC
CTCGGGAGCA GAAGCCCGGC CTGGACACCC CTCGGCCTGG ACACCCCTCG AAGGAGAGGG
CGCTTCCTTG AGTAGGTGGG CTCCCCTTGC CCTTCCCTCC CTATCACTCC ATACTGGGGT
GGGCTGGAGG AGGCCACAGG CCAGCTATTG TAAAAGCTTT TTATTTTAGT AAAATATACA
GAAGTTTGTC TTCAA

FIG. 24B
RNA

AAGAACCUAC UGCAGCCGCA ACGACCCUCU UACACGGCAA GGACGGGACG GAGGUGGGUG
GAGCCCUCGU CUUCGGGCCG GACCUGUGGG GAGCCGGACC UGUGGGGAGC UUCCUCUCCC
GCGAAGGAAC UCAUCCACCC GAGGGGAACG GGAAGGGAGG GAUAGUGAGG UAUGACCCCA
CCCGACCUCC UCCGGUGUCC GGUCGAUAAC AUUUUCGAAA AAUAAAAUCA UUUUAUAUGU
CUUCAA

SEQUENCE LISTING

<160> NUMBER OF SEQ ID NOS: 21

<210> SEQ ID NO 1
<211> LENGTH: 246
<212> TYPE: RNA
<213> ORGANISM: Homo sapiens

<400> SEQUENCE: 1
aagaaccuac ugcagccgca acgacccucu uacacggcaa ggacgggacg gaggugggug 60
gagcccucgu cuucgggccg gaccuguggg gagccggacc ugugggggagc uuccucuccc 120 gcgaaggaac ucauccaccc gaggggaacg ggaagggagg gauagugagg uaugacccca 180
cccgaccucc uccggugucc ggucgauaac auuuucgaaa aauaaaauca uuuuauaugu 240
cuucaa 246

<210> SEQ ID NO 2
<211> LENGTH: 246
<212> TYPE: RNA
<213> ORGANISM: Homo sapiens

<400> SEQUENCE: 2
aacuucugua uauuuuacua aaauaaaaag cuuuuacaau agcuggccug uggccuccuc 60
cagcccaccc caguauggag ugauagggag ggaagggcaa ggggagccca ccuacucaag 120
gaagcgcccu cuccuucgag gggguccag gccgaggggu guccaggccg ggcuucugcu 180
cccgaggugg guggaggcag ggcaggaacg gcacauucuc ccagcaacgc cgacgucauc 240
caagaa 246

<210> SEQ ID NO 3
<211> LENGTH: 761
<212> TYPE: DNA
<213> ORGANISM: Homo sapiens
<220> FEATURE:
<221> NAME/KEY: misc_feature
<222> LOCATION: (706)..(706)
<223> OTHER INFORMATION: n is a, c, g, or t

<400> SEQUENCE: 3
tgacctgttc gttgcaacaa attgatgagc aatgcttttt tataatgcca actttgtaca 60
aaaaagttgg cgccctcata atcattttcc ttatctgctt cctagtcctg tatgcccttt 120

```
tcctaacact cacaacaaaa ctaactaata ctaacatctc agacgctcag gaaatagaaa    180

ccgtctgaac tatcctgccc gccatcatcc tagtcctcat cgccctccca tccctacgca    240

tcctttacat aacagacgag gtcaacgatc cctcccttac catcaaatca attggccacc    300

aatggtactg aacctacgag tacaccgact acggcggact aatcttcaac tcctacatac    360

ttccccccatt attcctagaa ccaggcgacc tgcgactcct tgacgttgac aatcgagtag    420

tactcccgat tgaagccccc attcgtataa taattacatc acaagacgtc ttgcactcat    480

gagctgtccc cacattaggc ttaaaaacag atgcaattcc cggacgtcta aaccaaacca    540

ctttcaccgc tacacgaccg ggggtatact acggtcaatg ctctgaaatc tgtggagcaa    600

accacagttt catgcccatc gtcctagaat taattcccct aaaaatcttt gaaatagggc    660

ccgtatttac cctatagcac cccctctacc ccctctagag ccaaanaaaa aaaaaaaaaa    720

aaaaaaaaaa aaaaaaaaaa aaaaaaaaaa aaaaaaaaaa a                        761


<210> SEQ ID NO 4
<211> LENGTH: 709
<212> TYPE: DNA
<213> ORGANISM: Homo sapiens

<400> SEQUENCE: 4

atggcacatg cagcgcaagt aggtctacaa gacgctactt cccctatcat agaagagctt     60

atcacctttc atgatcacgc cctcataatc attttcctta tctgcttcct agtcctgtat    120

gcccttttcc taacactcac aacaaaacta actaatacta acatctcaga cgctcaggaa    180

atagaaaccg tctgaactat cctgcccgcc atcatcctag tcctcatcgc cctcccatcc    240

ctacgcatcc tttacataac agacgaggtc aacgatccct cccttaccat caaatcaatt    300

ggccaccaat ggtactgaac ctacgagtac accgactacg gcggactaat cttcaactcc    360

tacatacttc cccccattatt cctagaacca ggcgacctgc gactccttga cgttgacaat    420

cgagtagtac tcccgattga agcccccatt cgtataataa ttacatcaca agacgtcttg    480

cactcatgag ctgtccccac attaggctta aaaacagatg caattcccgg acgtctaaac    540

caaaccactt tcaccgctac acgaccgggg gtatactacg gtcaatgctc tgaaatctgt    600

ggagcaaacc acagtttcat gcccatcgtc ctagaattaa ttcccctaaa aatctttgaa    660

atagggcccg tatttaccct atagcacccc ctctaccccc tctagagcc                709


<210> SEQ ID NO 5
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 5

taatacgact cactataggg gtaaaacgac ggccag                               36


<210> SEQ ID NO 6
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 6

taatacgact cactataggg caggaaacag ctatgac                              37
```

```
<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 7

ggagcttgac catgcgctga a                                                21


<210> SEQ ID NO 8
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 8

tgagaaccga cacaaagcaa gagg                                             24


<210> SEQ ID NO 9
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 9

ccaagggctt caccgggctc aa                                               22


<210> SEQ ID NO 10
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 10

tggcagaggt ggaatggatc acagg                                            25


<210> SEQ ID NO 11
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 11

ggactctcca ccgcctccct ctc                                              23


<210> SEQ ID NO 12
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 12

ccccgcttca tccttcgctc tga                                              23


<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 13
tccatgaagg ctgcccaact 20

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
tggcgccaca tctgattgat 20

<210> SEQ ID NO 15
<211> LENGTH: 691
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (56)..(56)
<223> OTHER INFORMATION: n is a, c, g, or u

<400> SEQUENCE: 15
uuuuuuuuuu uuuuuuuuuu uuuuuuuuuu uuuuuuuuuu uuuuuuuuuu uuuuunuuug 60
gcucuagagg ggguagaggg ggugcuauag gguaaaauacg ggcccuauuu caaagauuuu 120
uaggggaauu aauucuagga cgaugggcau gaaacugugg uuugcuccac agauuucaga 180
gcauugaccg uaguauaccc ccggucgugu agcggugaaa gugguuuggu uuagacgucc 240
gggaauugca ucuguuuuua agccuaaugu ggggacagcu caugagugca agacgucuug 300
ugauguaauu auuauacgaa ugggggcuuc aaucgggagu acuacucgau ugucaacguc 360
aaggagucgc aggucgccug guucuaggaa uaaaugggggga aguauguagg aguugaagau 420
uaguccgccg uagucggugu acucguaggu ucaguaccau ugguggccaa uugauuugau 480
gguaagggag ggaucguuga ccucgucugu uauguaaagg augcguaggg augggagggc 540
gaugaggacu aggaugaugg cgggcaggau aguucagacg guuucuauuu ccugagcguc 600
ugagauguua guauuaguua guuuuguugu gaguguuagg aaaagggcau acaggacuag 660
gaagcagaua aggaaaauga uuaugagggc g 691

<210> SEQ ID NO 16
<211> LENGTH: 632
<212> TYPE: RNA
<213> ORGANISM: Homo sapiens

<400> SEQUENCE: 16
ggcucuagag gggguagagg gggugcuaua ggguaaaauac gggcccuauu ucaaagauuu 60
uuaggggaau uaauucuagg acgaugggca ugaaacugug guuugcucca cagauuucag 120
agcauugacc guaguauacc cccggucgug uagcggugaa agugguuugg uuuagacguc 180
cgggaauugc aucuguuuuu aagccuaaug uggggacagc ucaugagugc aagacgucuu 240
gugauguaau uauuauacga augggggcuu caaucgggag uacuacucga uugucaacgu 300
caaggagucg caggucgccu gguucuagga auaaaugggg aaguauguag gaguugaaga 360
uuaguccgcc guagucggug uacucguagg uucaguacca uugguggcca auugauuuga 420
ugguaaggga gggaucguug accucgucug uuauguaaag gaugcguagg gaugggaggg 480

```
cgaugaggac uaggaugaug gcgggcagga uaguucagac gguuucuauu uccugagcgu    540

cugagauguu aguauuaguu aguuuuguug ugaguguuag gaaaagggca uacaggacua    600

ggaagcagau aaggaaaaug auuaugaggg cg                                  632


<210> SEQ ID NO 17
<211> LENGTH: 667
<212> TYPE: DNA
<213> ORGANISM: Homo sapiens
<220> FEATURE:
<221> NAME/KEY: misc_feature
<222> LOCATION: (636)..(636)
<223> OTHER INFORMATION: n is a, c, g, or t

<400> SEQUENCE: 17

cgccctcata atcattttcc ttatctgctt cctagtcctg tatgcccttt tcctaacact     60

cacaacaaaa ctaactaata ctaacatctc agacgctcag gaaatagaaa ccgtctgaac    120

tatcctgccc gccatcatcc tagtcctcat cgccctccca tccctacgca tcctttacat    180

aacagacgag gtcaacgatc cctcccttac catcaaatca attggccacc aatggtactg    240

aacctacgag tacaccgact acggcggact aatcttcaac tcctacatac ttcccccatt    300

attcctagaa ccaggcgacc tgcgactcct tgacgttgac aatcgagtag tactcccgat    360

tgaagccccc attcgtataa taattacatc acaagacgtc ttgcactcat gagctgtccc    420

cacattaggc ttaaaaacag atgcaattcc cggacgtcta aaccaaacca ctttcaccgc    480

tacacgaccg gggtatact acggtcaatg ctctgaaatc tgtggagcaa accacagttt     540

catgcccatc gtcctagaat taattcccct aaaaatcttt gaaatagggc ccgtatttac    600

cctatagcac cccctctacc ccctctagag ccaaanaaaa aaaaaaaaaa aaaaaaaaaa    660

aaaaaaa                                                              667


<210> SEQ ID NO 18
<211> LENGTH: 747
<212> TYPE: DNA
<213> ORGANISM: Homo sapiens

<400> SEQUENCE: 18

gggatggcac atgcagcgca agtaggtcta caagacgcta cttcccctat catagaagag     60

cttatcacct ttcatgatca cgccctcata atcattttcc ttatctgctc cctagtcctg    120

tatgcccttt tcctaacact cacaacaaaa ctaactaata ctaacatctc agacgctcag    180

gaaatagaaa ccgtctgaac tatcctgccc gccatcatcc tagtcctcat cgccctccca    240

tccctacgca tcctttacat aacagacgag gtcaacgatc cctcccttac catcaaatca    300

attggccacc aatggtactg aacctacgag tacaccgact acggcggact aatcttcaac    360

tcctacatac ttcccccatt attcctagaa ccaggcgacc tgcgactcct tgacgttgac    420

aatcgagtag tactcccgat tgaagccccc attcgtataa taattacatc acaagacgtc    480

ttgcactcat gagctgtccc cacattaggc ttaaaaacag atgcaattcc cggacgtcta    540

aaccaaacca ctttcaccgc tacacgaccg gggtatact acggtcaatg ctctgaaatc     600

tgtggagcaa accacagttt catgcccatc gtcctagaat taattcccct aaaaatcttt    660

gaaatagggc ccgtatttac cctatagcac cccctctacc ccctttagag ccaaccaaaa    720

aaaaaaaaaa aaaaaaaaaa aaaaaaa                                        747


<210> SEQ ID NO 19
<211> LENGTH: 10
```

-continued

```
<212> TYPE: RNA
<213> ORGANISM: Artificial Sequence
<220> FEATURE:
<223> OTHER INFORMATION: Synthetic Polynucleotide

<400> SEQUENCE: 19

ggcucuagag                                                              10


<210> SEQ ID NO 20
<211> LENGTH: 255
<212> TYPE: DNA
<213> ORGANISM: Homo sapiens

<400> SEQUENCE: 20

ttcttggatg acgtcggcgt tgctgggaga atgtgccgtt cctgccctgc ctccacccac     60

ctcgggagca gaagcccggc ctggacaccc ctcggcctgg acacccctcg aaggagaggg    120

cgcttccttg agtaggtggg ctccccttgc ccttccctcc ctatcactcc atactggggt    180

gggctggagg aggccacagg ccagctattg taaaagcttt ttattttagt aaaatataca    240

gaagtttgtc ttcaa                                                     255


<210> SEQ ID NO 21
<211> LENGTH: 691
<212> TYPE: DNA
<213> ORGANISM: Homo sapiens
<220> FEATURE:
<221> NAME/KEY: misc_feature
<222> LOCATION: (636)..(636)
<223> OTHER INFORMATION: n is a, c, g, or t

<400> SEQUENCE: 21

cgccctcata atcattttcc ttatctgctt cctagtcctg tatgcccttt tcctaacact     60

cacaacaaaa ctaactaata ctaacatctc agacgctcag gaaatagaaa ccgtctgaac    120

tatcctgccc gccatcatcc tagtcctcat cgccctccca tccctacgca tcctttacat    180

aacagacgag gtcaacgatc cctcccttac catcaaatca attggccacc aatggtactg    240

aacctacgag tacaccgact acggcggact aatcttcaac tcctacatac ttcccccatt    300

attcctagaa ccaggcgacc tgcgactcct tgacgttgac aatcgagtag tactcccgat    360

tgaagccccc attcgtataa taattacatc acaagacgtc ttgcactcat gagctgtccc    420

cacattaggc ttaaaaacag atgcaattcc cggacgtcta aaccaaacca ctttcaccgc    480

tacacgaccg ggggtatact acggtcaatg ctctgaaatc tgtggagcaa accacagttt    540

catgcccatc gtcctagaat taattcccct aaaaatcttt gaaatagggc ccgtatttac    600

cctatagcac cccctctacc ccctctagag ccaaanaaaa aaaaaaaaaa aaaaaaaaaa    660

aaaaaaaaaa aaaaaaaaaa aaaaaaaaaa a                                   691
```

CARDIAC MYOFIBRIL INDUCTION

RELATED APPLICATION

This application claims priority under 35 U.S.C. § 119(e) to U.S. provisional patent application U.S. Ser. No. 61/900,904, filed Nov. 6, 2013, which is incorporated herein by reference.

FEDERALLY SPONSORED RESEARCH

This invention was made with Government support under NIH Grant No. R01HL061246 and American Heart Association Grant No. 10GRNT4530001. The Government has certain rights in this invention.

BACKGROUND OF INVENTION

Heart disease is responsible for one out of every four deaths in the United States, making it the number one killer in our nation (Parker, Health Guidance, 2012). Survivors of myocardial infarctions (heart attacks) are left with scar tissue that cannot function like that of healthy myocardial muscle, leading to limitations on physical activity and exertion. By developing this scar tissue, the human body considers the heart healed, but the heart remains damaged due to its inability to function as successfully as before the myocardial infarction. On average, 600,000 people suffer from heart attacks in the United States yearly with 190,000 of those cases happening to people who have already experienced a heart attack (CDC, 2013).

Cardiogenesis and its related pathways are very significant for the treatment and prevention of heart disease. The Mexican axolotl, *Ambystoma mexicanum*, is a vertebrate animal model for studying myofibrillogenesis due to its naturally-occurring lethal recessive mutation caused by gene c for "cardiac non-function". Homozygous recessive (c/c) "mutant" embryos have hearts consisting of only a single layer of cells and lacking organized myofibrils. The mutant hearts fail to beat. Among some earlier studies, it was discovered that the necessary components of the sarcomere did not become organized into functioning myofibrils in mutant organisms and the reason that they did not conjugate correctly was due to an absence of muscle tropomyosin (Lemanski, Dev. Biol., 1973, and Zhang, J. of Cellular Biochem., 2007).

SUMMARY OF INVENTION

Treatment of heart tissue with a molecule capable of rescuing the heart by promoting the development of functional heart tissue is an aspect of the invention. The invention is based, in some aspects, on a method of treating a subject by administering a nucleic acid of a cardiogenic inducing factor (CIF) to the subject.

In some embodiments, the nucleic acid is a DNA molecule which expresses a Cardiogenic Inducing RNA (CIR). In other embodiments the CIR has 85% homology to SEQ ID NO. 1. In another embodiment the CIR has 90% homology to SEQ ID NO. 1. In some embodiments, the CIR has 95% homology to SEQ ID NO. 1. In other embodiments the CIR is SEQ ID NO. 1. In another embodiment the DNA sequence encoding CIR is found in SEQ ID NO. 20.

In another embodiment, the nucleic acid is a DNA molecule which expresses a CIR that has 85% homology to SEQ ID NO. 2, 15 or 16. In other embodiments, the CIR has 90% homology to SEQ ID NO. 2, 15 or 16. In some embodiments, the CIR has 95% homology to SEQ ID NO. 2, 15 or 16. In other embodiments the CIR is SEQ ID NO. 2, 15 or 16. In another embodiment the DNA sequence encoding CIR is found in SEQ ID NO. 21.

In yet other embodiments the subject has heart failure or heart tissue damage or has a family history of heart failure or heart tissue damage.

The invention is a method of treating a subject, in some embodiments, by administering a composition comprising a nucleic acid of a CIF to a subject who has the composition directly administered. In other embodiments, the invention is a method of treating a subject, by administering a composition comprising a nucleic acid of a CIF to a subject who has the composition administered to a cell wherein the cell is administered to the subject.

In some embodiments, the invention is a method of treating a subject by administering a composition comprising a nucleic acid of a CIF to a subject by direct injection. In other embodiments, the direct injection is selected from the group consisting of intravenous, intradermal, subcutaneous, and intramuscular injections.

In another embodiment the nucleic acid is a RNA molecule which is a Cardiogenic Inducing RNA (CIR).

In other aspects, the invention is a method of producing a cardiomyocyte, by contacting a stem cell with an isolated CIR, in an effective amount to induce differentiation into a cardiomyocyte. In some embodiments, the stem cell is contacted directly with the CIR. In other embodiments, the stem cell is contacted with an expression vector having a nucleic acid which expresses the CIR. In another embodiment, the stem cell is an embryonic stem cell. The stem cell is also a pluripotent human stem cell in some embodiments.

The invention, in some aspects, is a cardiomyocyte comprising an exogenous Cardiogenic Inducing RNA (CIR).

In another aspect, the invention is an isolated stabilized RNA, wherein the RNA is a CIR. In one embodiment, the CIR is encapsulated in a nanoparticle, lipid, polymer, cholesterol, or cell penetrating peptide. In another embodiment, the CIR includes at least one nucleoside backbone modification. In other embodiments, the nucleoside backbone modification is a phosphorothioate modification. The CIR comprises a poly-A tail, in some embodiments. In yet another embodiment, the CIR comprises a secondary structure which includes at least 4 loops. These loops include a first terminal loop, a second terminal loop and 2 central loops, interconnected by three stems, wherein the first terminal loop has at least one additional stem and the second terminal loop has at least two additional stems.

In another aspect, the invention can encompass a CIR, wherein the CIR includes at least one modified nucleoside. In one embodiment, at least one modified nucleoside comprises at least one modification as compared to the chemical structure of an A, G, U or C ribonucleotide. In other embodiments, at least one modification is located in a nucleoside base and/or sugar portion. In another embodiment, at least one modified nucleoside is 1-methylpseudouridine or pseudouridine. In yet another embodiment, at least one modified nucleoside is a 2' O-methyl modified nucleoside.

In some aspects, the invention includes a vector comprising an isolated nucleic acid encoding a cardiogenic inducing factor (CIF) and a promoter. In some embodiments, the isolated nucleic acid comprises a nucleotide sequence which hybridizes under stringent conditions to the nucleotide sequence of SEQ ID NO. 1. In other embodiments the isolated nucleic acid comprises a nucleotide sequence which hybridizes under stringent conditions to the nucleotide sequence of SEQ ID NO. 2.

In other aspects, the invention includes the host cell comprising the vector having an isolated nucleic acid encoding a CIF, a promoter, and its embodiments herein. The host cell can comprise of a stem cell, a Chinese Hamster Ovary cell, an insect cell, an *E. coli* cell, or a yeast cell, in some embodiments.

This invention is not limited in its application to the details of construction and the arrangement of components set forth in the following description or illustrated in the drawings. The invention is capable of other embodiments and of being practiced or of being carried out in various ways. Each of the above embodiments and aspects may be linked to any other embodiment or aspect. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 11 shows human fetal heart RNA CIR 2's corresponding DNA sequence (SEQ ID NO. 3) Testing for vector contamination revealed that the first 70 nucleotides were contaminants (bolded) and so not truly part of the cDNA sequence. The poly A tail (italicized) was also excluded for some secondary structure analyses, leaving the trimmed sequence (underlined).

FIG. 12 shows the sequence identity of the DNA sequence of CIR 2 and cytochrome c oxidase subunit II (COX2) gene (607/684 nucleotides). The pictured nucleotides are nucleotides 7594-8302 (709 characters) of the *Homo sapiens* B3 mitochondrion, complete genome with the underlined section representing the gene for cytochrome c oxidase subunit II and the gray highlighted region representing the DNA sequence of CIR 2 (SEQ ID NO. 4) . Since the nucleotides that CIR 2 has in common with *Homo sapiens* B3 mitochondrion include most of the COX2 gene nucleotide sequence, this suggests CIR 2's sequence is associated with the COX2 gene.

FIG. 15 displays slight striations (15I) and more substantial striations (15J). These striations appear as bands or chains of fluorescent dots and prove the presence of functional sarcomeric structures within the rescued mutant heart.

FIG. 17 is an examination of *Homo sapiens*, similar to cytochrome c oxidase II, clone IMAGE: 3681696, mRNA and CIR 2. There is a 96% match to the DNA sequence of CIR 2. The alignment shows that the DNA sequence of CIR 2 matches to the cytochrome c oxidase II mRNA gene from the beginning to the poly A tail. The upper sequence corresponds to SEQ ID NO. 17 and the lower sequence corresponds to SEQ ID NO. 18.

FIG. 23 shows stem cell culture.

FIG. 24 presents the sequences of CIR cloned as DNA (SEQ ID NO. 20) (FIG. 24A) and converted into RNA (SEQ ID NO. 1) (FIG. 24B).

DETAILED DESCRIPTION OF INVENTION

The invention relates to methods and products for modulating heart tissue function. It has been discovered that cardiogenic inducing factor (CIF) nucleic acids are useful for modulating heart tissue function. A cardiogenic inducing nucleic acid is a nucleic acid that causes the differentiation of cells into cardiac cells. These nucleic acids are capable of rescuing heart tissue.

Figure 1A:
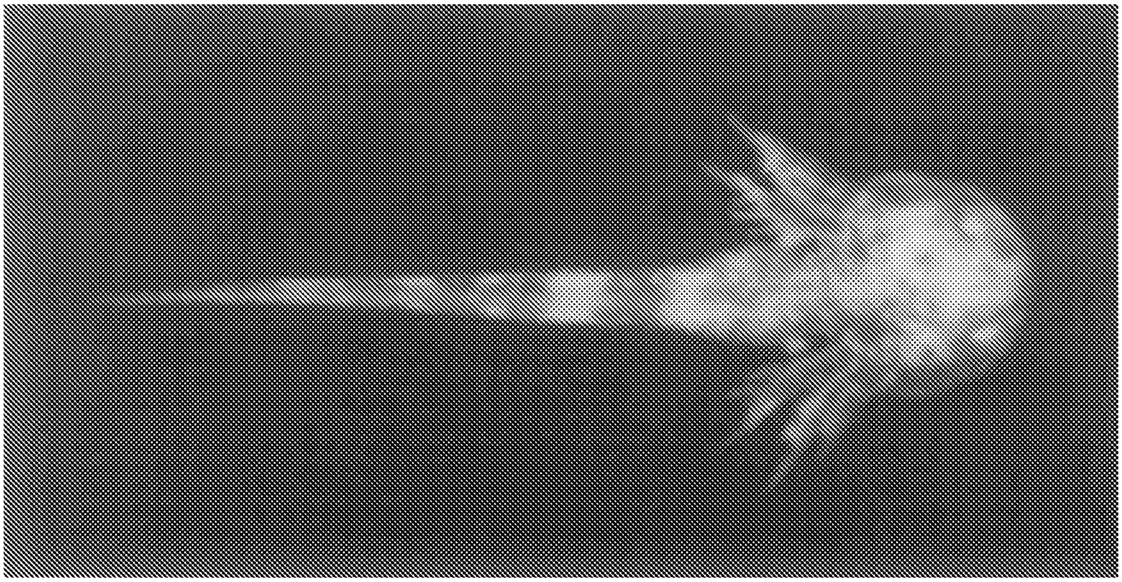
FIG. 1 shows the gross morphology of normal (1A) and cardiac lethal mutant (1B) siblings at (Bordzilovskaya et al., 1989) stages 40-41; Mutant embryos are shorter in length than normal and display ascites.
Figure 1B:
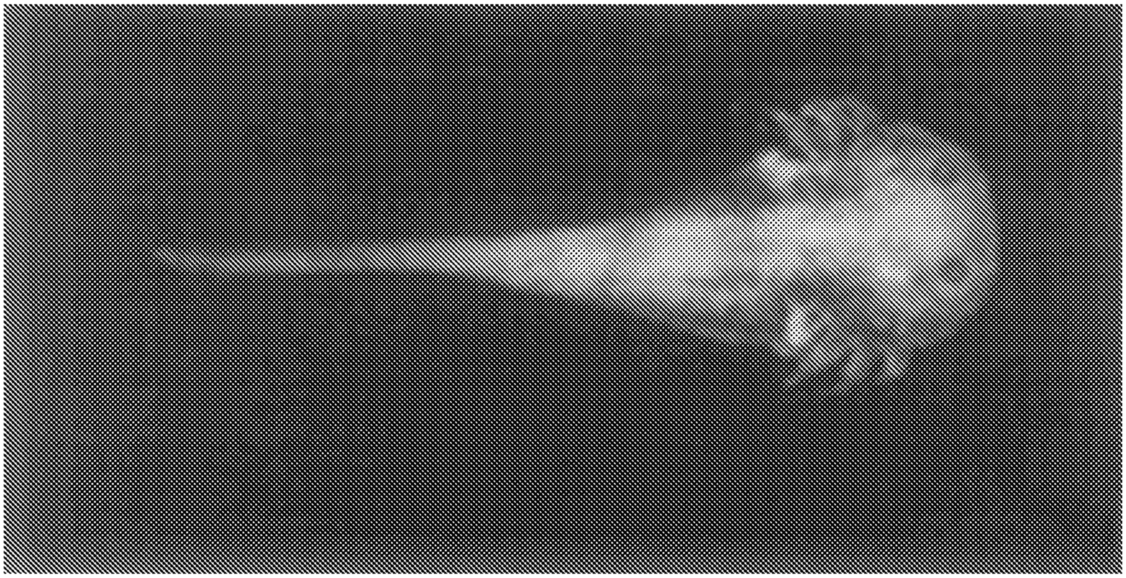
Figure 2A:
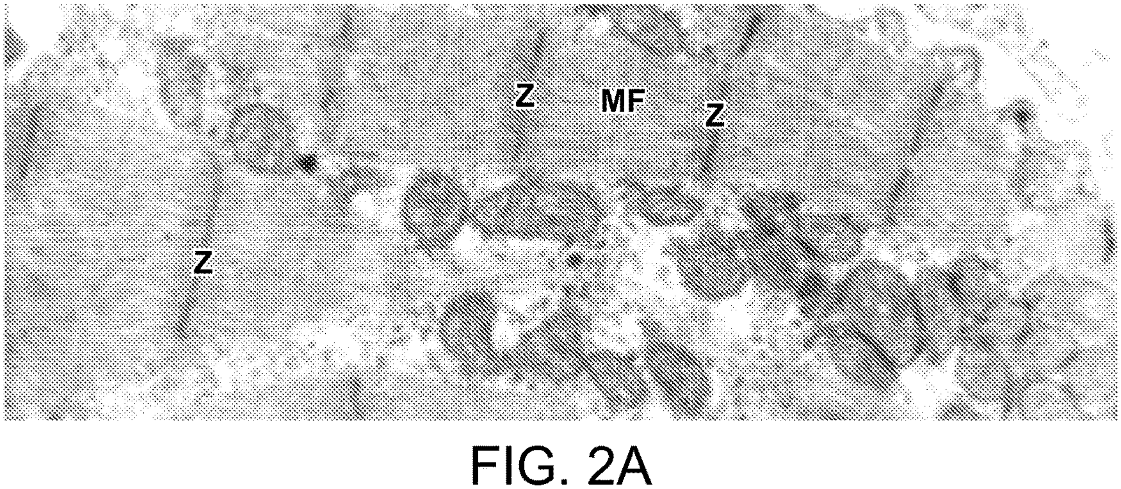
In FIG. 2A, portions of normal (+/+) heart cells contain well organized sarcomeric myofibrils (MF) and Z bands (Z) are shown. Mutant heart cells without any treatment, shown in 2B, show no obvious myofibrils, only amorphous proteinaceous material (AM). Mutant heart cells treated with axolotl Myofibril-Inducing RNA (MIR) show organized sarcomeric myofibrils (MF) complete with Z bands (2C).
Figure 2B:
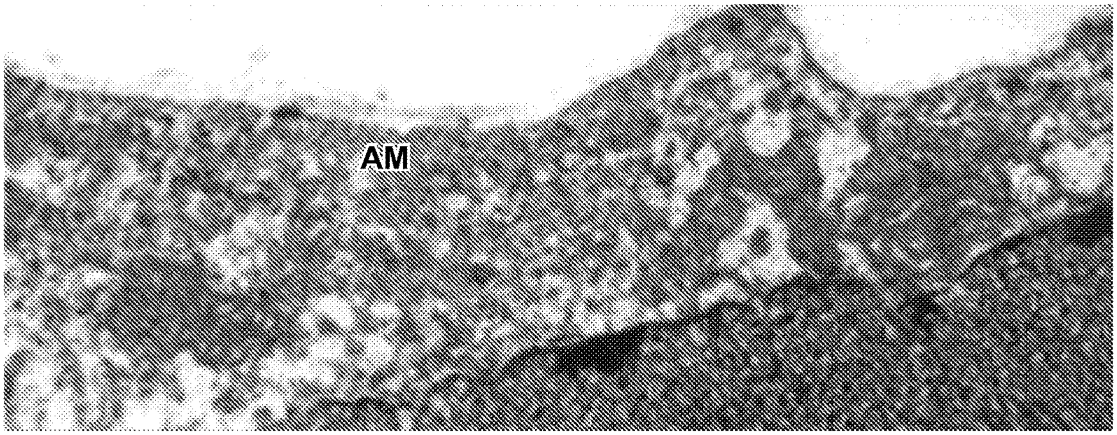
FIG. 2 shows electron micrographs of axolotl embryonic hearts.
Figure 2C:
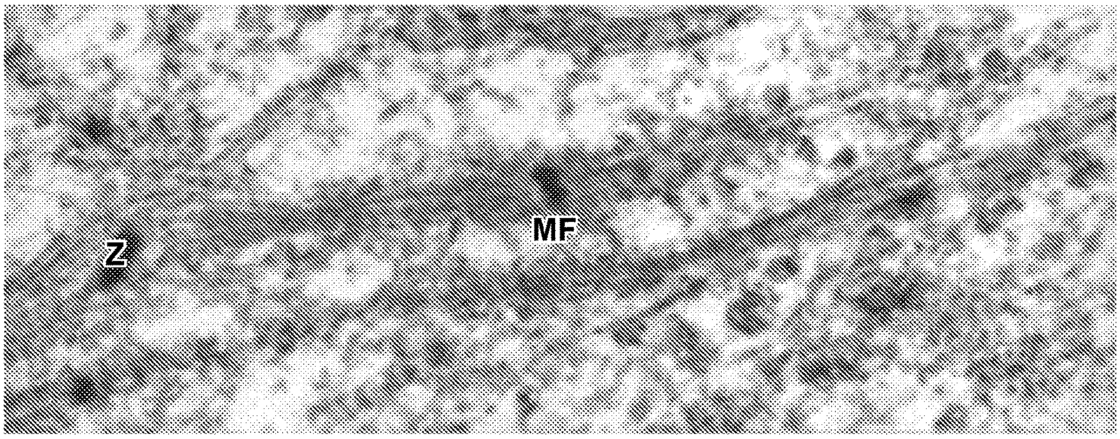

Normal hearts develop normal sarcomeric myofibrils whereas mutant hearts have only amorphous proteinaceous collections (FIG. 2 A, B). The Mexican axolotl, *Ambystoma mexicanum*, is a useful model to study heart development. The animals have a recessive lethal cardiac mutation in gene "c", which prevents the initiation of heart contractions which normally begin at stages 34-35, as described in the staging series by the Bordzilovskaya et al (1989). These are the stages when normal hearts begin to beat rhythmically. The lack of contractions in mutant hearts is due to a lack of tropomyosin expression and organized sarcomeric myofibrils, which are replaced by a collection of cytoplasmic amorphous materials (Lemanski, 1973). The mutant hearts remain quiescent and the embryos develop an ascites condition in the thorax region (FIG. 1) causing the mutants to die by stage 42 (Lemanski et al., 1973). In earlier studies, Myofibril-Inducing RNA (MIR) from normal embryonic axolotl anterior endoderm which rescues heart development in mutant embryos when included in organ cultures with the mutant hearts was identified (Lemanski et al, 1996; Zhang et al, 2003). In the Examples presented herein 400 randomly cloned genes were expressed in human fetal heart to identify individual RNAs which might rescue mutant hearts in axolotl embryos. An RNA (CIR 1) from the fetal human heart which rescues the axolotl mutant hearts in a manner very similar to the original axolotl MIR was identified.

The examples of the invention involved the analysis of multiple RNAs to identify RNAs that could convert non-muscle cells into cardiac muscle. The results show that RNAs cloned from human fetal heart have the capability of rescuing mutant axolotl hearts in organ culture bioassays. The rescue of mutant hearts was demonstrated by the development of beating in the hearts and the expression of tropomyosin in organized myofibrils after transfection and incubation with CIR 1. This RNA contains 246 bp and was screened for matches in the human genome with BLAST at the NCBI database. We found two high score matches with part of exon 8 of the human N-sulfoglucosaminesulfohydrolase (SGSH) gene on the sense strand of DNA and with the caspase recruitment domain family, member 14 (CARD14), on the antisense strand. These genes, SGSH and CARD14, partially overlap and belong to opposite DNA strands (forward and reverse) on the chromosome 17. Although active CIR 1 belongs to encoding regions, exon 8 in the gene of SGSH and exon 23 in the gene CARD14, is too short (246 nucleotides) to encode a functional protein.

CARD domains were originally characterized based on their involvement in the regulation of caspase activation and apoptosis during inflammation, autoimmune and antiviral responses. CARD protein 14 (CARD14) are novel CARD-containing proteins that belong to the membrane-associated guanylate kinase (MAGUK) family, a class of proteins that functions as molecular scaffolds for the assembly of multiprotein complexes at specialized regions of the plasma membrane. CARD proteins are associated with caspase-9 which upon activation split caspase-3 leading to activation of caspase signaling. Recent studies have found that CARD proteins can also function as components of signaling pathways that lead to activation of the transcription factor NF-κB. NF-κB plays a central role in the activation of genes involved in immunity, inflammation, and apoptosis (13, 14). In unstimulated cells, NF-κB is sequestered in the cytoplasm through interactions with inhibitory IκB proteins.

The examples also demonstrate the identification of a functional homolog of the MIR (in CIR 2), which surprisingly had sequence homology with the human mitochondrial cytochrome c oxidase subunit II gene. After analyzing the 400 human fetal RNA clones, we have found that CIR 2 promoted the synthesis of tropomyosin, normally absent from the mutant heart, allowing for mutant hearts to develop complete sarcomeres and functioning myofibrils. Treatment with human fetal heart RNA CIR 2 leads to the rescue and beating of mutant axolotl hearts through myofibrillogenesis due to tropomyosin synthesis showing that this molecule serves as a human Myofibril-Inducing RNA (MIR).

With and without the poly A tail, the DNA sequence of CIR 2 matches human mitochondrial genetic material and is associated with the human cytochrome c oxidase subunit II gene (COX2). Cytochrome c oxidase is utilized by mitochondria in the process of generating ATP by creating an electrochemical gradient for the electron transport chain through donation of electrons. Each of four cytochrome c molecules can donate an electron to oxygen, leading to the generation of two water molecules. The discovery that CIR 2 is associated with the COX2 gene was very a surprising observation because the axolotl MIR has no known or clear associations with mitochondria or the electron transport chain.

Because human myocardial cells lack the ability to regenerate and cannot fully recover from injury, the innovation of a biomedical technique to repair and regenerate these heart cells would be invaluable. By identifying this class of human myofibril-inducing RNAs that initiate the development of healthy functioning cardiac tissue in mutant axolotl hearts, we have the ability to promote myofibrillogenesis in damaged human heart tissue. Our discovery of these unique RNAs could provide survivors of heart disease the possibility of a full recovery by regaining cardiac function through the generation of new healthy heart tissue. Non-functioning areas of scar tissue could be replaced with new heart muscle cells, returning the heart back to normal working condition. These individuals would be able to return to pre-heart-attack activity levels, providing another chance for those patients to live longer healthy lives. Therefore, the results of the invention provide the potential to revolutionize the way heart disease is treated today.

Thus, the invention involves methods of treating a condition (e.g., heart disease) in a mammalian subject, the method comprising administering a CIF or CIR nucleic acid as described herein. A subject can include a human or a non-human mammal, e.g. mouse, rat, guinea pig, rabbit, cat, dog, goat, cow, or horse. In preferred embodiments, a subject is a human. Nucleic acids have been employed as therapeutic moieties in the treatment of disease states in animals, including humans. CIF or CIR nucleic acids can be useful therapeutic modalities that can be configured to be useful in treatment regimes for the treatment of cells, tissues and animals, especially humans.

As used herein, the term "heart disease" generally refers to heart and blood vessel diseases, including atherosclerosis, coronary heart disease (CHD), cerebrovascular disease, and peripheral vascular disease. Cardiovascular disorders are acute manifestations of heart disease and include myocardial infarction, stroke, angina pectoris, transient ischemic attacks, and congestive heart failure. Cardiovascular disease, including atherosclerosis, usually results from the build-up of cholesterol, inflammatory cells, extracellular matrix and plaque. As used herein, the term "coronary heart disease" or "CHD" refers to atherosclerosis in the arteries of the heart causing a heart attack or other clinical manifestation such as unstable angina.

A disease or disorder is "alleviated" if the severity of a sign or symptom of the disease or disorder, the frequency with which such a sign or symptom is experienced by a patient, or both, is reduced.

An "increased risk of developing heart disease" as used herein to refer to an increase in the likelihood or possibility of a subject developing heart disease. This risk can be assessed relative to a subject's own risk, or with respect to a reference population, e.g., to an age-matched and/or gender-matched population, and/or to a population that does not have clinical evidence of heart disease and/or to a family history of heart disease. The reference population may be representative of the subject with regard to approximate age, age group and/or gender.

A CIF nucleic acid, as used herein, is a nucleic acid molecule, DNA or RNA or mixture thereof, that when administered to a mammalian cell having cardiac potential causes the cell to develop a cardiac phenotype. A cell having cardiac potential is a cardiac cell or a stem cell which can be converted to a cardiac cell with a CIF or CIR. In some instances the CIF nucleic acids are expression vectors that are capable of expressing RNA that is useful in the methods of the invention. In other instances, the CIF nucleic acid is an RNA. The RNA that is functional in the methods of the invention is referred to as a cardiogenic inducing RNA (CIR). In some embodiments the CIR is CIR1 or CIR2. In other embodiments the CIR is not MIR.

In some instances, the CIR of the invention share a common secondary structure. Examples of the secondary structure of these RNA molecules is depicted in the boxed structures shown in FIG. 13. Because of the significant similarities in secondary structures of the RNAs of the invention, they may interact and bind with similar regulatory proteins. Thus, these RNAs appear to have evolutionarily conserved secondary structures which may be very significant in early embryonic heart development in all vertebrate species, including human. On the basis of our results, we hypothesize that normal human fetal heart expresses an RNA, which is a functional homolog of the axolotl MIR, and which is required for human heart development and function. Our results clearly show that if we clone these RNAs from human fetal heart and transfect it into mutant axolotl hearts, normal heart development is restored. Secondary structure can be assessed, for instance, using the Gene Bee Program from Moscow State University, Russia.

For example, the predicted secondary structures of CIR 2 have a large portion or area, marked by black boxes in FIG. 13, which appears extremely similar to the secondary structure of the active axolotl MIR. Since CIR2 has a similar secondary structure to the axolotl MIR, it may be capable of binding to the same proteins and promoting the same pathways leading to myofibrillogenesis.

In particular, the RNA may have a secondary structure which includes at least 4 loops, including a first terminal loop, a second terminal loop and 2 central loops, interconnected by three stems, wherein the first terminal loop has at least one additional stem and the second terminal loop has at least two additional stems.

For therapeutics, a mammal, preferably a human, suspected of or at risk of having heart disease is treated by administering CIF or CIR nucleic acid in accordance with this invention. For example, in one non-limiting embodiment, the methods comprise the step of administering to the animal in need of treatment, a therapeutically effective amount of a CIF or CIR nucleic acid as described herein.

The nucleic acids described herein can be formulated for administration to a subject for treating a condition associated with heart disease. It should be understood that the formulations, compositions and methods can be practiced with any of the nucleic acids disclosed herein.

The formulations may conveniently be presented in unit dosage form and may be prepared by any methods well known in the art of pharmacy. The amount of active ingredient (e.g., an nucleic acid or compound of the invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such formulations can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

A formulated CIF or CIR nucleic acid composition can assume a variety of states. In some examples, the composition is at least partially crystalline, uniformly crystalline, and/or anhydrous (e.g., less than 80, 50, 30, 20, or 10% water). In another example, the CIF or CIR nucleic acid is in an aqueous phase, e.g., in a solution that includes water. The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the CIF or CIR nucleic acid composition is formulated in a manner that is compatible with the intended method of administration.

In some embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A CIF or CIR nucleic acid preparation can be formulated or administered (together or separately) in combination with another agent, e.g., another therapeutic agent or an agent that stabilizes a CIF or CIR nucleic acid, e.g., a protein that complexes with CIF or CIR nucleic acid. In some embodiments, the other agent used in combination with the CIF or CIR nucleic acid is an agent that also is useful for treating or preventing any aspects of heart disease. This includes for instance compounds that when administered in effective amounts can act cooperatively, additively or synergistically with a nucleic acid of the invention to modulate cardiac cell activity, and treat any of the conditions in which cardiac cells are involved. Agents other than the molecules of the invention include anti-inflammatory agents, anti-thrombotic agents, anti-coagulants, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules, calcium channel blockers, beta-adrenergic receptor blockers, cyclooxygenase-2 inhibitors, angiotensin system inhibitors, anti-hypertensive agents, and/or combinations thereof.

A composition that includes a CIF or CIR nucleic acid can be delivered to a subject by a variety of routes. Exemplary routes include: intravenous, intradermal, topical, rectal, parenteral, anal, intranasal, pulmonary. The term "therapeutically effective amount" is the amount of nucleic acid present in the composition that is needed to provide the desired level of heart cells in the subject to be treated to give the anticipated physiological response. The term "physiologically effective amount" is that amount delivered to a subject to give the desired palliative or curative effect. The term "pharmaceutically acceptable carrier" means that the carrier can be administered to a subject with no significant adverse toxicological effects to the subject.

The CIF or CIR nucleic acid molecules of the invention can be incorporated into pharmaceutical compositions suitable for administration. Such compositions typically include one or more species of CIF or CIR nucleic acid and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target heart cells, intravascular injection would be a logical choice. The vascular endothelial cells could also be targeted by coating a balloon catheter with the CIF or CIR nucleic acid and mechanically introducing the nucleic acid.

Topical administration refers to the delivery to a subject by contacting the formulation directly to a surface of the subject. The most common form of topical delivery is to the skin, but a composition disclosed herein can also be directly applied to other surfaces of the body, e.g., to a mucous membrane, to surfaces of a body cavity or to an internal surface.

Both the oral and nasal membranes offer advantages over other routes of administration. For example, nucleic acids administered through these membranes may have a rapid onset of action, provide therapeutic plasma levels, avoid first pass effect of hepatic metabolism, and avoid exposure of the nucleic acids to the hostile gastrointestinal (GI) environment. Additional advantages include easy access to the membrane sites so that the nucleic acid can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many agents. Further, the sublingual mucosa is convenient, acceptable and easily accessible.

A pharmaceutical composition of CIF or CIR nucleic acid may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Compositions for oral administration include powders or granules, suspensions or solutions in water, syrups, slurries, emulsions, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Parenteral administration includes intravenous drip, subcutaneous, intraperitoneal or intramuscular injection, intrathecal or intraventricular administration. In some embodiments, parental administration involves administration directly to the site of disease (e.g. injection into a heart).

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Pulmonary delivery compositions can be delivered by inhalation by the patient of a dispersion so that the composition, preferably CIF or CIR nucleic acids, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver agents that may be readily formulated as dry powders. A CIF or CIR nucleic acid composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, arm, or leg.

Tissue, e.g., cells or organs can be treated with a CIF or CIR nucleic acid, ex vivo and then administered or implanted in a subject. The tissue can be autologous, allogeneic, or xenogeneic tissue. e.g., tissue can be treated to reduce graft v. host disease.

In one aspect, the invention features a method of administering a CIF or CIR nucleic acid (e.g., as a compound or as a component of a composition) to a subject (e.g., a human subject). In some embodiments, the methods involve administering a compound, as disclosed herein, in a unit dose to a subject. In one embodiment, the unit dose is between about 10 mg and 25 mg per kg of bodyweight. In one embodiment, the unit dose is between about 1 mg and 100 mg per kg of bodyweight. In one embodiment, the unit dose is between about 0.1 mg and 500 mg per kg of bodyweight. In some embodiments, the unit dose is more than 0.001, 0.005, 0.01, 0.05, 0.1, 0.5, 1, 2, 5, 10, 25, 50 or 100 mg per kg of bodyweight.

The defined amount can be an amount effective to treat or prevent a disease or disorder, e.g., a disease or disorder associated with the heart. The unit dose, for example, can be administered by injection (e.g., intravenous or intramuscular), an inhaled dose, or an application by a device.

In some embodiments, the unit dose is administered daily. In some embodiments, less frequently than once a day, e.g., less than every 2, 4, 8 or 30 days. In another embodiment, the unit dose is not administered with a frequency (e.g., not a regular frequency). For example, the unit dose may be administered a single time. In some embodiments, the unit dose is administered more than once a day, e.g., once an hour, two hours, four hours, eight hours, twelve hours, etc.

In one embodiment, a subject is administered an initial dose and one or more maintenance doses of a CIF or CIR nucleic acid. The maintenance dose or doses are generally lower than the initial dose, e.g., one-half less of the initial dose. A maintenance regimen can include treating the subject with a dose or doses ranging from 0.0001 to 100 mg/kg of body weight per day, e.g., 100, 10, 1, 0.1, 0.01, 0.001, or 0.0001 mg per kg of bodyweight per day. The maintenance doses may be administered no more than once every 1, 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the nucleic acid may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Following successful treatment, it may be desirable to have the patient undergo maintenance therapy to prevent the recurrence of the disease state, wherein the compound of the invention is administered in maintenance doses, ranging from 0.0001 mg to 100 mg per kg of body weight.

The concentration of the CIF or CIR nucleic acid composition is an amount sufficient to be effective in treating or preventing a disorder or to regulate a physiological condition in humans. The concentration or amount of CIF or CIR nucleic acid administered will depend on the parameters determined for the agent and the method of administration. Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a CIF or CIR nucleic acid can include a single treatment or, preferably, can include a series of treatments. It will also be appreciated that the effective dosage of a CIF or CIR nucleic acid used for treatment may increase or decrease over the course of a particular treatment. For example, the subject can be monitored after administering a CIF or CIR nucleic acid composition. Based on information from the monitoring, an additional amount of the CIF or CIR nucleic acid composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of heart function. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models.

Administration can be provided by the subject or by another person, e.g., a health care provider. The composition can be provided in measured doses or in a dispenser which delivers a metered dose.

The CIF and CIR nucleic acids may be stabilized or have modified nucleotides in some embodiments. Typically the CIR is an RNA molecule made up completely of ribonucleotides. In some instances however the CIR may be mixed. For example, in some embodiments, the nucleic acids may comprise at least one ribonucleotide, at least one deoxyribonucleotide, and/or at least one bridged nucleotide. In some embodiments, the nucleic acid may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the nucleic acid comprises a nucleotide analog disclosed in one of the following United States Patent or Patent Application Publications: U.S. Pat. Nos. 7,399,845, 7,741,457, 8,022,193, 7,569,686, 7,335,765, 7,314,923, 7,335,765, and 7,816,333, US 20110009471, the entire contents of each of which are incorporated herein by reference for all purposes. The nucleic acid may have one or more 2' O-methyl nucleotides. The nucleic acid may consist entirely of 2' O-methyl nucleotides.

The nucleic acid may be of up to 500 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the nucleic acid are nucleotide analogues. The nucleic acid may be of 8 to 30 nucleotides in length in which 2 to 10, 2 to 15, 2 to 16, 2 to 17, 2 to 18, 2 to 19, 2 to 20, 2 to 25, 2 to 30 nucleotides of the nucleic acid are nucleotide analogues.

The nucleic acid may be of 30 to 50 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the nucleic acid are nucleotide analogues. Optionally, the nucleic acids may have every nucleotide except 1, 2, 3, 4, 5, 6, 7, 8, 9, or 10 nucleotides modified.

The nucleic acid may consist entirely of bridged nucleotides (e.g., LNA nucleotides, cEt nucleotides, ENA nucleotides). The nucleic acid may comprise alternating deoxyribonucleotides and 2'-fluoro-deoxyribonucleotides. The nucleic acid may comprise alternating deoxyribonucleotides and 2'-O-methyl nucleotides. The nucleic acid may comprise alternating deoxyribonucleotides and ENA nucleotide analogues. The nucleic acid may comprise alternating deoxyribonucleotides and LNA nucleotides. The nucleic acid may comprise alternating LNA nucleotides and 2'-O-methyl nucleotides. The nucleic acid may have a 5' nucleotide that is a bridged nucleotide (e.g., a LNA nucleotide, cEt nucleotide, ENA nucleotide). The nucleic acid may have a 5' nucleotide that is a deoxyribonucleotide.

The nucleic acid may comprise deoxyribonucleotides flanked by at least one bridged nucleotide (e.g., a LNA nucleotide, cEt nucleotide, ENA nucleotide) on each of the 5' and 3' ends of the deoxyribonucleotides. The nucleic acid may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the nucleic acid may have a 3' hydroxyl group. The 3' position of the nucleic acid may have a 3' thiophosphate.

The nucleic acid may be conjugated with a label. For example, the nucleic acid may be conjugated with a biotin moiety, cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

Preferably the CIF or CIR nucleic acid comprises one or more modifications comprising: a modified sugar moiety, and/or a modified internucleoside linkage, and/or a modified nucleotide and/or combinations thereof. It is not necessary for all positions in a given nucleic acid to be uniformly modified, and in fact more than one of the modifications described herein may be incorporated in a single nucleic acid or even at within a single nucleoside within a nucleic acid.

In some embodiments, the CIF or CIR nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into nucleic acids.

Modified nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified nucleic acids are also known that include nucleic acids that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified nucleic acid is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked nucleic acids and the 5' position of 5' terminal nucleotide.

CIF or CIR nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions.

It is not necessary for all positions in a given nucleic acid to be uniformly modified, and in fact more than one of the modifications described herein may be incorporated in a single nucleic acid or even at within a single nucleoside within an nucleic acid.

CIF or CIR nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. Nos. 3,687,808, as well as 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the CIF or CIR nucleic acids are chemically linked to one or more moieties or conjugates that enhance the activity, cellular distribution, or cellular uptake of the nucleic acid. For example, one or more CIF or CIR nucleic acids, of the same or different types, can be conjugated to each other; or CIF or CIR nucleic acids can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, the CIF or CIR nucleic acid comprises phosphorothioate internucleotide linkages. In some embodiments, the CIF or CIR nucleic acid comprises phosphorothioate internucleotide linkages between at least two nucleotides. In some embodiments, the CIF or CIR nucleic acid comprises phosphorothioate internucleotide linkages between all nucleotides. It should be appreciated that the CIF or CIR nucleic acid can have any combination of modifications as described herein.

In certain aspects of the invention, kits are provided, comprising a container housing a composition comprising a nucleic acid of the invention. In some embodiments, the kits comprise a container housing a nucleic acid of a CIF and/or a CIR. In some embodiments, the kit has a pharmaceutical composition comprising a CIF or CIR nucleic acid and a pharmaceutically acceptable carrier. In some embodiments, the individual components of the pharmaceutical composition may be provided in one container. Alternatively, it may be desirable to provide the components of the pharmaceutical composition separately in two or more containers, e.g., one container for CIF or CIR nucleic acids, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1: Bioassays with RNA Treatment (CIR 1)

Methods: Cloning:

For cloning, a total of 2 μg of human fetal heart RNA (Agilent Technologies, Inc #540165, Santa Clara, Calif., USA) was used for each reaction. The CloneMiner™ II cDNA Library Construction Kit (Invitrogen, #A11180) was used to create individual clones. First and second DNA strands were synthesized from template RNAs and ligated into the pDONR222 vector. The pDONR222 vector contains a kanamycin resistance gene which allows for selection of transfected bacteria and the ccdB gene which interferes with *E. coli* DNA gyrase allowing for negative selection of the donor vector in *E. coli* following recombination and transformation. The ElectroMAX™ DH10B™ T1 Phage Resistant *E. coli* strain provided with the kit was transformed using the EC 1000 Electroporator (Thermo ES) at 2800V. To each sterile cuvette, 50 μl of ElectroMAX™ DH10B cells, 1.5 μl of (150 ng/μl) vector plus insert and 50 μl of dH2O were added. If the samples arced at this voltage setting, 100 μl of dH2O, or more, were added to increase electrical resistance. After electroporation, the samples were added to 1 ml of S.O.C. medium and cultured in 15 ml snap-cap tubes for at least 1 hour at 37° C. on a shaker at 225-250 rpm to allow for expression of the kanamycin resistance gene. Serial dilutions of sample aliquots with S.O.C. medium at the ratios 1:10, 1:100 and 1:1000 were plated on LB agar plates containing 50 ug/ml of kanamycin. The remaining cells were frozen at −80° C. Plated cells were incubated overnight at 37° C. Individual colonies containing vector with cloned genes (over 400 genes from fetal human heart and 400 genes from adult heart) were collected and transferred into snap-cap tubes with 2 ml of 2×YT medium containing 50 ug/ml of kanamycin and incubated overnight at 37° C. on a shaker at 225-250 rpm. Plasmids with clones were extracted according to the standard Miniprep Plasmid DNA Isolation Protocol found in the online archive of the Institute of Bioinformatics and Applied Biotechnology.

BsrGI Digestion:

Extracted plasmids (5 μl sample) were digested with 20U (1U/μl) BsrGI enzyme in 1×NE Buffer and 0.1 mg/μl of BSA. The digest mixtures were incubated for 1 h at 37° C. and analyzed by 1% agarose gel electrophoresis containing 0.5 μg/ml of ethidium bromide.

PCR:

The T7 RNA polymerase binding site was added to the 5' end of the forward and reverse M13 primers indicated below as underlined (SEQ ID NOs. 5 and 6)

```
Forward primer:
5'-TAATACGACTCACTATAGGGGTAAAACGACGGCCAG-3'

Reverse primer
5'-TAATACGACTCACTATAGGGCAGGAAACAGCTATGAC-3'
```

PCR was performed using a MyTaq™ Red Mix kit (Bioline, BIO-25043, Taunton, Mass., USA) including polymerase and dNTP plus the above primers and DNA templates. The reaction included denaturation at 95° C. for 15 sec followed by annealing at 55° C. for 15 sec and elongation at 72° C. for 15 sec for 30 cycles. The resulting DNA was purified by 5M sodium chloride salt and isopropanol precipitation. Pellets were washed with 70% ethanol and re-suspended in 1× Tris-EDTA buffer.

RNA Synthesis:

The transcription reaction mixture was assembled from the MAXIscript® T7 Kit, (Ambion # AM1314M, Grand Island, N.Y., USA). We added 1 μg of PCR product DNA, 2 μL of 10× transcription buffer, 2 μL of T7 Enzyme Mix and 1 μL of each (10 mM) dNTP, and adjusted the volume to 20 μL with nuclease-free water. The reaction mixture was incubated at 37° C. for 2 hours. RNA was purified using ammonium acetate and ethanol precipitation and resuspended in nuclease-free water. The concentration of RNA was determined spectrophotometrically at 260 nm using a Synergy HT (Bio-Tek, Winooski, Vt., USA) plate reader.

qRT-PCR:

RNA was extracted using a NucleoSpin RNAII Kit (Macherey-Nagel, Bethlehem, Pa., USA) from differentiated cells treated with the active RNA, and one control untreated (treated only with lipofectamine). qRT-PCR was performed with a Rotor-Gene machine using a Rotor-Gene SYBR PCR kit (Qiagen #204074, Valencia, Calif., USA) with primers as designed in our earlier studies (Zhang et al., 2009).

Bioassay:

Cardiac mutant non-function carrier (+/c) adult axolotls were bred in our colony at Texas A&M University-Commerce or purchased from the *Ambystoma* Genetic Stock Center, University of Kentucky, Lexington. These heterozygous adult animals were mated (+/c x +/c) to produce mutant (c/c) and wildtype (+/+; +/c) embryos for our studies. Embryos were collected and allowed to develop to heartbeat stages 35-36, according to the staging series of Bordzilovskaya et al, (1989). For bioassays, only double recessive mutant c/c embryos were selected which do not have beating hearts. The embryos were anaesthetized by 0.7 mg/ml tricainemethanesulfonate or MS-222 (Argeitt Chemicals Labs) in Holtfreter's solution (Lemanski et al, 1996). Embryos were dissected under a binocular dissecting microscope in modeling clay-lined Petri dishes in Holtfreter's medium containing 1% antibiotic/antimycotic (Gibco #15240). Hearts were transferred into the Petri dishes on Parafilm substrate into 50 μl of Holtfreter's solution (without antibiotic) containing 7 ng/μl of human fetal heart RNA from individual clones along with 0.1 mg/ml of lipofectamine reagent (Invitrogen, Carlsbad Calif.) and cultured as organ culture up to 5 days. The Petri dishes with hearts were enclosed in a plastic container containing wet paper towels to maintain a saturated humid environment at 17° C.

Results:

A cDNA library was generated from total human fetal heart RNA purchased from Agilent Technologies Inc (Santa Clara, Calif.). 400 individual RNAs from human fetal heart using the pDONR222 plasmid as a vector were randomly cloned. DNA clones were synthesized by PCR using the vectors as templates and M13 primers. The PCR products were visualized through agarose gel electrophoresis and ethidium bromide staining. A vast majority of clones showed unique DNA bands indicating the presence of specific DNA inserts in the plasmids. Then, RNAs were synthesized by using an in vitro transcription reaction.

Figure 3C:
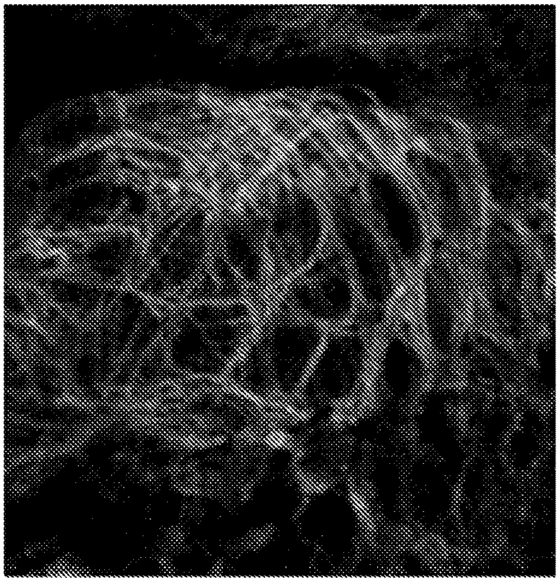
FIG. 3 shows tropomyosin expression revealed by immunochemical staining followed by confocal imaging.
FIG. 3A shows normal heart, 3B mutant non-treated heart and 3C mutant heart after transfection with active CIR 1 (active clone #6).

RNA clones along with 0.1 mg/ml of lipofectamine transfection reagent were diluted to a concentration of 7 ng/μl in Holtfreter's solution containing a physiological mixture of salts required for cardiomyocyte contraction. The hearts were incubated for transfection with RNAs for various time periods from 1 to 5 days in a plastic container at saturated humidity and room temperature. Each individual clone was tested on three hearts. Transfection with RNA derived from CIR 1 was found to induce mutant hearts to beat. Initially, the treated hearts beat sporadically. However, with additional time in organ culture, the beating became more vigorous and regular. Hearts were visualized using laser confocal microscopy after fixation in paraformaldehyde and staining with monoclonal anti-tropomyosin and fluorescently-labeled secondary antibodies. Confocal microscopy revealed tropomyosin expression in a normal heart. Mutant axolotl hearts not treated with active RNA (only lipofectin) or treated with RNA derived from other non-active clones, did not show tropomyosin expression, myofibril formation and beating (negative control). After transfection with active CIR 1, mutant hearts showed tropomyosin expression (FIG. 3).

Example 2: Fixation and Staining Procedure of Tropomyosin Time Course Experiment on Normal and Mutant Hearts Methods: Fixation and Staining Procedure:

All steps were performed at room temperature as previously described (Zhang et al, 2003). Samples (hearts or slide glasses with cell culture) were fixed in 4% paraformaldehyde for 30 min and rinsed twice in PBS for 3 min. Hearts were permeabilized in 0.05% Tween-20 and 3% BSA in PBS for 1 h. Hearts were incubated overnight with monoclonal anti-tropomyosin CG3 antibody (Developmental Studies Hybridoma Bank, University of Iowa) diluted to 1:75 in PBS, and then washed several times in PBS. Hearts were incubated in FITC conjugated goat anti-mouse polyclonal secondary antibody (Abcam, # ab6669) at a 1:75 dilution for 1 h. The hearts were rinsed in several changes of PBS and mounted on slides in SlowFade® Gold antifade reagent (Invitrogen, #S36936). Three layers of fingernail polish were applied to the peripheral surfaces of the glass coverslips to elevate them when positioned on the glass slides and thus preventing damage to the whole heart preparations. Secondary antibodies conjugated with FITC were excited at 488 nm with an emission at 520 nm. The stained heart samples were scanned under a laser confocal microscope (Olympus Fluoview) equipped with a computer to record the images.

Figure 4A:
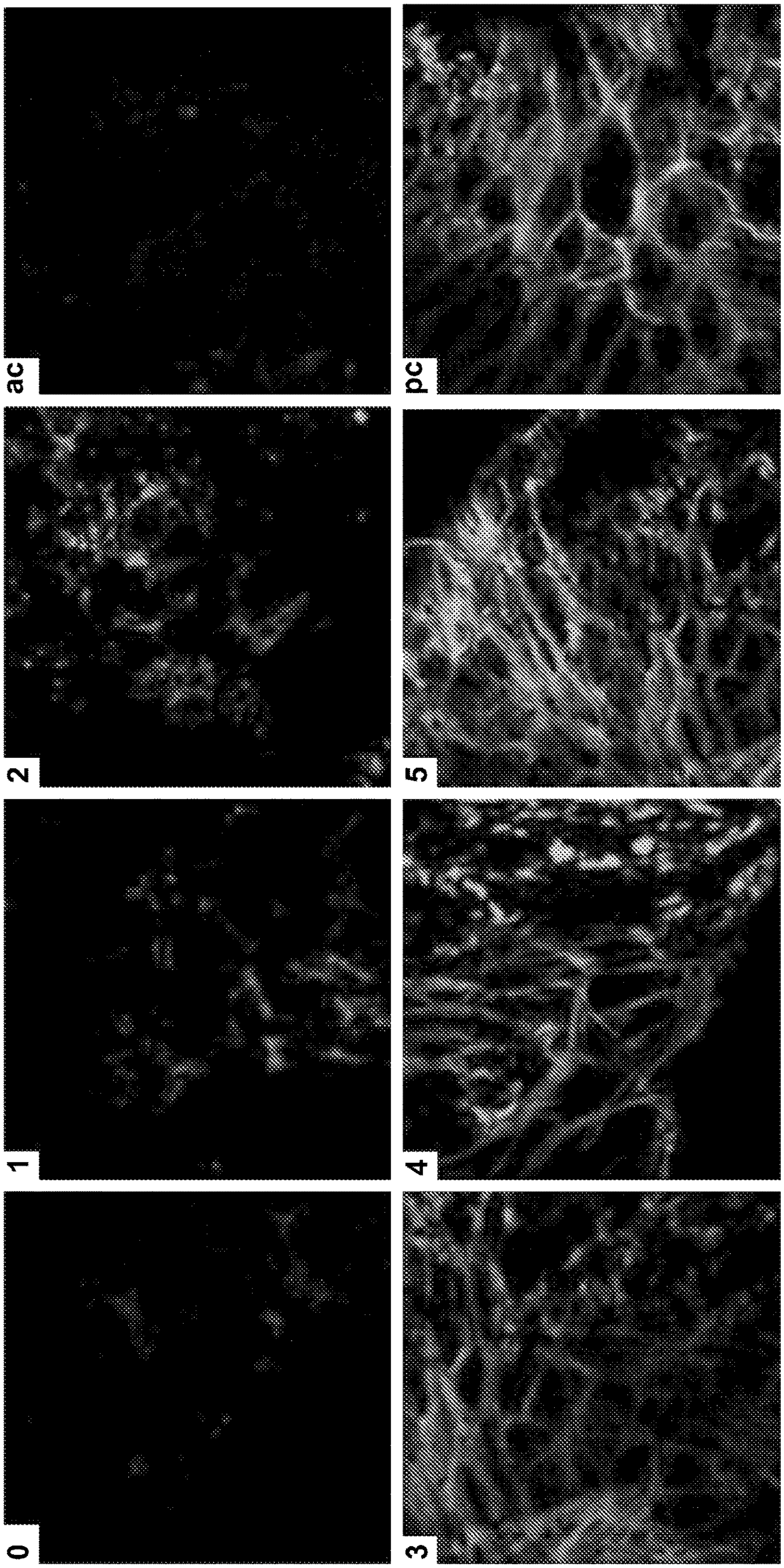
FIG. 4 is a time-course study of the relative quantities of tropomyosin expression by immunofluorescent staining in RNA-treated axolotl hearts. Immunofluorescent images show mutant hearts fixed and stained for tropomyosin after incubation with 7 ng/μl of CIR 1 for 1, 2, 3, 4 and 5 days; Time 0 is a negative control with lipofectamine treatment without RNA; pc is a positive control of normal heart without treatment; ac is a secondary antibody only staining control to test for nonspecific staining (4A). Average levels of fluorescence were quantified with ImageJ software as a percentage of that expressed in normal hearts, which was set to 100% (4B). *P-value among those hearts treated on the second day and following days as well as untreated mutant hearts is $p<0.05$, $n=5$.
Figure 4B:
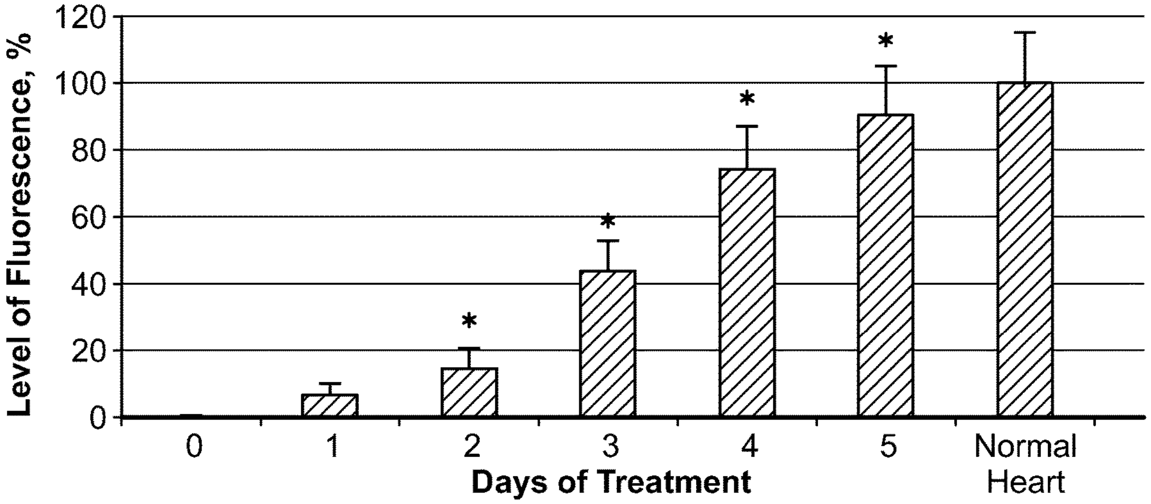

Results:

The hearts from mutant axolotl embryos were incubated with CIR 1 RNA for varying periods of time: 1, 2, 3, 4 and 5 days. Embryos at the time of dissection were at post-heartbeat stage 36-37. Negative controls at time 0 consisted of—negative control with lipofectamine treatment without RNA, pc—positive control of normal heart without treatment, and ac—secondary antibody only staining control to test for nonspecific staining (FIG. 4). In negative controls, mutant hearts not transfected with RNA do not show tropomyosin staining nor do hearts stained only with the secondary antibodies. After incubation with RNA, the experimental hearts were fixed and stained with anti-tropomyosin and FITC conjugated secondary antibodies and viewed by laser confocal microscopy (FIG. 4A). Fluorescence levels of heart images were quantified with ImageJ software (National Institutes of Health) (FIG. 4B). During the five days of incubation, tropomyosin expression gradually increases. Starting with the second day and subsequently thereafter, statistically significant differences in tropomyosin expression between treated hearts and untreated hearts were observed ($p<0.05$, $n=5$). Also, during the time increment of incubation, the numbers of striated myofibrils increased significantly. Striated myofibrils were prominent by the 3rd day of RNA treatment in mutant hearts in organ culture, as well as in normal hearts without RNA transfection. Untreated control mutant hearts showed no significant increases in tropomyosin staining.

Example 3: CIR 1 qRT-PCR

Methods:

Normal and mutant embryonic hearts at stages 36-37 were placed into 100 μl droplet cultures of Holtfreter's solution containing antibiotics (Zhang et al, 2009). Mutant hearts were placed in droplets containing 7 ng/μl of RNA derived from CIR 1 and incubated at 14° C. for 72 hours. Each treatment group consisted of 10 hearts. RNA was extracted using a NucleoSpin RNAII Kit (Macherey-Nagel, Bethlehem, Pa., USA) from ten mutant hearts treated with the active CIR 1 human RNA, from 10 untreated (treated only with lipofectamine) hearts as a control, and from ten normal hearts. qRT-PCR was performed with a Rotor-Gene machine using a Rotor-Gene SYBR PCR kit (Qiagen #204074, Valencia, Calif., USA) with primers as reported in Zhang et al, 2009. Expression in normal hearts was assigned a value of 100%. Primers used for genes in real time RT-PCR experiments can be found in Table 1 below (SEQ ID NOs. 7 through 14):

TABLE 1

| Gene of interest: | Forward/ Reverse: | Primer: |
|---|---|---|
| Tropomyosin | Forward | 5'-ggagcttgaccatgcgctgaa |
| Tropomyosin | Reverse | 5'-tgagaaccgacacaaagcaagagg |
| troponin T | Forward | 5'-ccaagggcttcaccgggctcaa |
| troponin T | Reverse | 5'-tggcagaggtggaatggatcacagg |
| α-syntrophin | Forward | 5'-ggactctccaccgcctccctctc |
| α-syntrophin | Reverse | 5'-ccccgcttcatccttcgctctga |
| β-actin | Forward | 5'-tccatgaaggctgcccaact |
| β-actin | Reverse | 5'-tggcgccacatctgattgat |

Figure 5A:
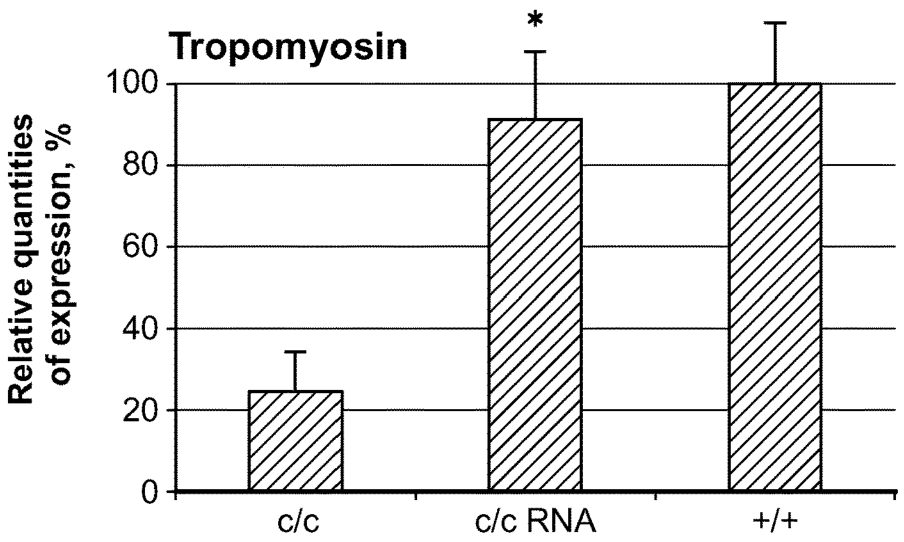
FIG. 5 shows relative expression of cardiac markers by RT-PCR in mutant hearts (c/c). Mutant hearts (c/c), mutant hearts transfected with the active CIR 1 RNA, and normal hearts (+/+) are compared: (5A) tropomyosin, (5B) cardiac Troponin T and (5C) α-syntrophin. Expression was calculated as the percentage of that expressed in normal hearts (expression in normal hearts was assumed to be 100%). Statistical significances (p) for: tropomyosin, $p<0.03$, cardiac troponin T, $p<0.04$ and α-syntrophin, $p<0.05$, $n=10$.
Figure 5B:
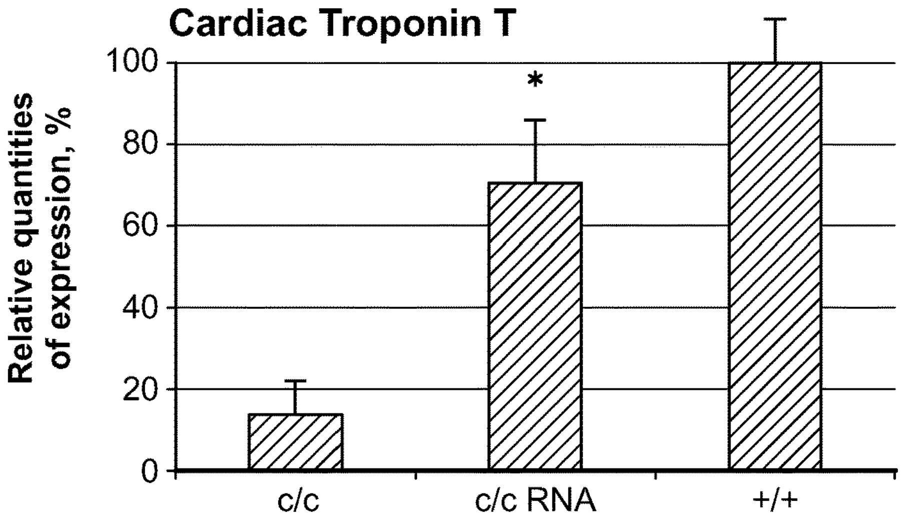
Figure 5C:
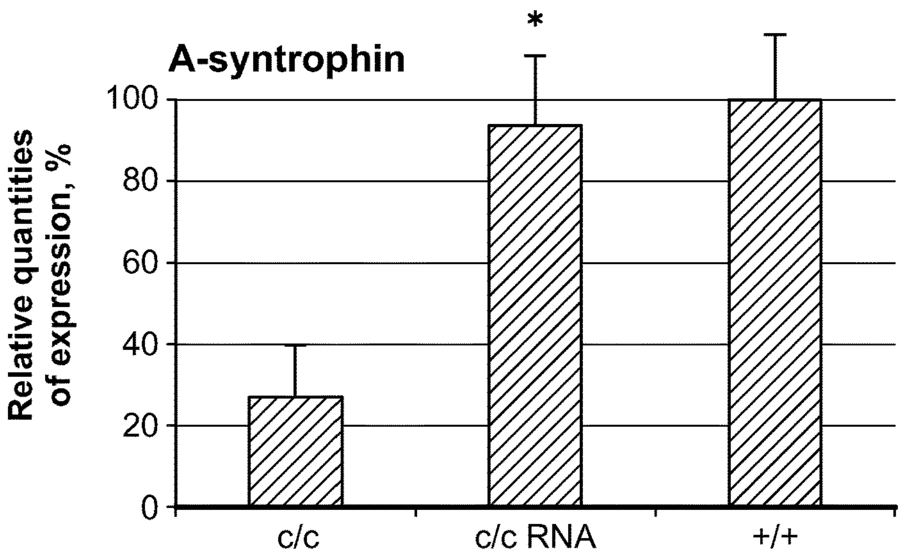

Results:

RNA was extracted from ten mutant hearts treated with CIR 1 human RNA, from 10 untreated (treated only with lipofectamine) mutant hearts as controls, and from ten normal hearts. Expression of genes considered as cardiac markers included: tropomyosin, cardiac troponin T and α-syntrophin, all of which increased significantly in comparison to β-actin in the RNA-treated hearts (FIG. 5, A-C). Expression was calculated as % expression relative to normal hearts, which was assumed to be 100%. In mutant hearts, expression of cardiac markers was much lower than in normal hearts, as low as 10-20%. After treatment with the active CIR 1 derived RNA (7 ng/μl), expression in mutant hearts increased significantly up to 70-90%: tropomyosin—75%, cardiac Troponin T–70% and α-syntrophin—90% after only 5 days in organ culture.

Figure 6B:
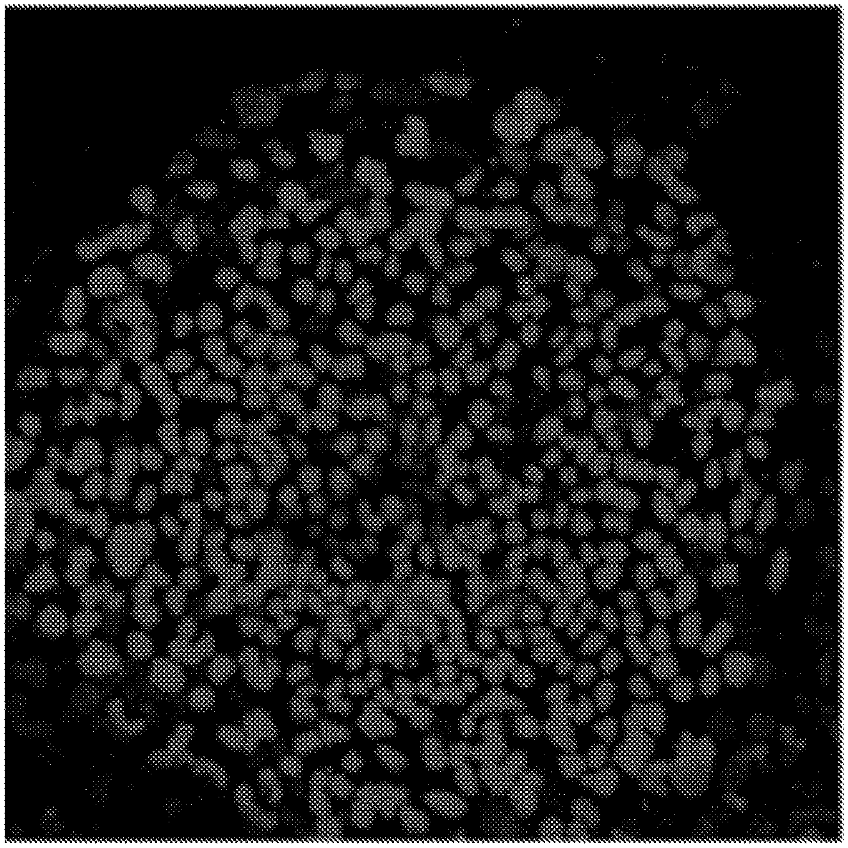
FIG. 6 shows immunochemical staining with antibodies for marker pluripotency Oct-3/4(6B). Oct-3/4 is nuclear factor localized in nuclei. It also shows nuclei staining with DAPI (6A). A majority of cells were observed to express the factor of pluripotency Oct-3/4 (FIG. 6B) which co-localized in cell nuclei stained with DAPI (FIG. 6A).
Figure 22B:
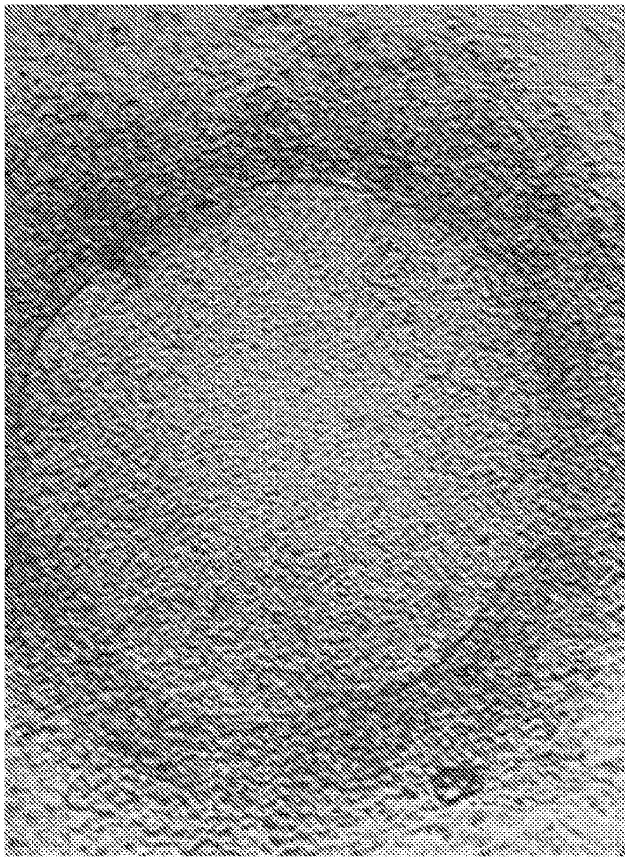
FIG. 22 shows non-differentiated colonies of human iPSCs (FIG. 22A) and mouse ESCs (FIG. 22B).
Figure 22A:
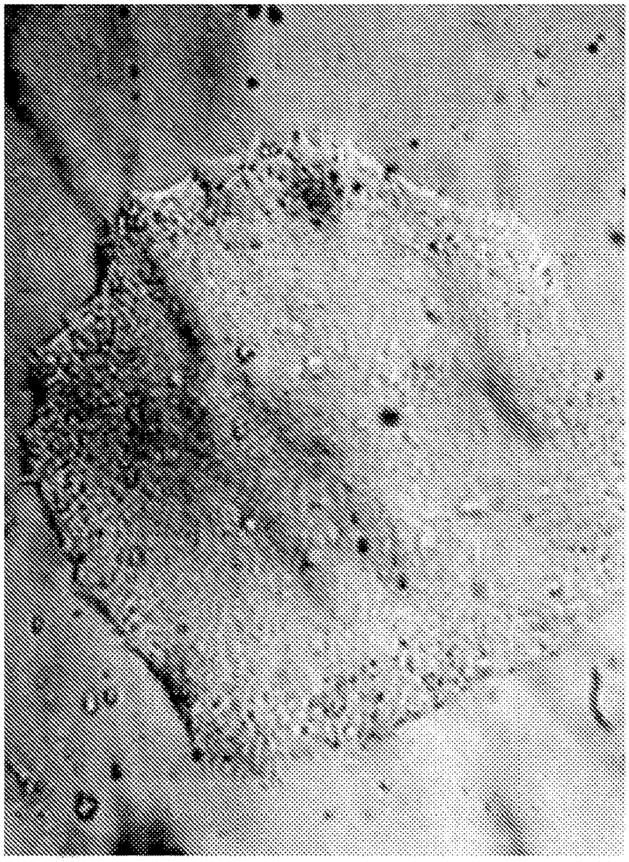
Figures 23A, 23B, 23C, 23D:
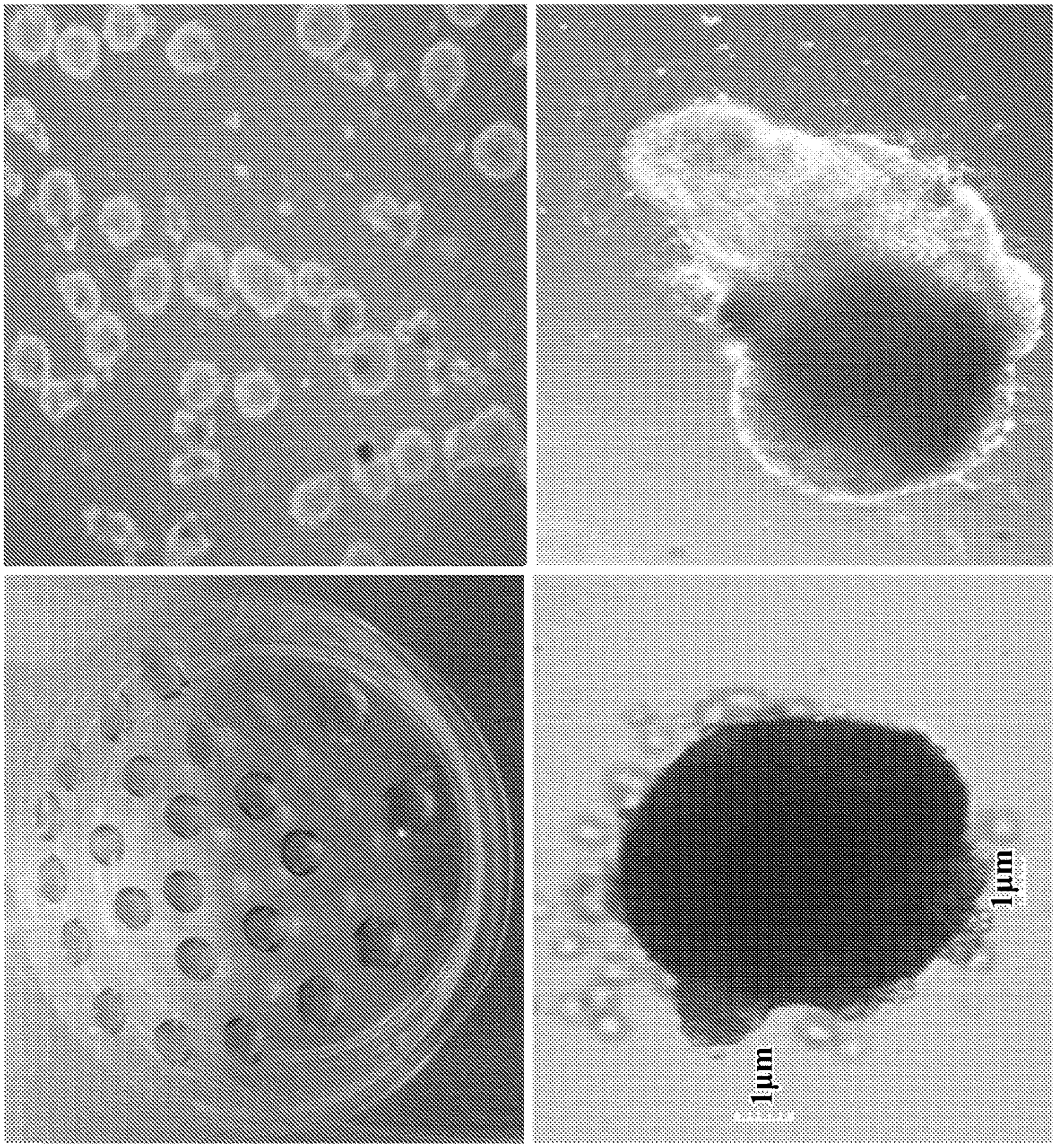
FIG. 23A is a photograph showing plated stem cells in hanging drops.
FIG. 23B is two days later, showing the formation of clumps (embryoid bodies) in suspension.
FIG. 23C is a high magnification image of embryoid bodies.
FIG. 23D shows the attachment and spreading cells on plate during days 4-5.

Example 4: Stem Cell Differentiation by Active Clones of RNA into Cardiomyocytes Methods: Stem Cell Culture and Differentiation Protocol:

Human induced pluripotent stem cells (iPSCs), DF19-9-11T.H, from WiCell, Inc., (Madison, WIIS., USA) and mouse Embryonic Stem Cells (mESCs), Strain 129, OriCell from Cyagen Biosciences, Inc. (Santa Clara, Calif., USA) were incubated and grown at 37° C. and 5% $CO_2$(FIGS. 22A, 22B), and passaged routinely according to our routine protocols (Lemanski et al., 2012). These cells express the Oct-3/4 pluripotency factor (FIG. 6A) colocalized in the nuclei as shown with DAPI staining (FIG. 6B). To generate embryonal bodies, small drops of cell suspensions of 20 μL volume were placed by micropipette on the inner surface of a Petri dish lid and cultured for 24 h. On the second day, the cells were clumped in embryonal bodies (EBs) (FIGS. 23B, 23C). EBs were washed by medium and transferred to gelatin-coated dishes. In a few days EBs attached to the surface and cells started to proliferate and spread (FIG. 23D). To induce differentiation, cells were transfected by active clones of RNA mixed with transfection reagent, Lipofectamine RNAiMAX, (Life Technologies, Grand Island, N.Y., USA), diluted to a concentration of 50 ng/μl in OPTI-MEM medium (Life Technologies) and incubated for 6 hours.

Results:

Mouse embryonic stem cells (mESCs) and human induced pluripotent stem cells (iPSCs) were cultured according to protocols and their pluripotency was tested by immunochemical staining with Oct-3/4 antibodies (FIG. 6).

Figure 7:
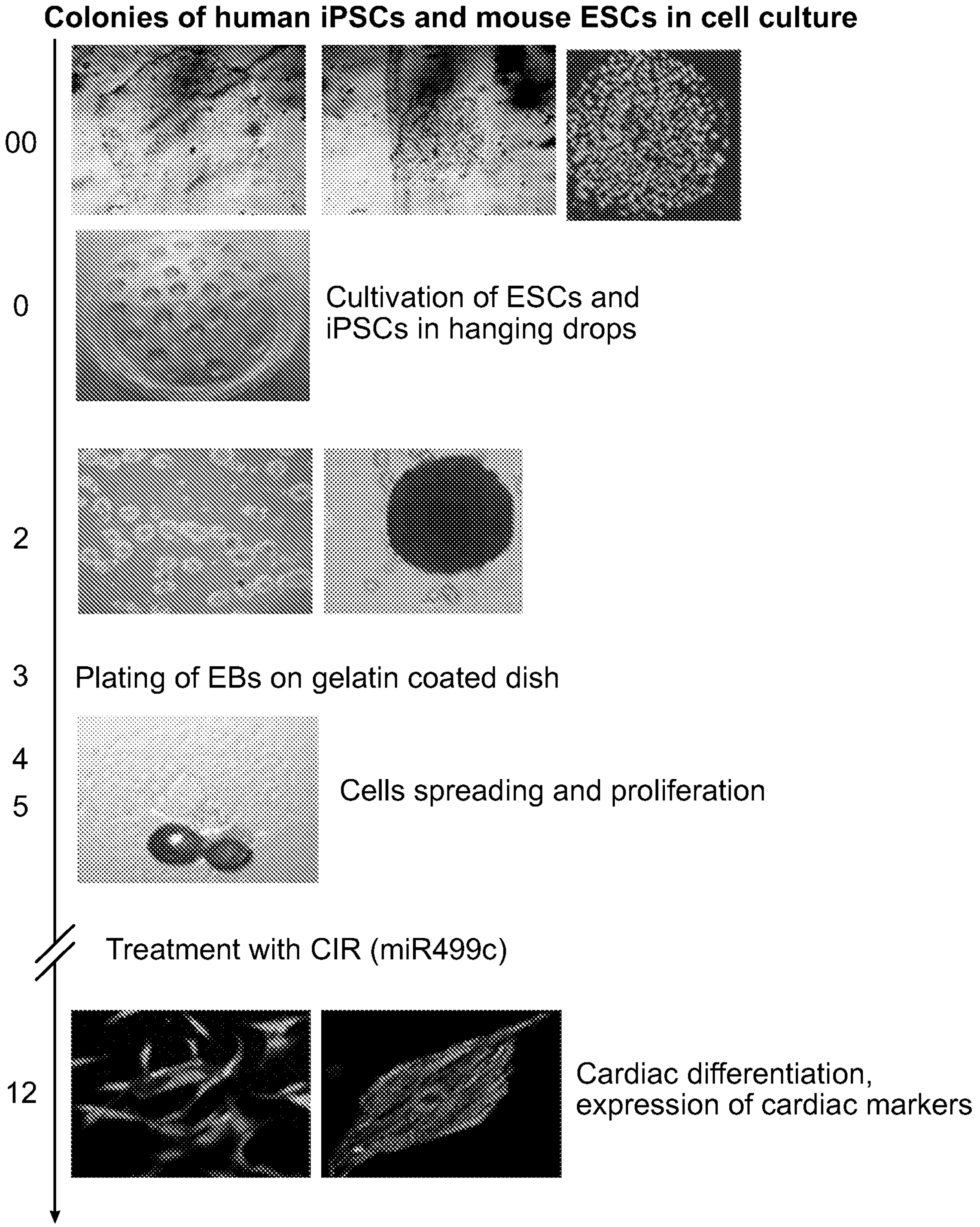
FIG. 7 is a timeline showing differentiation stages. Day 00: iPSCs and ESCs are cultured. Day 0: Stem cells are passaged and plated in hanging drops. Day 2: Embryoid bodies are formed. Day 3: EBs on gelatin coated dishes are plated. Days 4-5: Cells are spread and proliferate from EBs. Day 5: Treatment with cardiogenic-inducing RNA. Day 12: Cells differentiate to cardiomyocytes.
Figure 8B:
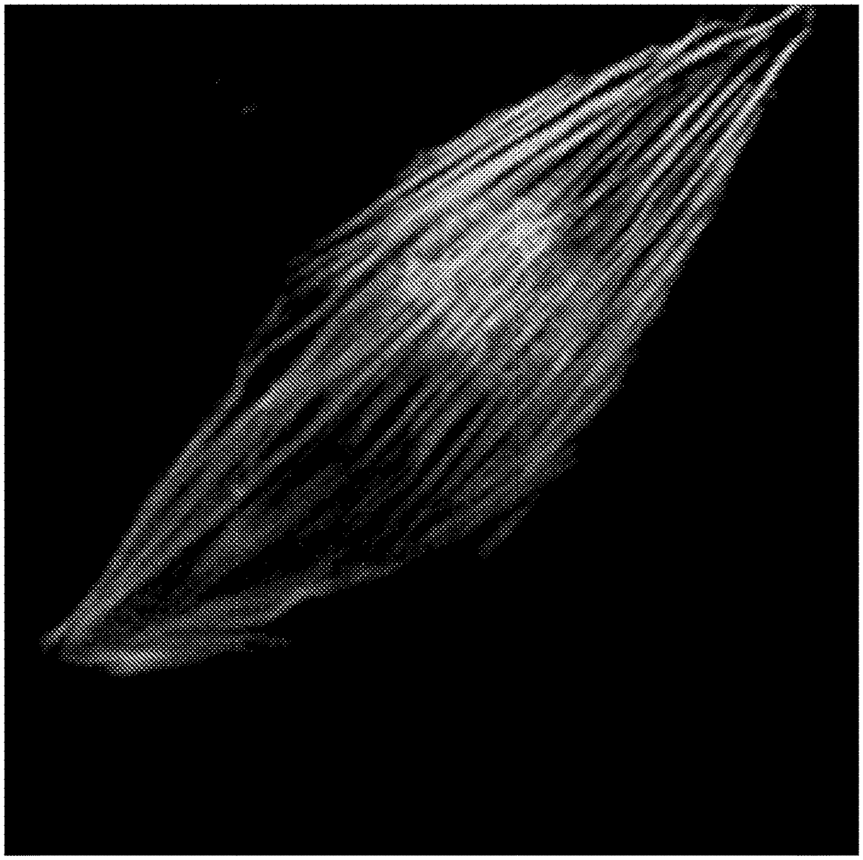
FIG. 8 shows confocal imaging of stem cell-derived cardiomyocytes stained with cardiac troponin T: 8A shows human iPSCs-derived cardiomyocytes treated with active CIR 1 and 8B shows mESC-derived cardiomyocytes treated with CIR 1.
Figure 8A:
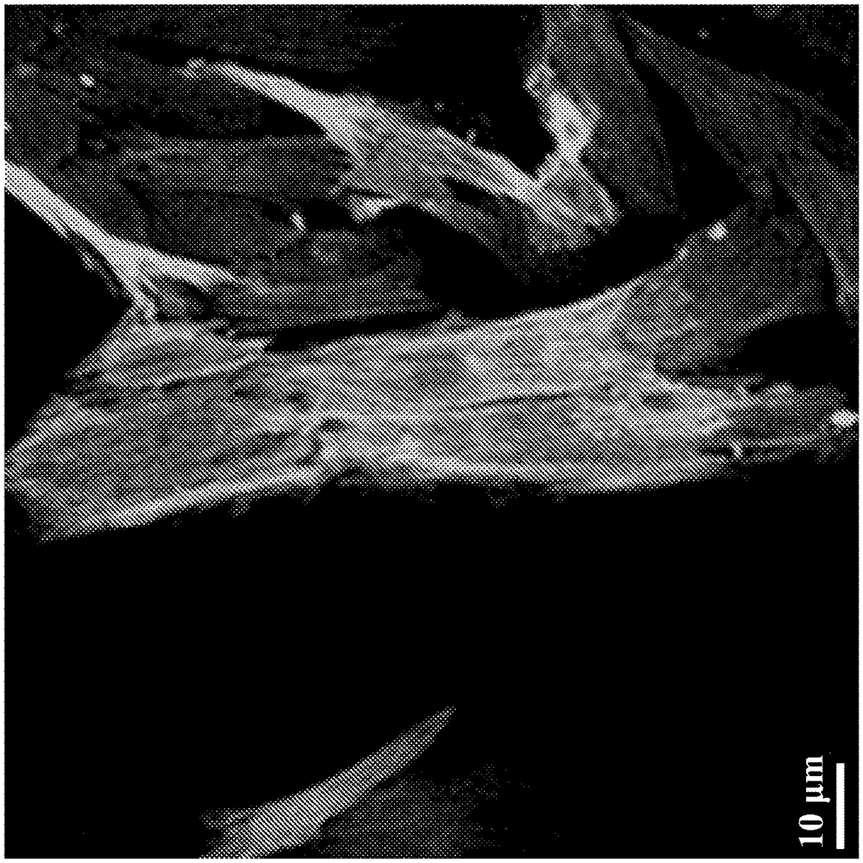

Spontaneous cardiomyocyte differentiation of mouse and human embryonic stem cells was described previously by Mummery et al, 2002. In this study stem cells differentiate into cardiomyocytes after formation of cell clumps, embryoid bodies (EBs). Using Mummery's test approach, results showed spontaneous cardiomyocyte differentiation without RNA treatment was approximately 9-10%. When the differentiated approach proposed by Mummery et al. was used, (FIG. 7), it was found that transfection of cells with CIR significantly increased the output of differentiated cardiomyocytes, revealed by immunochemical staining for cardiac troponin T and by changing of cell morphology to a spindle-shaped form. Stem cells were passaged and plated into small drops as "hanging drops" on Petri dish lids and incubated two days. On the second day, stem cells aggregated and formed embryoid bodies (EBs). The EBs were plated on collagen coated dishes and allowed them to attach. Cells from EBs started to grow and proliferate. On this stage, the cells were treated with active clones of RNAs and in 7-8 days they differentiated to spindle-shaped cardiomyocytes (FIG. 8). High resolution confocal imaging revealed myofibril organization of cardiac troponin T in stem cell-derived cardiomyocytes from human iPSCs and from mouse ESCs transfected with active clone 6 (FIG. 8).

Example 5: CIR 1 and MIR Sequence Comparisons

Figure 9A:
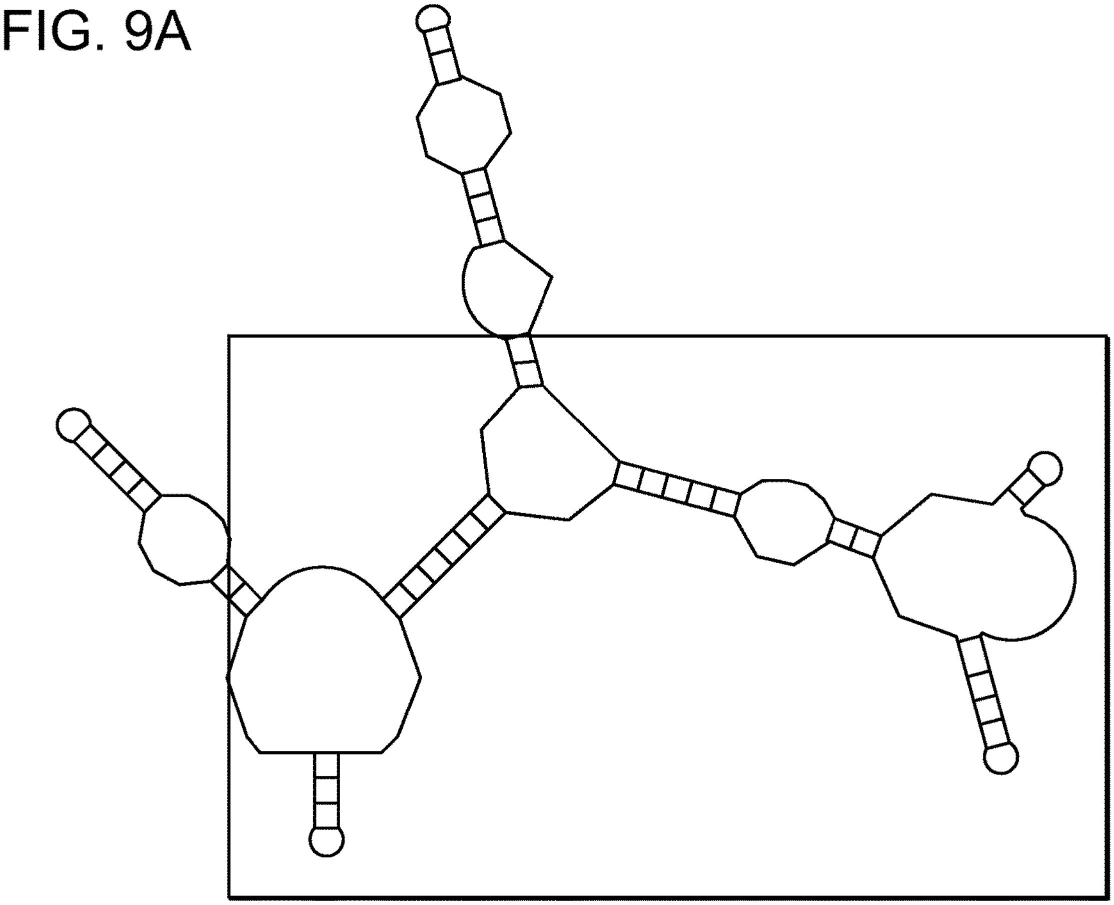
FIG. 9 shows a set of sequences. Sequences of axolotl and human CIR 1 were compared and matches in their sequences were not found, but it was noted that there were similarities in their secondary structures generated by using the online computational software GeneBee Program developed at the Belozersky Institute in Moscow, Russia. Two branches of the human RNA from CIR 1 (FIG. 9A) are structurally very similar to the axolotl RNA (FIG. 9B).
Figure 9B:
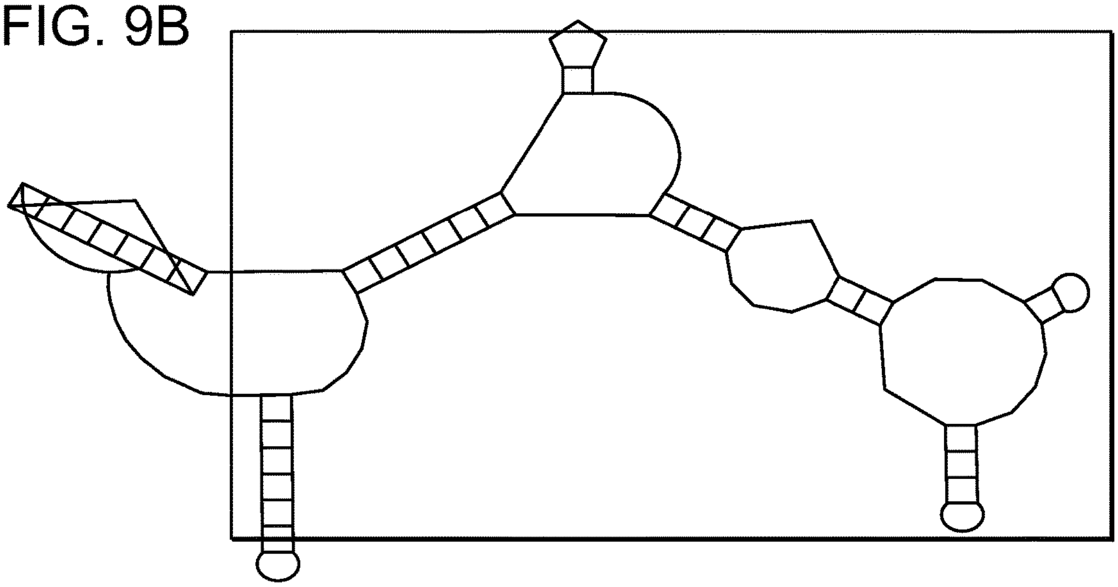
Figure 10A:
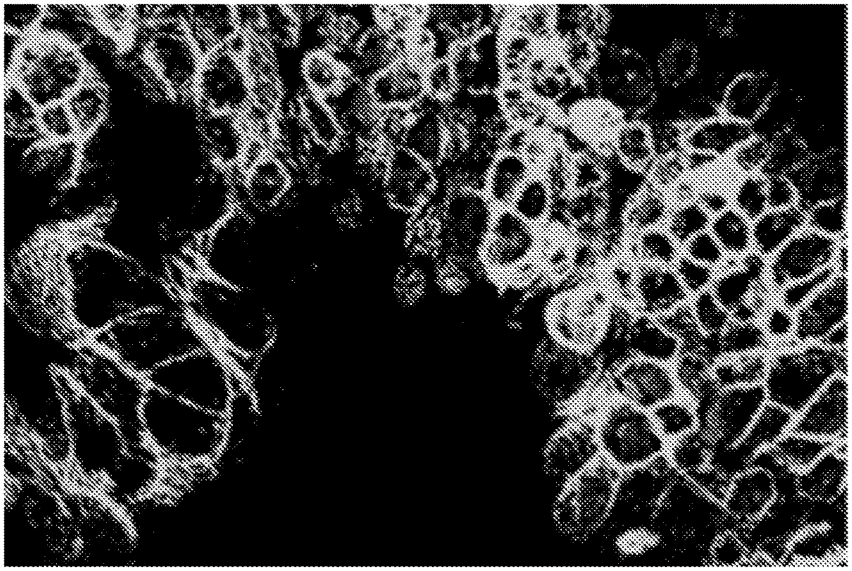
FIG. 10 is a comparison of tropomyosin present in mutant hearts, normal hearts, and mutant hearts treated by human CIR 2 fetal heart RNA using confocal laser microscopy. 10A shows normal hearts that have been fixed and stained with tropomyosin specific antibodies show staining for tropomyosin, indicating functioning cardiomyocytes at 40× magnification (×40); Part 10B shows a mutant heart without human CIR 2 fetal heart RNA treatment stained with tropomyosin specific antibodies, which illustrates a severe deficiency of tropomyosin, ×40.
FIG. 10C shows a mutant heart treated with human CIR 2 fetal heart RNA specifically stained for tropomyosin, which shows significant staining, ×40; 10D shows normal hearts after tropomyosin staining display the presence of organized sarcomeres and myofibrils, ×60; Mutant hearts treated with CIR 2 RNA and stained for tropomyosin show that the mutant tissues have been stimulated to generate well organized myofibrils in the myocardial cells and have become morphologically normal in comparison to normal hearts, ×60, are shown in 10E; 10F shows, at higher magnification, clear banding of sarcomeres is present in mutant hearts that received treatment with Human CIR 2 fetal heart RNA, ×100.
Figure 10B:
Figure 10C:
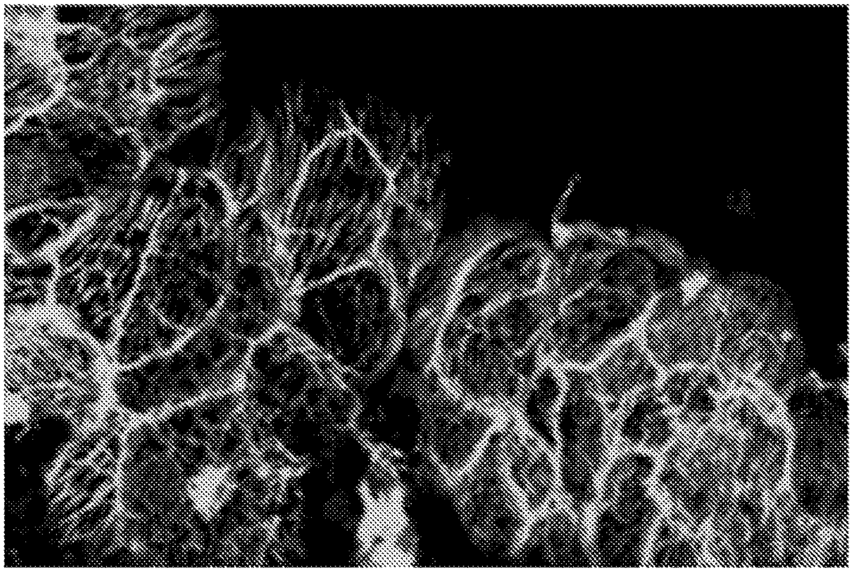
Figure 10F:
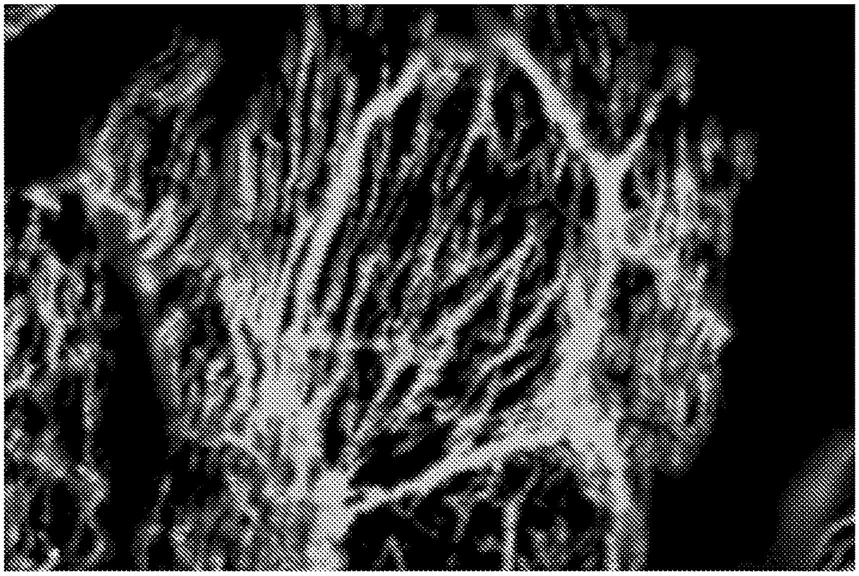
Figure 10E:
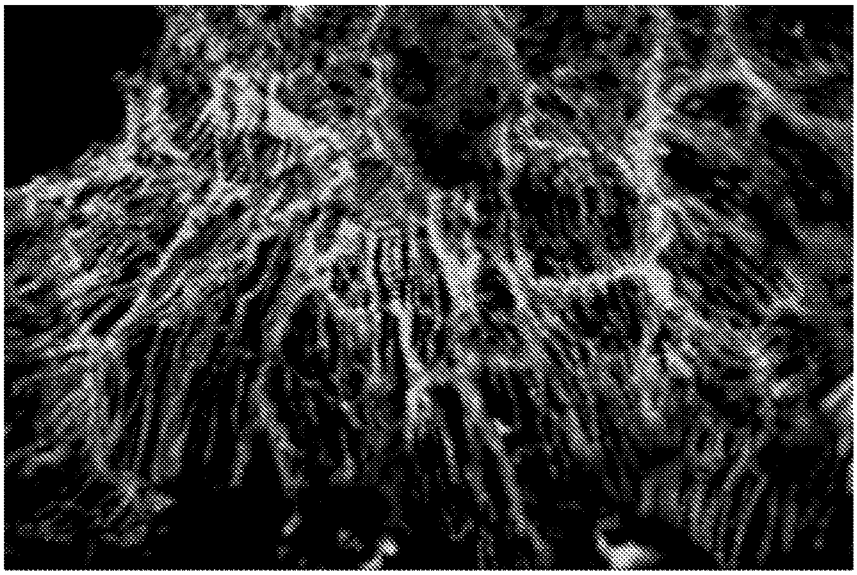
Figure 10D:
Figure 13A:
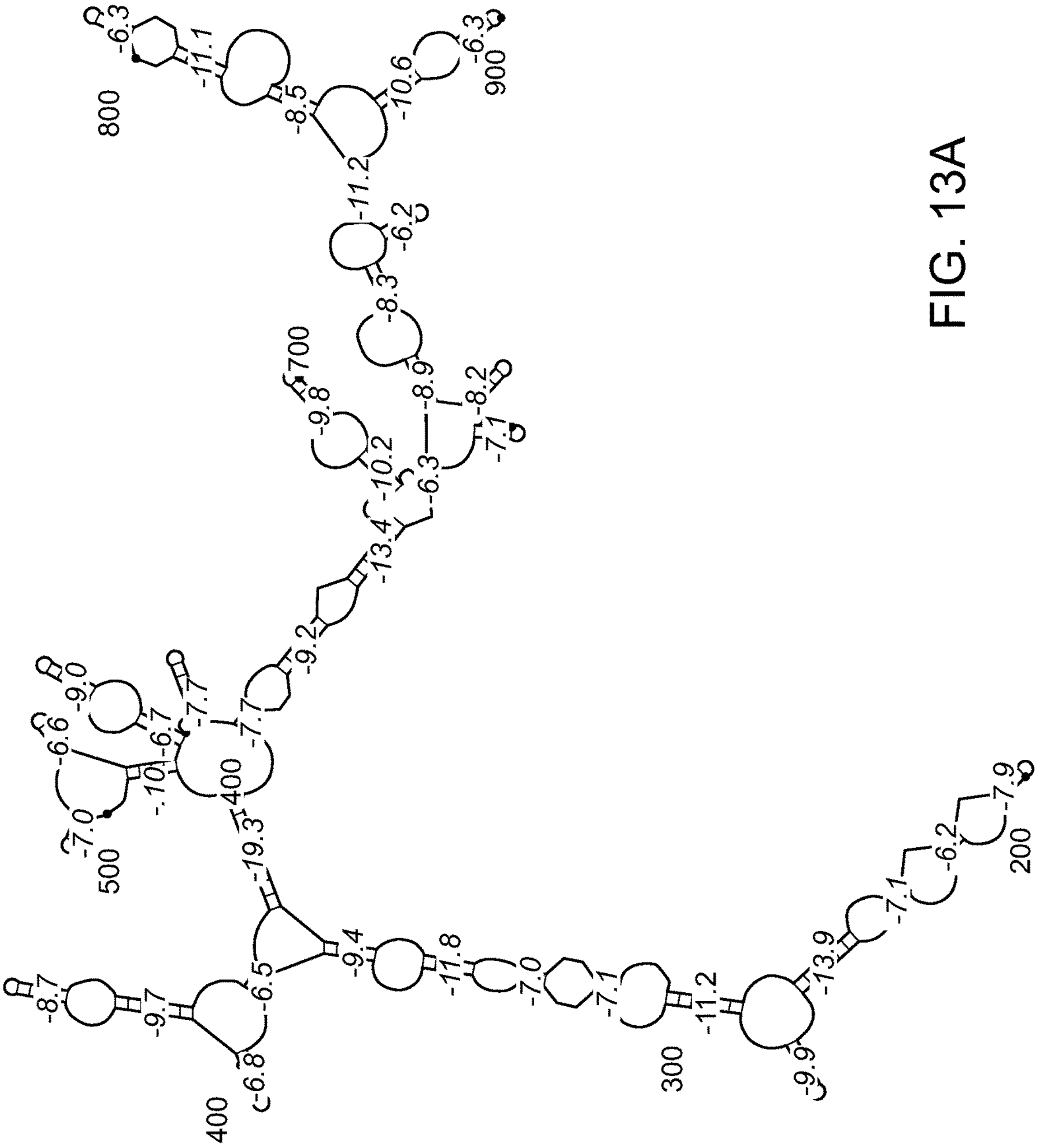
FIG. 13 includes the secondary structure prediction of the axolotl MIR and human RNA CIR 2 using Genebee RNA secondary structure prediction model. The Genebee program showed: 13A) the full length axolotl MIR, 13B) the full length mutant axolotl MIR, 13C) the active region (166 nucleotides) of the axolotl MIR, 13D) the active region (166 nucleotides) of the mutant axolotl MIR, 13E) the RNA sequence of CIR 2 with the poly U tail, and 13F) the RNA sequence of CIR 2 excluding the poly U tail. The black outlined regions are to highlight similarities seen between the upper right side regions of the predicted structures for the RNA sequence of CIR 2 (13E, 13F) in comparison to the right half of the active MIR structure (13C).
Figure 13B:
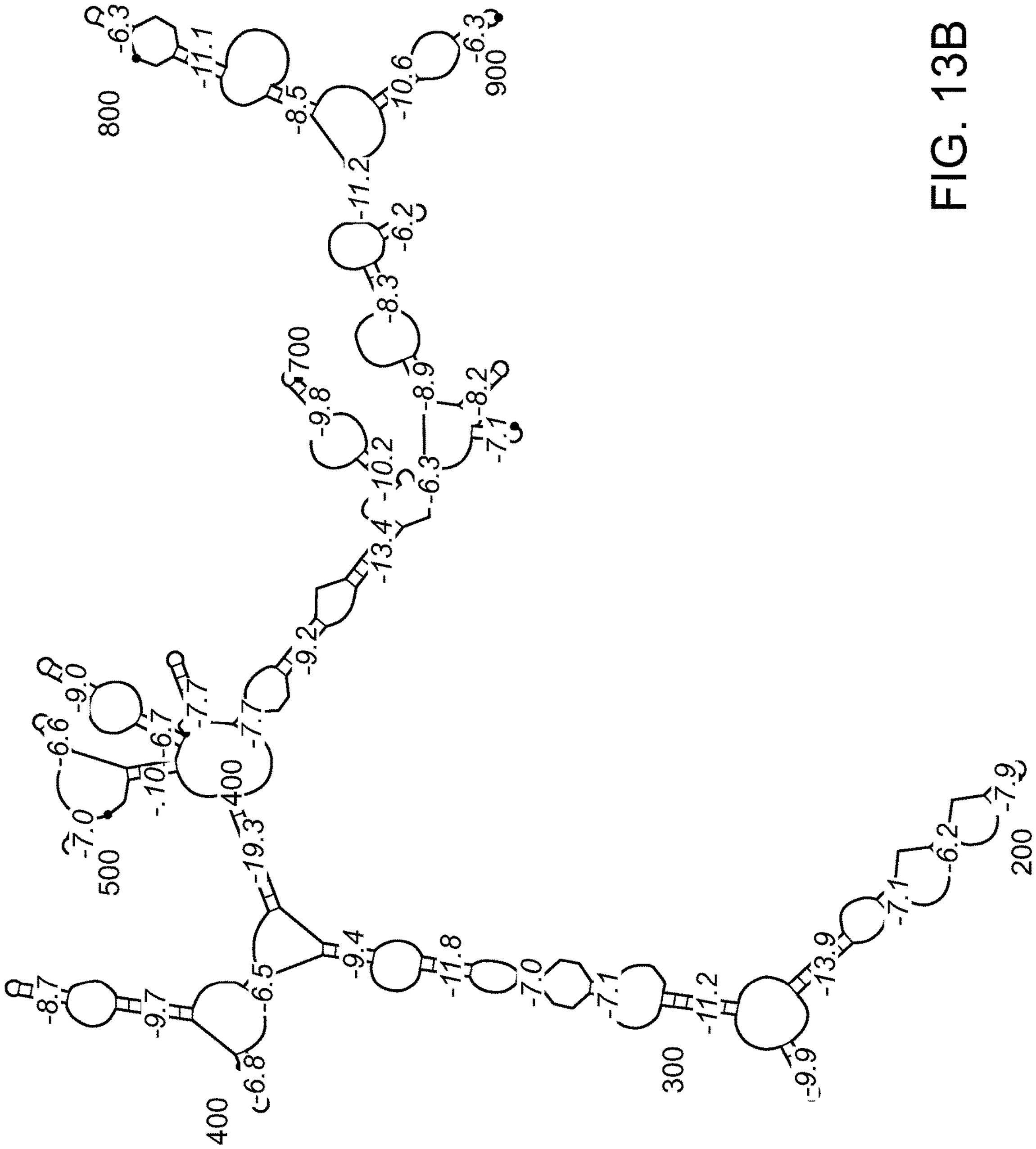
Figure 13C:
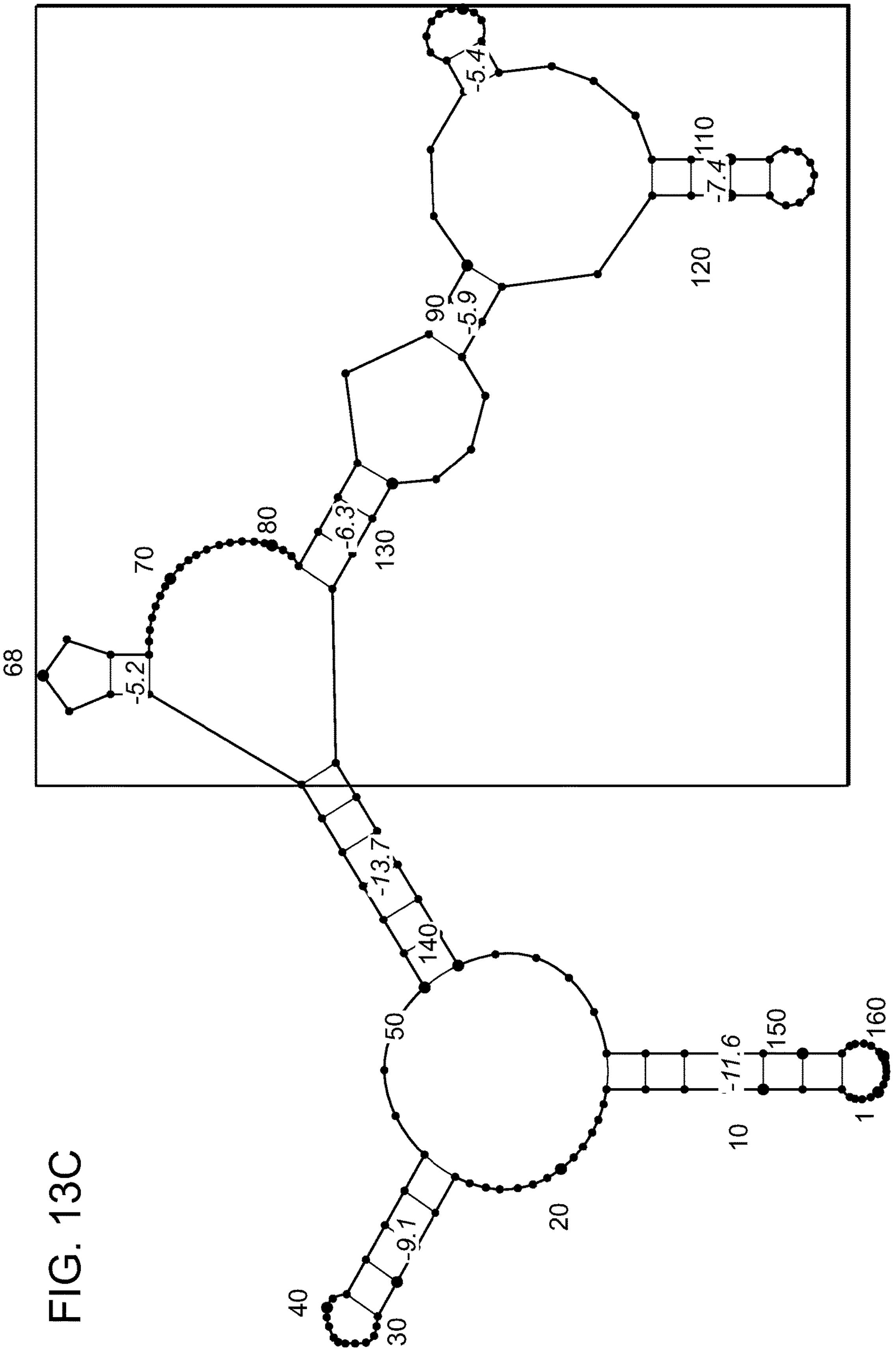
Figure 13D:
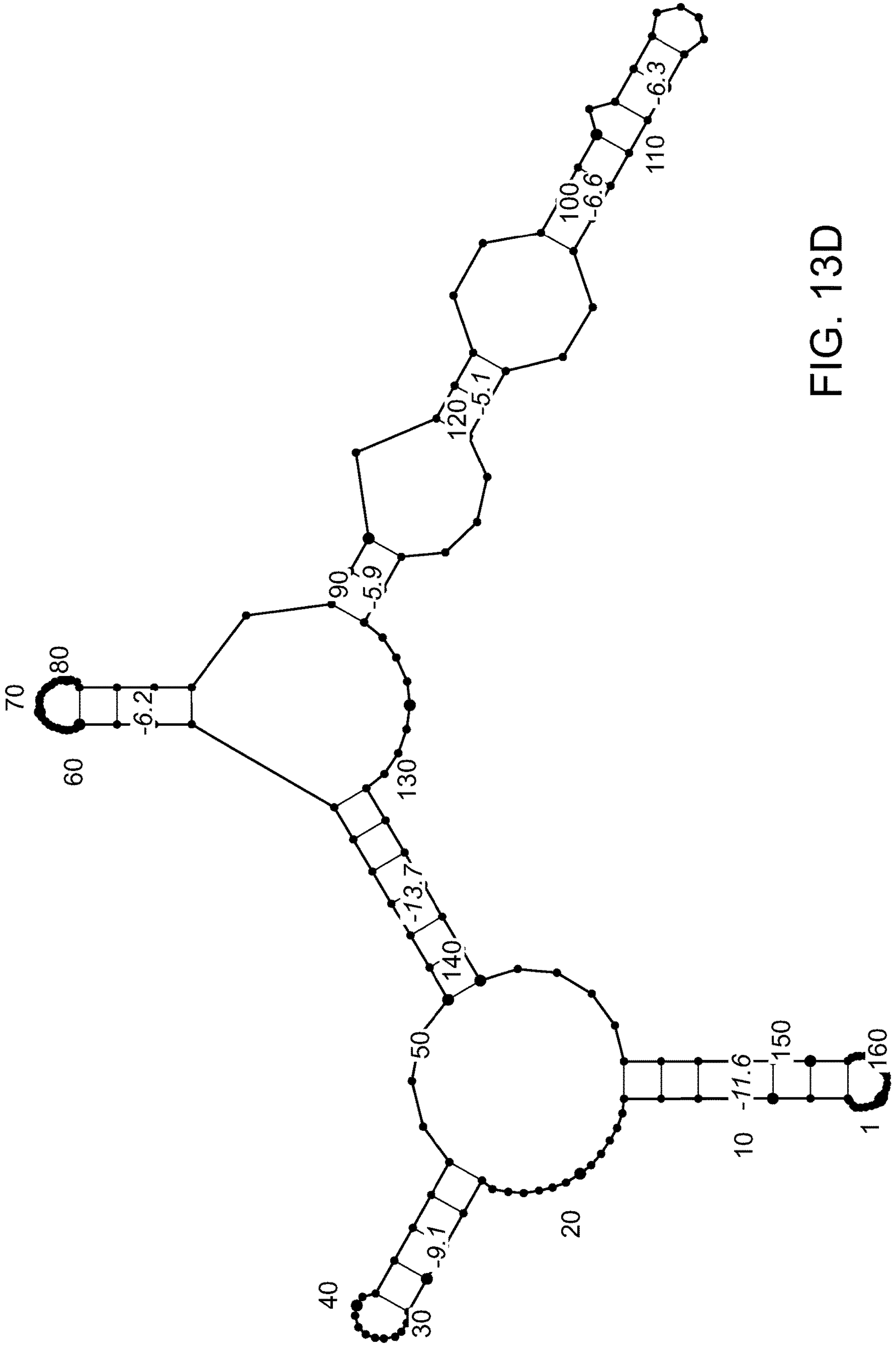
Figure 13E:
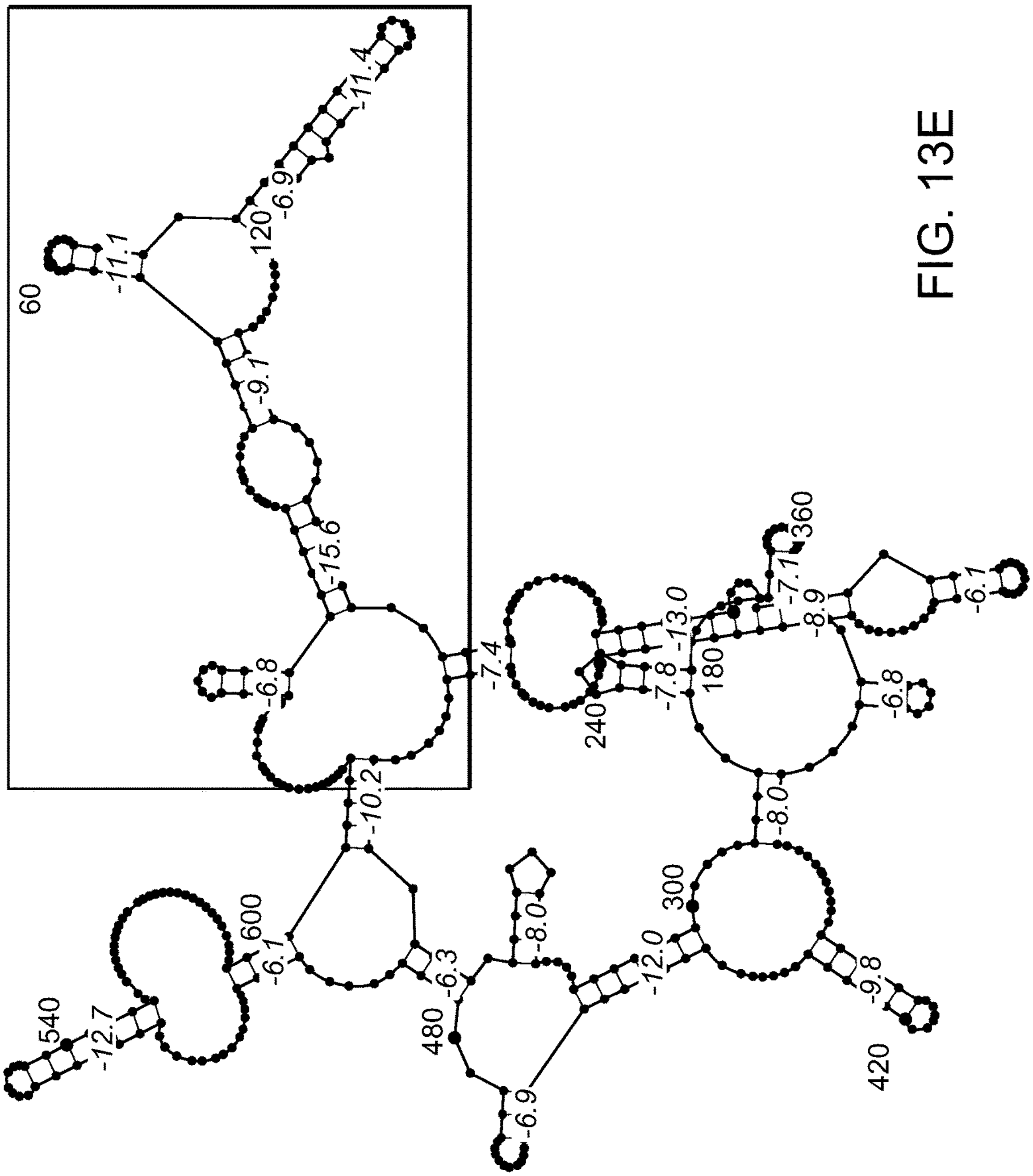
Figure 13F:
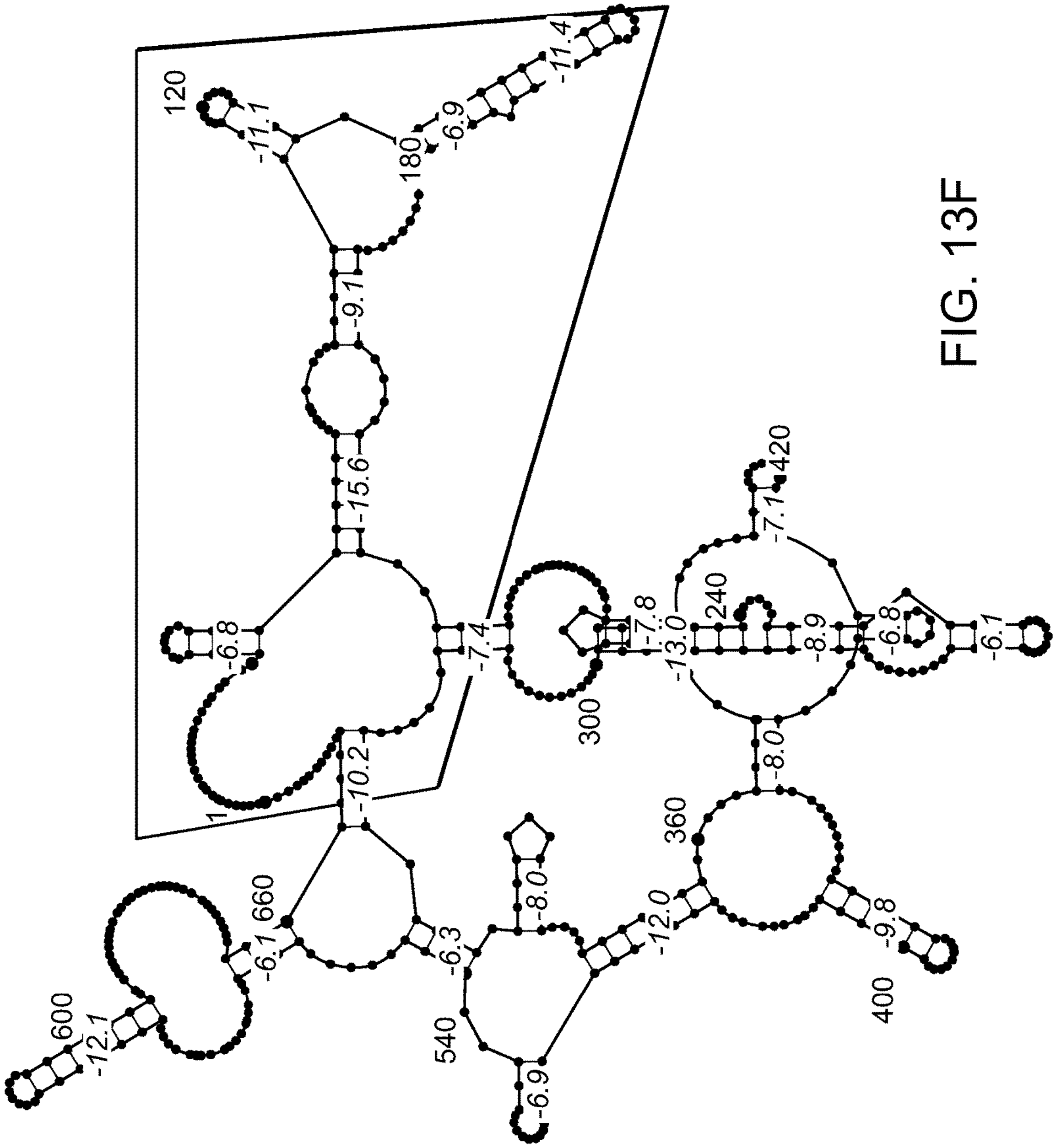
Figure 14A:
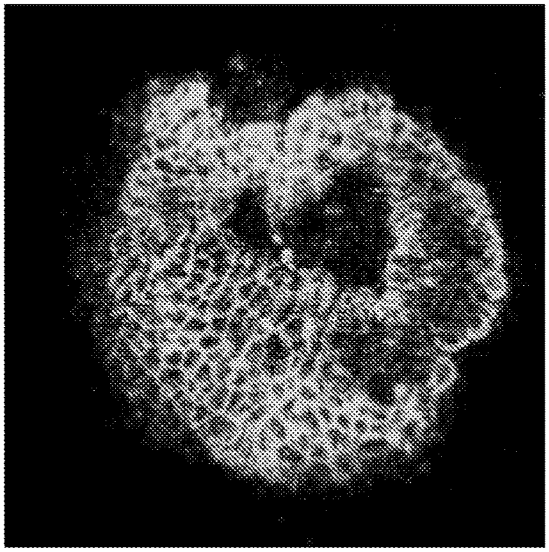
FIG. 14 shows normal axolotl hearts with complete staining. This type of control was conducted to illuminate what a full axolotl embryonic heart looks like when it has developed correctly and has undergone complete staining with the primary and secondary antibodies (14A and 14B). The darker stain serves as a marker for the myofibrillar protein, tropomyosin, which is almost completely absent in mutant hearts.
FIG. 14C reveals how tropomyosin rich and well-developed the normal axolotl embryonic heart is past stage 34, due to the large areas of fluorescent staining present on the tissue.
FIG. 14D illustrates the presence of individual myocardial cells and how the surfaces of these cells are covered with tropomyosin.
FIG. 14E shows how the cells and tropomyosin are oriented when the laser scans deeper into the tissue. The lines or bands located on the periphery of the cells represent myofibril sarcomeres containing tropomyosin.
FIG. 14F show muscle fibers of a normal heart with functioning myocardial cells. Striated structures surrounding the cells reveal the heart's ability to successfully contract due to the presence of myofibrils. When examining the normal heart tissue closer, FIG. 14G, it becomes apparent that bands of tropomyosin are present. These bands are best identified as chains of fluorescent dots (FIG. 14H).
Figure 14B:
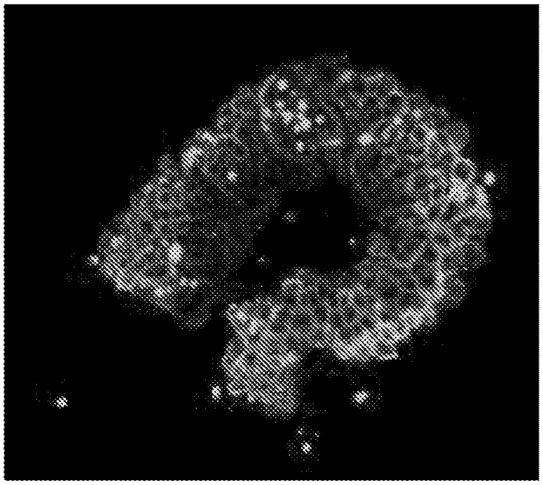
Figure 14C:
Figure 14D:
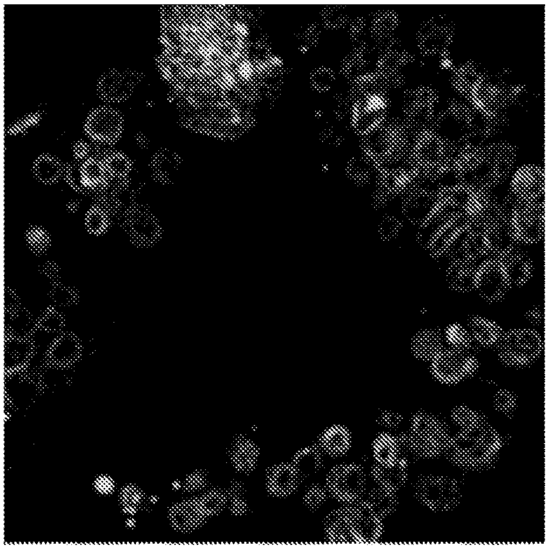
Figure 14E:
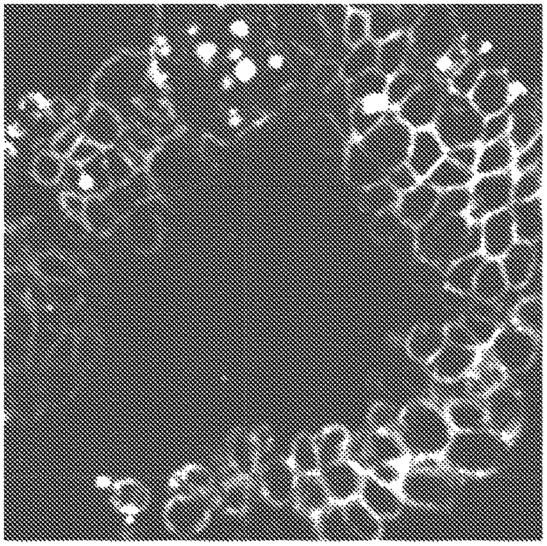
Figure 14F:
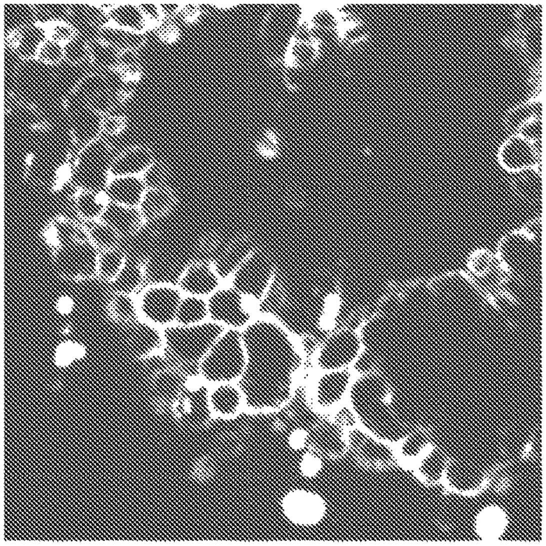
Figure 14G:
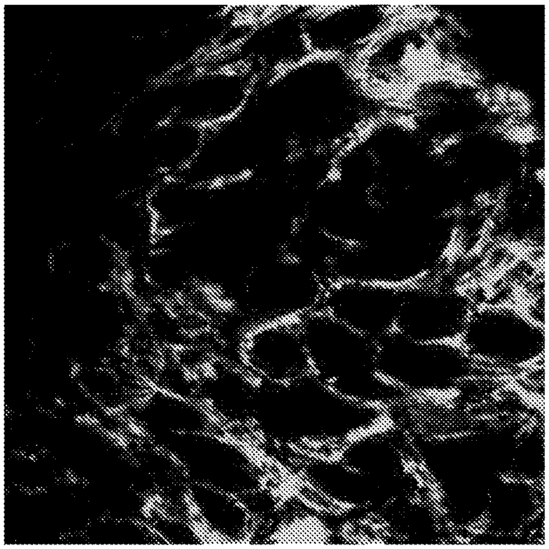
Figure 14H:
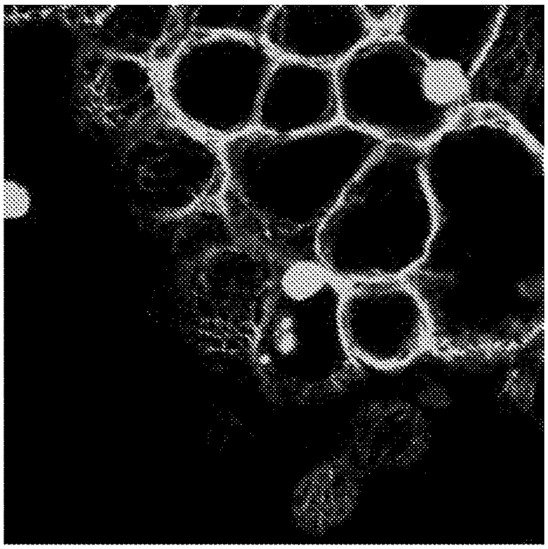
Figure 15A:
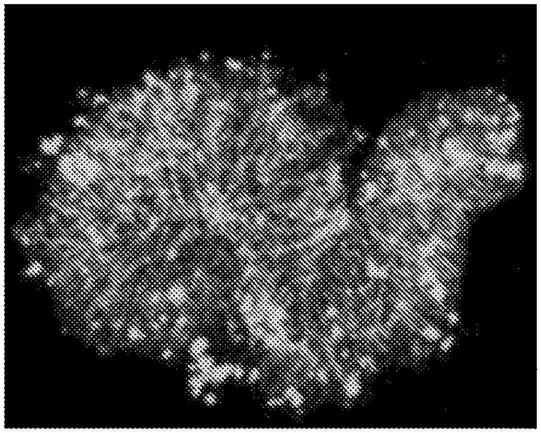
FIG. 15 shows mutant axolotl hearts with complete staining. Appearance of fluorescence in the mutant heart tissue reveals that tropomyosin is present. Because mutant hearts usually contain little to no tropomyosin, these images show that rescuing of mutant hearts has occurred due to their treatment with human RNA CIR 2 (15A and 15B).
FIG. 15C shows that the tropomyosin is now present, and that the tropomyosin is organized within myofibrils due to the clear outlining of the myocardial cells. Tropomyosin fluorescence shows clear staining of the heart's outline and myocardial units (15D and 15E). Detailed staining reveals that the rescued mutant heart is now functional (15F); The image shows that RNA CIR 2 caused the formation of tropomyosin isoforms, which were then used to generate complete myofibrils, leading to the formation of functional myocardial muscle cells. Part 15G focuses on the myofibrils present along the periphery of the individual cells while Part 15H reveals the presence of expansive myofibrils within the cells. Some striations can be seen.
Figure 15B:
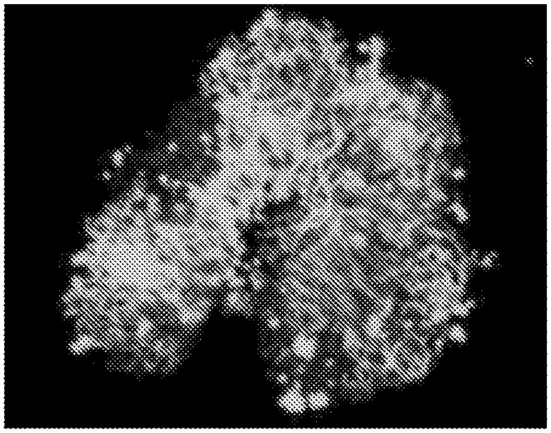
Figure 15C:
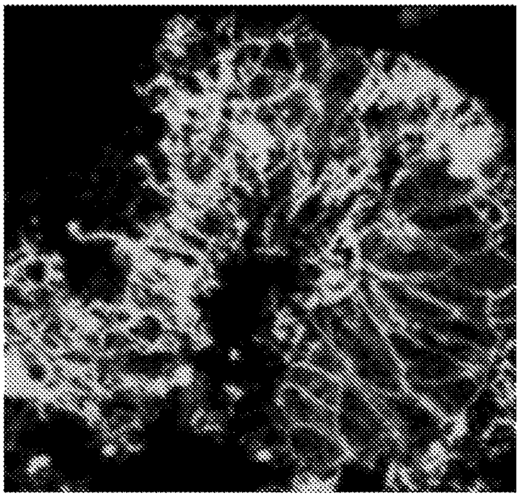
Figure 15D:
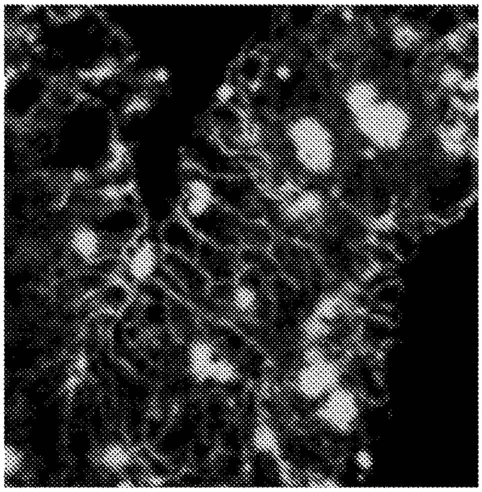
Figure 15E:
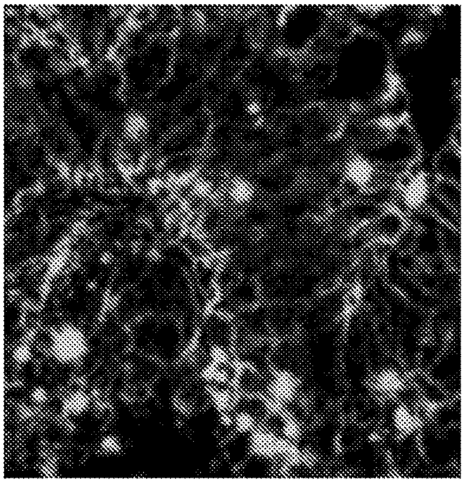
Figure 15F:
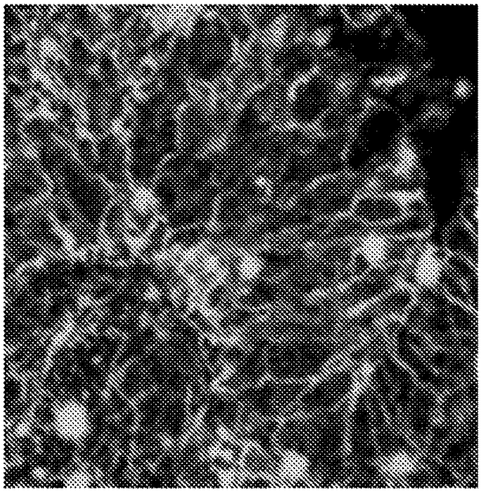
Figure 15G:
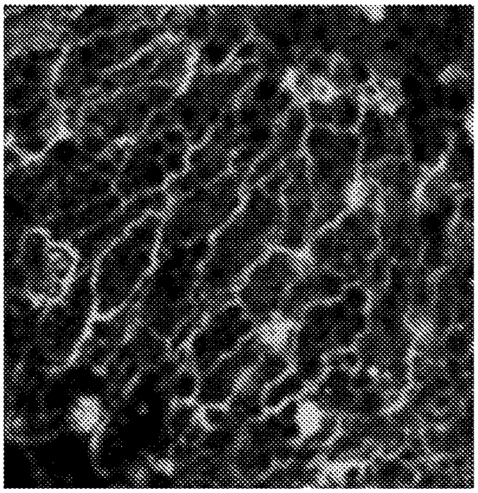
Figure 15H:
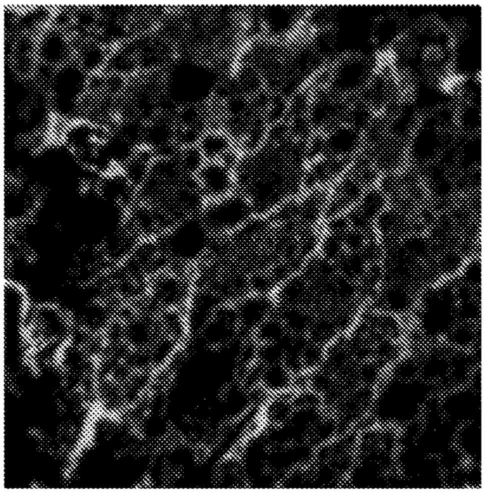
Figure 15I:
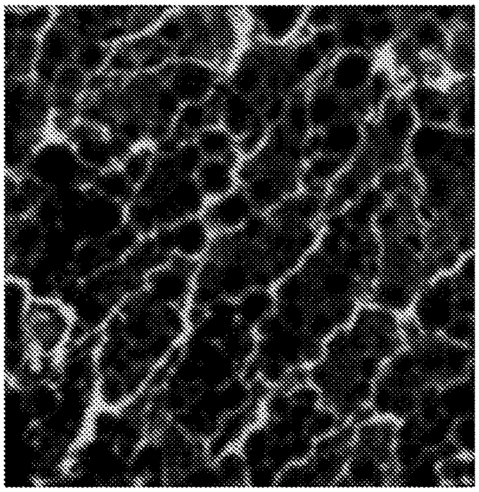
Figure 15J:
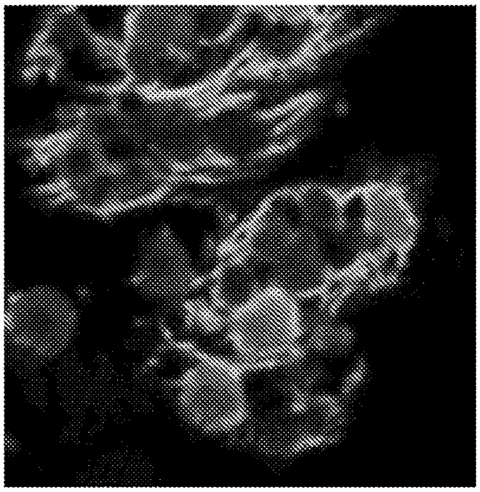

Sequences comparisons of axolotl and human CIR 1 were performed, and no sequence matches were identified. However, there were similarities in their secondary structures which were generated by using the online computational software GeneBee Program developed at the Belozersky Institute in Moscow, Russia (FIG. 9). FIG. 9 shows two branches of the human RNA from CIR 1 (FIG. 9A) are structurally very similar to the axolotl RNA (FIG. 9B).

Example 6: Bioassays with RNA Treatment (CIR 2)

Methods: Cloning, PCR, and RNA Synthesis:

Through the use of a Invitrogen Cloneminer II cDNA Library Construction Kit, a cDNA library consisting of 400 clones was constructed from human fetal total heart RNA. Once the cDNA clones were obtained, PCR was conducted to generate exponential amounts of the clones and then their corresponding RNA molecules were created using a New England Biolabs Inc. T7 High Yield RNA Synthesis Kit. The concentration of each clone was determined using Excel by comparing the absorbance values of RNA controls to the experimental absorbance values of the clones obtained with a plate reader.

Animal Husbandry and Bioassays:

These RNA molecules were tested on mutant axolotl hearts through the use of bioassays to determine if any had rescuing abilities. Mutant hearts were obtained for this procedure through identification of mutant axolotl embryos and the dissection of their hearts using microsurgical techniques. Every individual heart that was removed was placed in a drop of Holtfreter's solution on a parafilm-lined Petri dish. The RNA molecules from the 400 different clones were divided into groups of 12 and each group was tested using three hearts each. The hearts were treated with RNA groups by mixing the RNA molecules from the 12 clones in Holfreter's solution with an equal amount of 0.4 mg/ml lipofectin solution and then adding the combined RNA solution into the drop the heart was in.

Results:

The bioassays were conducted with groups made of 12 pooled RNAs in each and 3 mutant non-beating hearts per group. Alongside the multiple bioassay experiments, control experiments involving mutant hearts with no treatment and normal beating hearts were conducted. Groups that caused the treated mutant hearts to begin beating by around the 2nd-4th day of treatment were separated into smaller testing groups until each individual RNA had been checked for rescuing abilities. Of the 400 clones tested, so far only RNA CIR 2 and two others have shown rescuing abilities and caused non-beating mutant hearts to beat and are being reported separately.

Example 7: Confocal Microscopy of Normal and Mutant Axolotl Hearts

Methods: Fixation, Staining, and Confocal Microscopy:

When a treated mutant heart showed signs of being rescued through rhythmic contractions and beating, the heart was fixed using paraformaldehyde and immunofluorescently stained for tropomyosin. The primary antibody used was a monoclonal anti-tropomyosin CG3 antibody from Abcam and the secondary antibody was a Goat F(ab) anti-mouse polyclonal antibody with a Fluorescein isothiocyanate (FITC) tag that is excited at 490 nm. These hearts were then analyzed using a confocal microscope to identify and localize the presence of tropomyosin and organized sarcomeres. The RNA group that led to the rescue was further divided and tested in smaller groups until the sole RNA responsible for the rescuing was found.

Results:

The various bioassay controls and the experimental beating mutant hearts rescued by RNA CIR 2 were fixed, stained for tropomyosin, and analyzed using an Olympus BX62 scanning laser confocal microscope as shown in FIG. 10.

Example 8: Sequencing and Secondary Structure Prediction of CIR 2 and MIR

Methods: Sequencing and Secondary Structure Prediction:

When the confocal analyses demonstrated that a certain RNA had rescuing abilities, that RNA was sent to Functional Biosciences (Madison, Wis.) to determine its original DNA sequence.

The DNA sequence associated with the rescuing RNA was screened for vector contamination using www.ncbi.nlm.nih.gov and then trimmed to remove any contamination or poly A tails. The online NCBI BLAST program was utilized to determine what the exact sequence was within the human genome and the sequence editor database at www.fr33.net was used to convert the DNA sequence into the RNA sequence. The resulting RNA sequence was entered into an RNA secondary structure prediction site at ma.tbi.univie.ac.at, which produced possible secondary structures for the RNA. The RNA's secondary structure was then compared to the secondary structure of the axolotl MIR to see if any similarities exist.

Results:

PCR products and plasmid containing the DNA that corresponded to RNA CIR 2 were sent to Functional Biosciences (Madison, Wis.) for the determination of its DNA sequence (FIG. 11).

The trimmed DNA sequence was entered into the online NCBI BLAST program to determine what exactly the CIR 2 sequence coded for. Exclusion of the poly A tail resulted in several 100% human mitochondrial matches, such as a published entry titled *Homo sapiens* isolate B3 mitochondrion, complete genome. When analyzed further, it became apparent that the complete RNA CIR 2 from beginning to end (nucleotide 1-632) had homology with nucleotides 7671-8302 of the *Homo sapiens* isolate B3 mitochondrion complete genome, which codes the cytochrome c oxidase II subunit (COX2) gene (FIG. 12).

The DNA sequence was then converted into the following RNA sequence using a sequence converter with the poly U tail underlined (SEQ ID NO. 15):

UUUUUUUUUUUUUUUUUUUUUUUUUUUUUUUUUUUUUUUUUUUUUUUU

UUUUUNUUUGGCUCUAGAGGGGGUAGAGGGGGUGCUAUAGGGUAAAUA

CGGGCCCUAUUUCAAAGAUUUUUAGGGGAAUUAAUUCUAGGACGAUGGGC

AUGAAACUGUGGUUUGCUCCACAGAUUUCAGAGCAUUGACCGUAGUAUAC

CCCCGGUCGUGUAGCGGUGAAAGUGGUUUGGUUUAGACGUCCGGGAAUUG

CAUCUGUUUUUAAGCCUAAUGUGGGGACAGCUCAUGAGUGCAAGACGUCU

UGUGAUGUAAUUAUUAUACGAAUGGGGGCUUCAAUCGGGAGUACUACUCG

AUUGUCAACGUCAAGGAGUCGCAGGUCGCCUGGUUCUAGGAAUAAUGGGG

GAAGUAUGUAGGAGUUGAAGAUUAGUCCGCCGUAGUCGGUGUACUCGUAG

GUUCAGUACCAUUGGUGGCCAAUUGAUUUGAUGGUAAGGGAGGGAUCGUU

GACCUCGUCUGUUAUGUAAAGGAUGCGUAGGGAUGGGAGGGCGAUGAGGA

CUAGGAUGAUGGCGGGCAGGAUAGUUCAGACGGUUUCUAUUUCCUGAGCG

UCUGAGAUGUUAGUAUUAGUUAGUUUUGUUGUGAGUGUUAGGAAAAGGG

CAUACAGGACUAGGAAGCAGAUAAGGAAAAUGAUUAUGAGGGCG

The possible secondary structures of the full length axolotl MIR, full length mutant axolotl MIR, active region of the axolotl MIR, active region of the mutant axolotl MIR, the RNA sequence for CIR 2 with the poly U tail, and the RNA sequence for CIR 2 without the poly U tail were determined using the Genebee RNA secondary structure prediction model (FIG. 13).

Example 9: Reagent and RNA Preparation for Normal and Mutant Heart Testing

Methods:

Human total fetal heart RNA, from Agilent Technologies, Inc (California), was ordered. Using this RNA, cDNA construction and cloning procedures were employed. The purpose of the cloning procedure was to separate out and purify the individual messenger RNAs (mRNAs), generate cDNA and purify a large quantity of each for further experimentation. The cloning kit that was used is the Cloneminer II cDNA Library Construction Kit made by Invitrogen (cat. # A11180). 10 μl of starting mRNA was prepared. 1 μl of Biotin-attB2-Oligo(dT) Primer, which binds to the RNA poly A tail, was added to the RNA4 μl of 5× First Strand Buffer, 2 μl of 0.1 M Dithiothreitol (DTT), and 1 μl of 10 mM (each) Deoxynucleotide triphosphates (dNTPs) were mixed into a separate tube. Once the mixture from the priming reaction cooled to 45° C., it was added to the above mentioned tube. Then 2 μl of SuperScript III RT, a reverse transcriptase that can adhere to the Biotin-attB2-Oligo(dT) Primer and synthesize a single stranded cDNA from the RNA template, was added The tube was incubated in the thermocycler in increments of 45° C. for 20 minutes, then 50° C. for 20 minutes, and then 55° C. for 20 minutes. The tube was placed on ice the next day and then the following reagents were added: 91 μl of DEPC-treated water, 30 μl of 5× Second Strand Buffer, 3 μl of 10 mM (each) dNTPs, 1 μl of *E. coli* DNA ligase, 4 μl of *E. coli* DNA Polymerase I, and 1 μl of *E. coli* RNAse H.2 μl of T4 DNA Polymerase was added to create blunt-ended cDNA. Then 10 μl 0.5 M Ethylenediaminetetraacetic Acid (EDTA) with a pH of 8 was added to stop the T4 DNA Polymerase reaction. Phenol/Chloroform Extraction: 160 μl of phenol:chloroform:isoamyl (25:24:1) were added to the tube and mixed thoroughly by hand for 30 seconds. The tube was centrifuged for 5 minutes at 16,000× gravity (g) and the resulting aqueous phase was transferred to a new tube.

Ethanol Precipitation:

Reagents were added to the tube containing the aqueous phase from the previous step in the following order: 1 μl of glycogen, 80 μl of 7.5 M NH4OAc (ammonium acetate), and 600 μl of 100% ethanol. The tube was placed at −80° C. for 10 minutes and then centrifuged at 4° C. for 25 minutes at 14,000×g. The resulting supernatant was removed, 150 μl of 70% ethanol was added to the pellet, and the tube was centrifuged at 4° C. for 2 minutes at 14,000×g. The supernatant was removed and the 70% ethanol wash was repeated. The cDNA pellet was left to dry for 10 minutes and then was resuspended in 22 μl of DEPC-treated water.

Ligating the attB1 Adaptor:

The tube was kept on ice and the following reagents were added: 10 μl of 5× Adapter Buffer, 4 μl of attB 1 Adapter, 8 μl of 0.1 M DTT, and 6 μl of T4 DNA Ligase. The solution was mixed by pipetting and then incubated at 16° C. for 16-24 hours. The T4 DNA Ligase attaches the attB1 Adapter to the blunt-ended DNA. The cDNA was then fractioned and separated into three tubes by column chromatography using Sephacryl® S-500 hR resin. Then, an ethanol precipitation was performed. Performing the BP Recombination Reaction: The following reagents were mixed in a new tube: solution from previous step that contains cDNA, 2 μl of pDONRTM 222, and 2 μl of TE buffer. The BP Clonase TM II enzyme mix was retrieved from the freezer, thawed, and then vortexed twice briefly. 3 μl of the BP Clonase TM II enzyme mix were added to the tube of cDNA. The tube was mixed by pipetting, centrifuged for 2 seconds, and then incubated at 25° C. for 16-20 hours. This reaction allowed for the cDNA of interest to be inserted into the pDONRTM 222 plasmid through a BP reaction. 2 μl of Proteinase K were added to the mixture and incubated at 37° C. for 15 minutes and then 75° C. for 10 minutes to stop the BP recombination reaction through inactivation.

The cDNA containing plasmids were mixed into a solution containing ElectroMAX DH10B T1 phage resistant cells and then the mixture was electroporated using Electroporation Procedure for pUC 19 control into ElectroMAX DH10B competent cells. A plating assay was then performed and plasmid DNA isolation was conducted with colonies of interest.

BsrGI Digest:

The following items were added to a new centrifuge tube in the order listed: 0.5 μl of 10 mg/ml Bovine Serum Albumin (BSA), 0.5 μl of 10×NE buffer, 9 μl of OmniSolv water, 20 μl of the plasmid DNA from one clone of the previous procedure, and 0.4 μl of BsrGI Digest. Six other tubes were prepared using the same measurements, 5 tubes with other clones, and the last tube with non-recombinant plasmids. The tubes were incubated at 37° C. for 2 hours. After incubation, 9 μl of 6× DNA loading buffer were added to each tube and mixed. 20 μl of each sample were then loaded onto a 1% agarose gel and the gel was allowed to run for 1 hour. The bands on the gel were visualized under ultraviolet light.

To run this procedure, non-recombinant plasmids, along with recombinant plasmids, that potentially contain cDNAs, were digested with the BsrGI enzyme and then the resulting bands on the gel were compared to see if cDNAs were present.

PCR:

Polymerase Chain Reaction (PCR) was conducted with the plasmids to generate exponential amounts of the cDNAs. In order to do this, specific primers, both forward and reverse versions containing T7 promoter regions, were determined and ordered from Integrated DNA Technologies (San Diego, Calif.). The forward primer was M13 Forward (−20) (SEQ ID NO. 5): 5'-TAATACGACTCACTATAGGGGTAAAACGACG GCCAG-3' and came in 29.8 nM. The reverse primer was M13 Reverse (SEQ ID NO. 6): 5'TAATACGACTCACTATAGGGCAGGAAACAGCTA TGAC-3' and came in 26.4 nM. For the PCR reaction, the concentration needed of the primers was 20 μM each so 1.5 ml of water was added to the forward primer and 1.3 ml of water was added to the reverse primer. For each cDNA sample, a new PCR tube was filled in order with 25 μl of MyTaq Red Mix made by Bioline, 1 μl of each primer solution, 15 μl of double distilled water (dd H2O), and 8 μl of the sample. The tubes were placed in an Eppendorf Mastercycler Gradient machine and the cDNA was heated to 95° C. for 1 minute to cause the two strands to separate. The PCR machine then ran through a cycle of 95° C. for 15 seconds, 55° C. for 15 seconds, and 72° C. for 10 seconds for 30 cycles. During this cycle, the specific primers annealed to complimentary sections of the cDNA when the temperature dropped to 55° C. Once the primers were attached, the reaction was heated to 72° C. so that a taq polymerase could adhere to the cDNA and synthesize complimentary strands from free nucleotides present in the solution. Each time a new strand was generated it was used in the next step, which is the reason why exponential amounts of cDNA were achieved with PCR. Once PCR was completed, gels were run with 5 μl of the resulting cDNA and 1.5 μl of 6× DNA gel loading dye to check that the procedure worked successfully.

Standard RNA Synthesis:

cDNA from the previous step had to be converted into RNA through the use of a T7 High Yield RNA Synthesis Kit by New England Biolabs Inc (Ipswich, Mass.). In a new microcentrifuge tube the following components were added in order: 10 μl of ATP/GTP/UPT/CTP mix, the 8 μl of cDNA solution from the previous procedure, and 2 μl of T7 RNA Polymerase mix. The tubes were pulsed in the centrifuge and then incubated at 37° C. for two hours.

the absorbance value of each sample, after being diluted 1,000 times, was measured at 250 nm using a BIO-TEK Synergy HT plate reader. The concentration of RNA in each sample was then determined by comparing the experimental absorbance values with a figure generated from absorbance values of known RNA control concentrations. These values were taken for later use in determining RNA concentrations for bioassay treatments.

Results:

Several digests were conducted, run on gels, and analyzed using UV light. This revealed that the procedures for cloning and the insertion of cDNA into the pDONR222 vector were successful. The BsrGI enzyme cuts the plasmid in particular sites, so any non-recombinant plasmids will have the same size segments. Therefore, the success of the cloning and insertion was determined due to the presence of different length segments of DNA between the various clone-containing plasmids after digestion. Also, after PCR, gels were run to check for products and to double-check that the cDNAs obtained were variable in length (data not shown).

The concentrations of the RNA present in each tube, following the standard RNA synthesis procedure were calculated using RNA controls and a plate reader set to 250 nm. Once the absorbance values were obtained for the controls, a figure was generated with a line of best fit and the concentrations of the samples were plugged into the equation for the linear best fit line to determine their concentrations. With a RNA control mix supplied by Ambion, dilutions of 0 ng/μL, 1 ng/μL, 3 ng/μL, 10 ng/μL, and 30 ng/μL were made and analyzed at 250 nm in a BIO-TEK Synergy HT plate reader. The absorbance values obtained for each were plotted to determine the equation for the linear line of best fit: $y=155.38x-10.249$. Results are found below in Table 2. The first column denotes the sample number/clone number, the second column contains the corresponding absorbance values, obtained from the plate reader, once the absorbance value of water has been subtracted, and the third column consists of the concentration determined by placing the absorbance value into the linear best fit model. Concentrations were calculated for all 400 samples, but were not all included here.

TABLE 2

RNA concentrations

| Sample # | Absorbance value (accounting for water abs) | Concentration (ng/μL) |
|---|---|---|
| 25 | 0.268 | 31.39284 |
| 26 | 0.214 | 23.00232 |
| 27 | 0.245 | 27.8191 |
| 28 | 0.208 | 22.07004 |
| 29 | 0.217 | 23.46846 |
| 30 | 0.207 | 21.91466 |
| 34 | 0.161 | 14.76718 |
| 35 | 0.237 | 26.57606 |
| 36 | 0.223 | 24.40074 |
| 37 | 0.228 | 25.17764 |
| 38 | 0.221 | 24.08998 |
| 39 | 0.19 | 19.2732 |
| 40 | 0.302 | 36.67576 |
| 41 | 0.242 | 27.35296 |
| 42 | 0.282 | 33.56816 |
| 44 | 0.421 | 55.16598 |
| 45 | 0.317 | 39.00646 |
| 46 | 0.214 | 23.00232 |
| 47 | 0.243 | 27.50834 |
| 48 | 0.249 | 28.44062 |
| 49 | 0.284 | 33.87892 |
| 50 | 0.149 | 12.90262 |

TABLE 2-continued

RNA concentrations

| Sample # | Absorbance value (accounting for water abs) | Concentration (ng/μL) |
|---|---|---|
| 51 | 0.236 | 26.42068 |
| 52 | 0.243 | 27.50834 |

Example 10: Bioassays with RNA Treatment of Clones

Methods: Mutant Hearts Obtained Through Animal Husbandry:

several matings of heterozygous adults (+/c×+/c) were conducted and documented. if a successful mating occurred, up to 600 eggs would be present. The eggs were removed from the tanks and observed to determine stages of development using the Bordzilovskaya et al. staging system for *Ambystoma mexicanum* (Bordzilovskaya el al. 1999).

Bioassays with RNA Treatment:

At around stage 36, the mutant embryos were separated from the others, placed in Holtfreter's solution that had been treated with a single drop of antibiotic/antimicotic, and were released from their jelly coats with dissection forceps. The embryos were then anesthetized with Finquel (tricaine methanesulfonate), immersed in Holtfreter's solution without antibiotic/antimycotic in grooves made into a clay dish, and held in place with sterilized staples. the heart of the embryo was removed through microsurgery. The hearts were then placed in droplets of Holtfreter's or Steinberg's saline solution that were placed on Parafilm within plates. Groups of 25 RNAs, each derived from pooling the RNAs obtained from the various clones were placed in solution with 2 hearts to see if they caused the hearts to beat. This was done by first diluting the 25 RNAs to 28 ng/μl with Holtfreter's solution based on the concentrations found with the plate reader to a total volume of 50 μl. Once that was finished, 50 μl of 0.4 mg/ml lipofectin from Invitrogen (Carlsbad, Calif.) were added to the RNA solution and left at room temperature for 15 minutes. Then 100 μl of Holtfreter's solution was added for a total volume of 200 μl. Each heart had 100 μl of a certain group added to it and was then kept at room temperature in a container with moist paper towels so that the solutions would not evaporate.

Results:

Axolotl embryonic hearts that were obtained from axolotl spawnings around stages 34-37 and had all symptoms of a mutant were microsurgically removed to be treated with different groups of the experimental RNA. The bioassays were conducted with groups made of 12 pooled RNAs in each and 3 mutant non-beating hearts per group. Alongside the multiple bioassay experiments, control experiments involving mutant hearts with no treatment and normal beating hearts were conducted. Groups that caused the treated mutant hearts to begin beating by around the 2nd-4th day of treatment were separated into smaller testing groups until each individual RNA had been checked for rescuing abilities. Of the 400 clones tested, so far only RNA CIR 2 and two others have shown rescuing abilities and caused non-beating mutant hearts to beat.

Example 11: Bioassays with RNA Treatment

Methods: Confocal Microscopy:

To further evaluate whether the RNA caused the axolotl heart to form myofibrils, the heart was fixed and stained with primary and secondary antibodies that specifically identified cardiac muscle myofibrils. The primary antibody used was a monoclonal anti-tropomyosin CG3 antibody ordered from Abcam and the secondary antibody was a Goat F(ab) anti-mouse polyclonal antibody with a Fluorescein isothiocyanate (FITC) tag that is excited at 490 nm. The procedure involved first fixing the heart in 2% paraformaldehyde for 30 minutes and then transferring the heart into 1 mM 3,3-Dithiodipropionic acid di(N-hydroxysuccinimide ester) Powder (DTSP) in (phosphate buffered saline) PBS for 15 minutes. The heart was rinsed for 3 minutes in PBS, transferred into 0.5% Nonidet P-40 in PBS for 15 minutes, and washed twice with 0.1 M glycine for 10 minutes. The heart was then placed in 0.05% Tween-20 and 3% bovine serum albumin (BSA) in PBS for 1 hour before being incubated overnight with the primary antibody diluted to 1:75. The heart was washed twice with 3% BSA in PBS for 3 minutes before and after incubation in the second antibody overnight. The heart was then transferred into 2% paraformaldehyde for 30 minutes, transferred into 0.1 M glycine in PBS, and mounted on a slide with 50-70 µl of SlowFade® Gold antifade reagent made by Invitrogen. A cover slip was gently placed over the heart and sealed with clear fingernail polish to prevent it from crushing the heart.

These antibody-stained hearts were analyzed and photographed using an Olympus BX62 scanning laser confocal microscope.

Results:

Various bioassay controls were conducted with mutant and normal hearts to establish standards. Then the controls were stained and analyzed using confocal microscopy methods. Numerous normal (data not shown) and mutant heart controls (FIG. 14) were performed to ensure accurate confocal microscopy images and ensure that resulting images were not due to tissue auto-fluorescence or any other factor other than the experimental. Beating hearts rescued by RNA CIR 2 were also analyzed after being stained to further confirm the findings (FIG. 15).

Example 12: Sequencing and Secondary Structure of CIR 2

Methods: Sequencing and Secondary Structure:

When both the bioassays and the confocal images indicated that a certain RNA had rescuing abilities, the RNA was sent to a company which has the capabilities to determine its original DNA sequence.

This DNA sequence was checked for vector contamination using www.ncbi.nlm.nih.gov and then trimmed to remove any contamination or poly tails. Once the sequence was complete, searches were conducted using the online NCBI BLAST program to determine what exactly the sequence was within the human genome. The DNA sequence was then entered into a sequence editor database at www.fr33.net, where it was converted into the RNA sequence. Then the RNA sequence was entered into an RNA secondary structure prediction site at ma.tbi.univie.ac.at, which produced possible secondary structures for the RNA. The RNA's secondary structure was then compared to the secondary structure of the axolotl MIR to see if any similarities were present.

Results:

The first PCR product containing DNA associated with RNA CIR 2 was sent to a sequencing company, the sequencing procedure failed. To ensure that the PCR product sent was not a contaminated sample, new PCR product was generated, using plasmids containing RNA CIR 2 that were obtained by growing more bacteria from a previously saved sample, and then compared to the older sent sample through gel electrophoresis. To ensure the sequencing procedure was not a failure due to the absence of cDNA in the sample CIR 2, another gel was run with uncut plasmid containing CIR 2, cut plasmid containing CIR 2 using the BSRGI digest, and PCR product generated from plasmid containing CIR 2.

New PCR products and plasmid containing the DNA that corresponded to RNA CIR 2 were sent to Functional Biosciences (FIG. 11).

Figure 16:
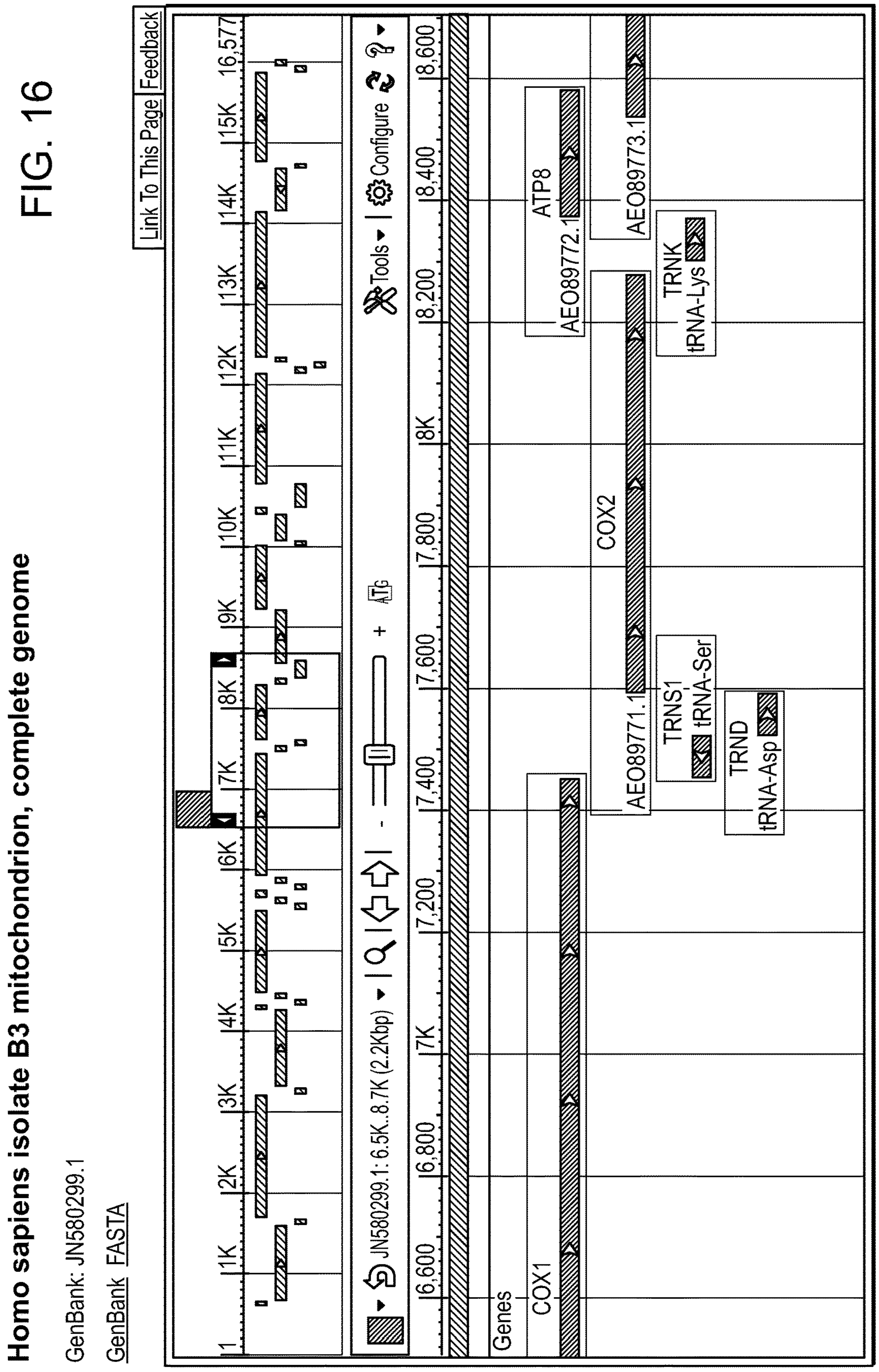
FIG. 16 shows a graphical analysis of the homology sequence CIR 2 has with *Homo sapiens* isolate B3 mitochondrion, complete genome. Since the nucleotides that CIR 2 has in common with *Homo sapiens* B3 mitochondrion run from nucleotide 7671-8302 in the mitochondrial sequence, it is likely that the DNA sequence of CIR 2 is associated with the cytochrome c oxidase subunit II (COX2) gene.

The trimmed DNA sequence was entered two different ways into the online NCBI BLAST program to determine what exactly the CIR 2 sequence coded for. The first way it was entered was without the poly A tail and resulted in several human mitochondrial matches 100%, such as a published entry titled *Homo sapiens* isolate B3 mitochondrion, complete genome (FIG. 16). Since the nucleotides that CIR 2 has in common with *Homo sapiens* B3 mitochondrion run from nucleotide 7671-8302 in the mitochondrial sequence, it is likely that the DNA sequence of CIR 2 is associated with the cytochrome c oxidase subunit II (COX2) gene.

Nucleotides 7594-8302 (709 characters) of the *Homo sapiens* B3 mitochondrion, complete genome with the underlined section representing the gene for cytochrome c oxidase subunit II and the yellow highlighted region representing the DNA sequence of CIR 2 (FIG. 12).

The second way the DNA sequence of CIR 2 was entered into the BLAST program was with the poly A tail included and led to a more specific match of *Homo sapiens*, Similar to cytochrome c oxidase II, clone IMAGE: 3681696, mRNA (FIG. 17). The alignment shows that the DNA sequence of CIR 2 matches completely to the cytochrome c oxidase II mRNA gene from the beginning to the poly A tail.

Figure 18:
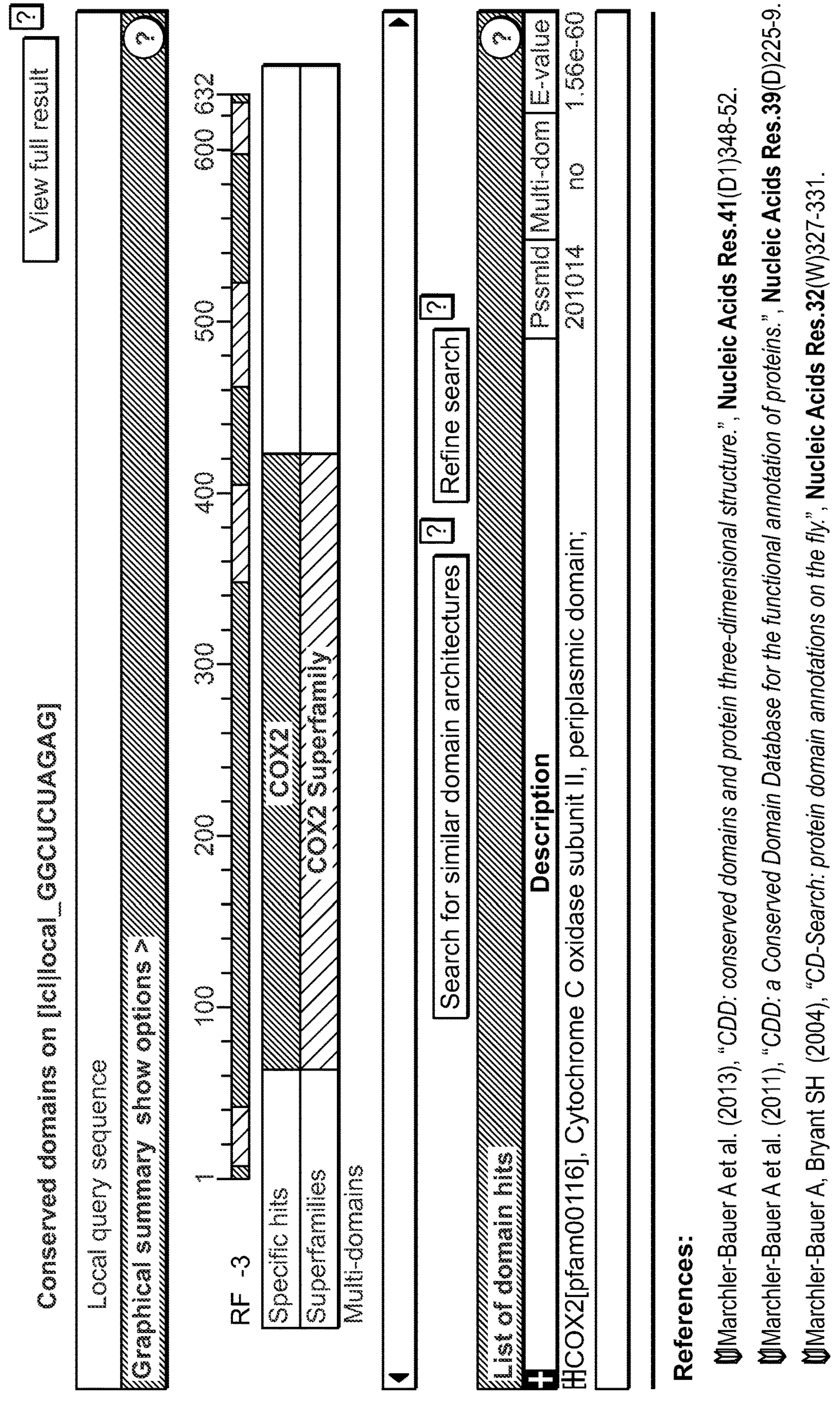
FIG. 18 shows a conserved domain. A "Conserved Domains" (SEQ ID NO. 19) search reveals that CIR 2 is associated with the COX2 superfamily.
Figure 19A:
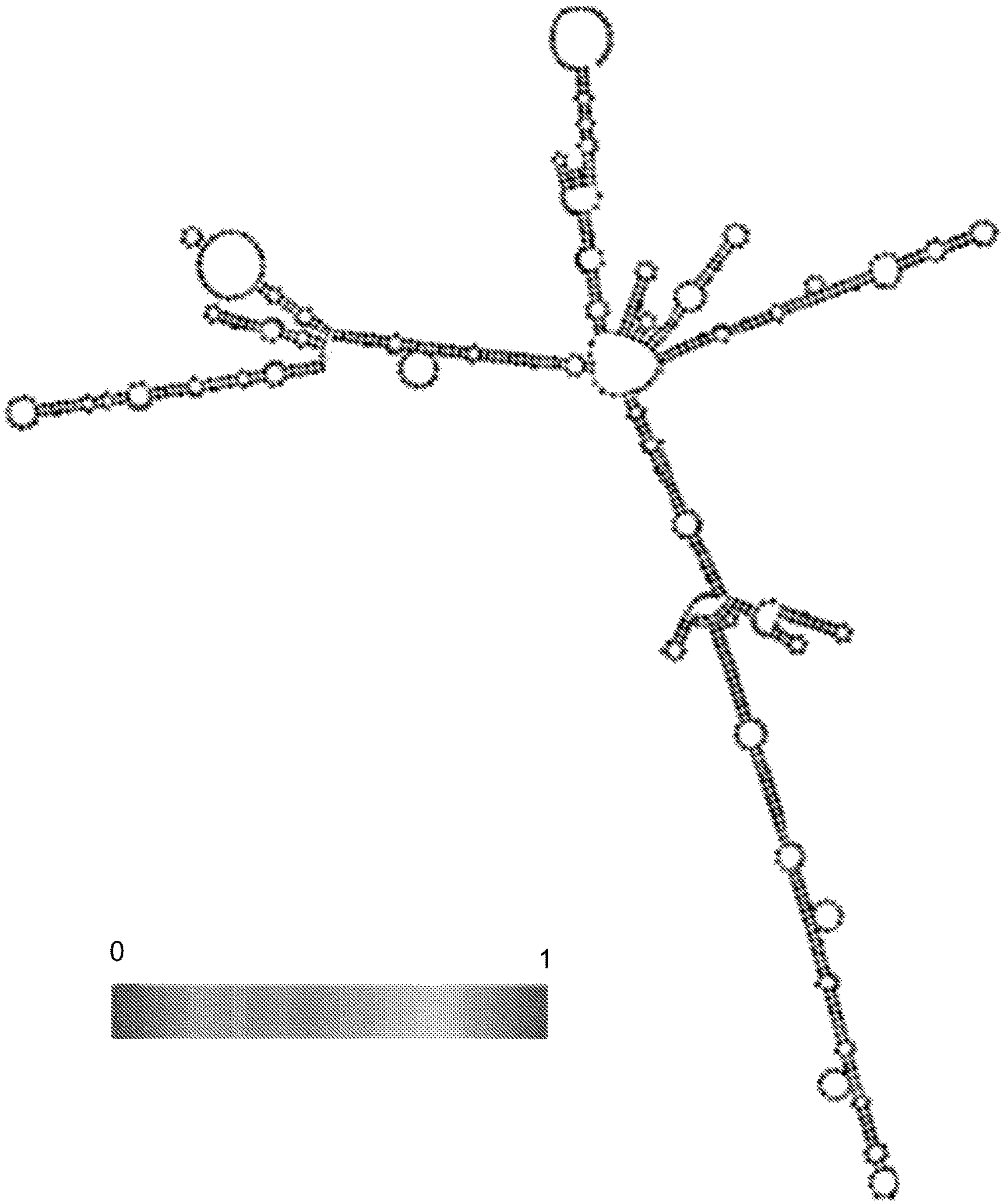
FIG. 19 shows axolotl MIR secondary structure predictions using RNAfold. Secondary structure prediction using the RNAfold program resulted in: 19A the minimum free energy (MFE) structure for the full length axolotl MIR, 19B the centroid RNA structure for the full length axolotl MIR, 19C the minimum free energy (MFE) structure for the full length mutant axolotl MIR, and 19D the centroid structure for the full length mutant axolotl MIR. The shade bar is for base-pairing probabilities; areas in dark gray are least likely while areas of light gray are most likely.
Figure 19B:
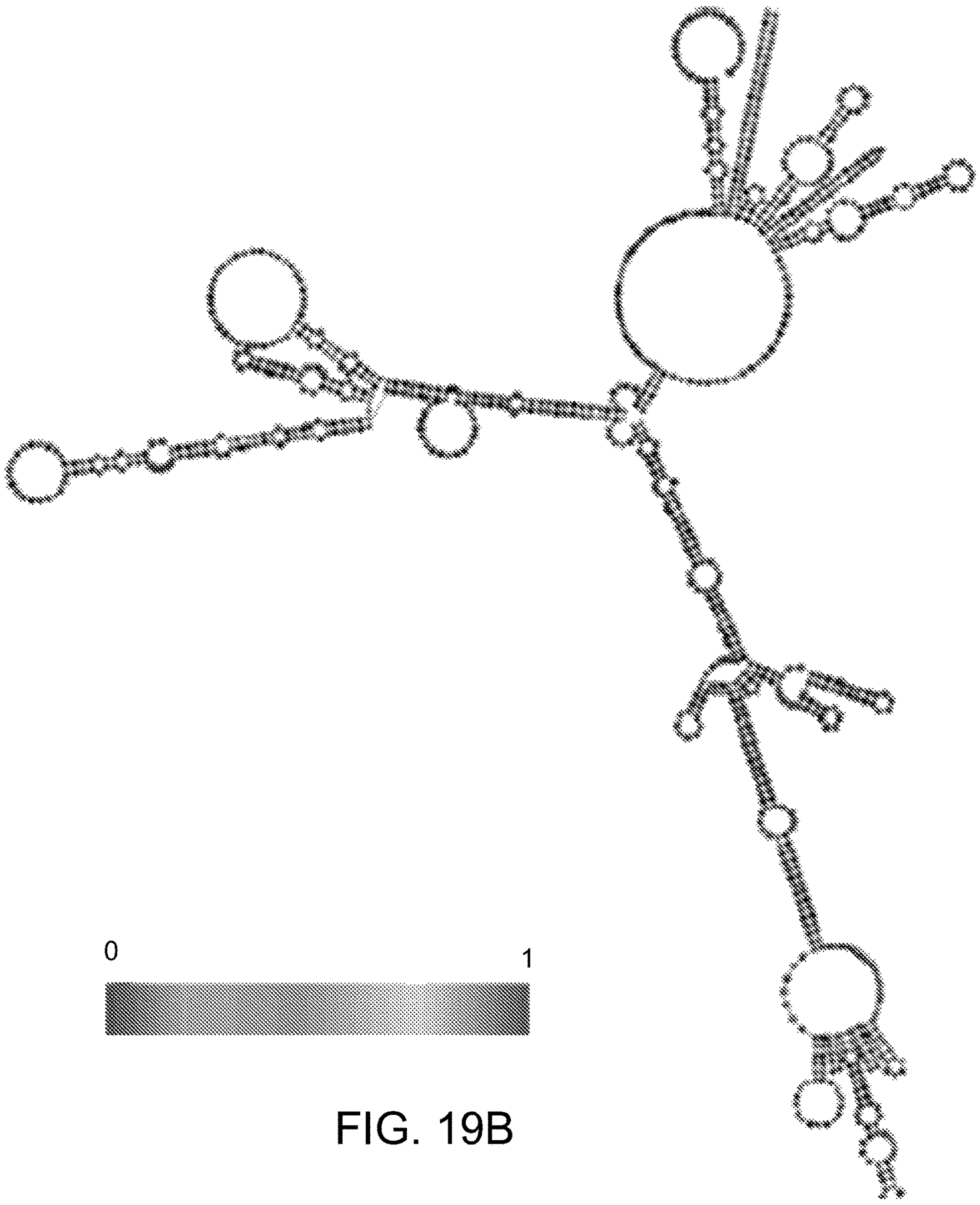
Figure 19C:
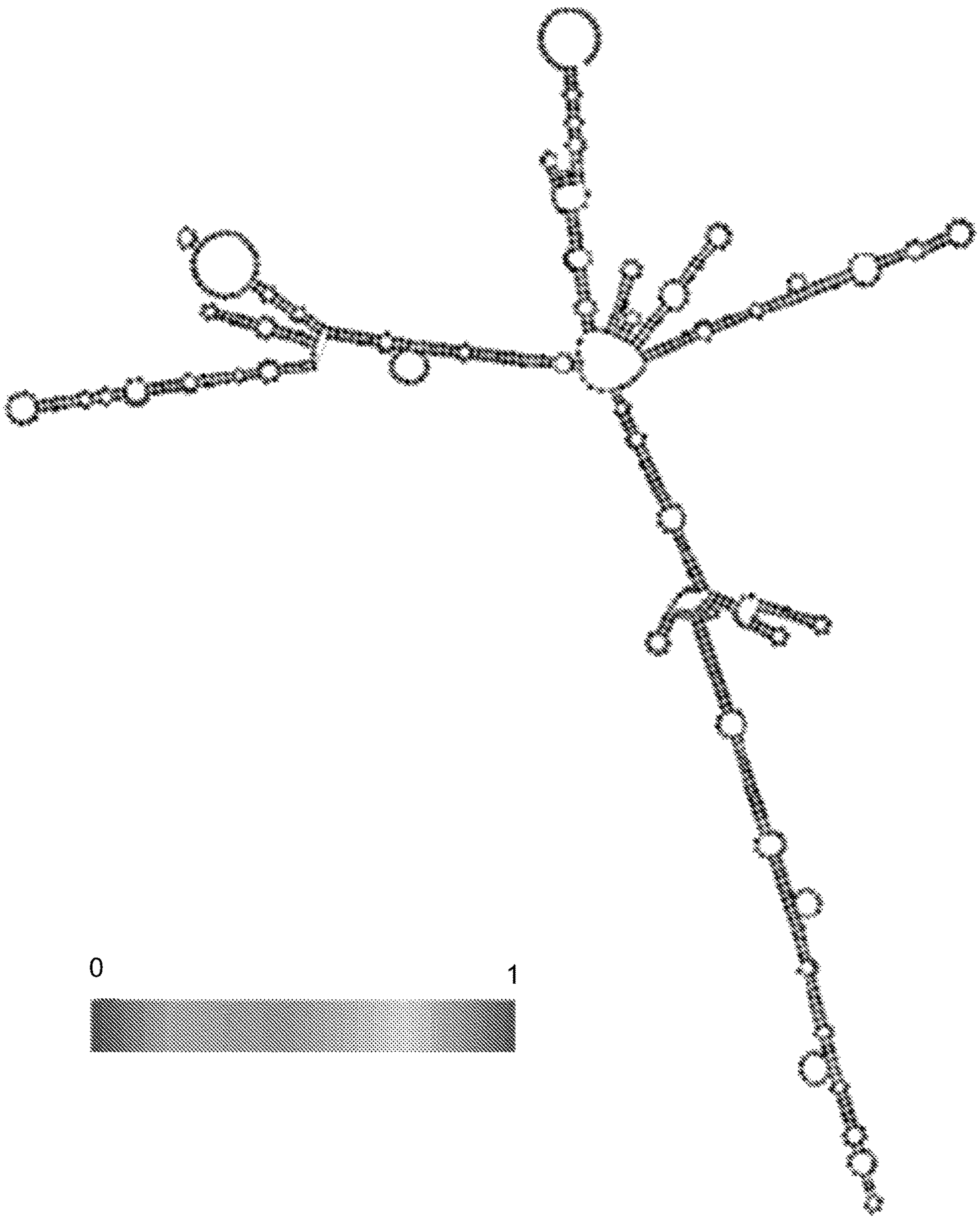
Figure 19D:
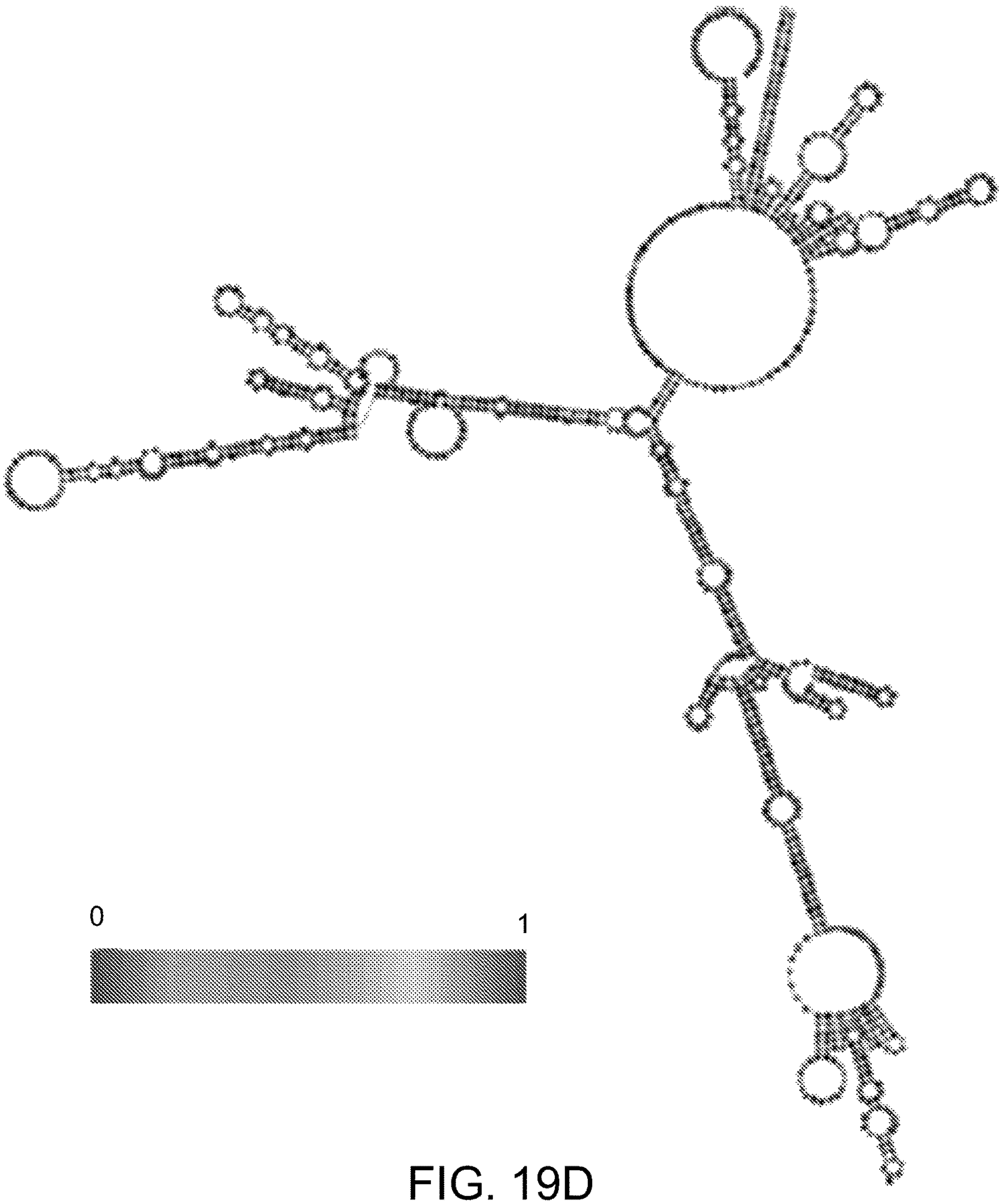
Figure 20A:
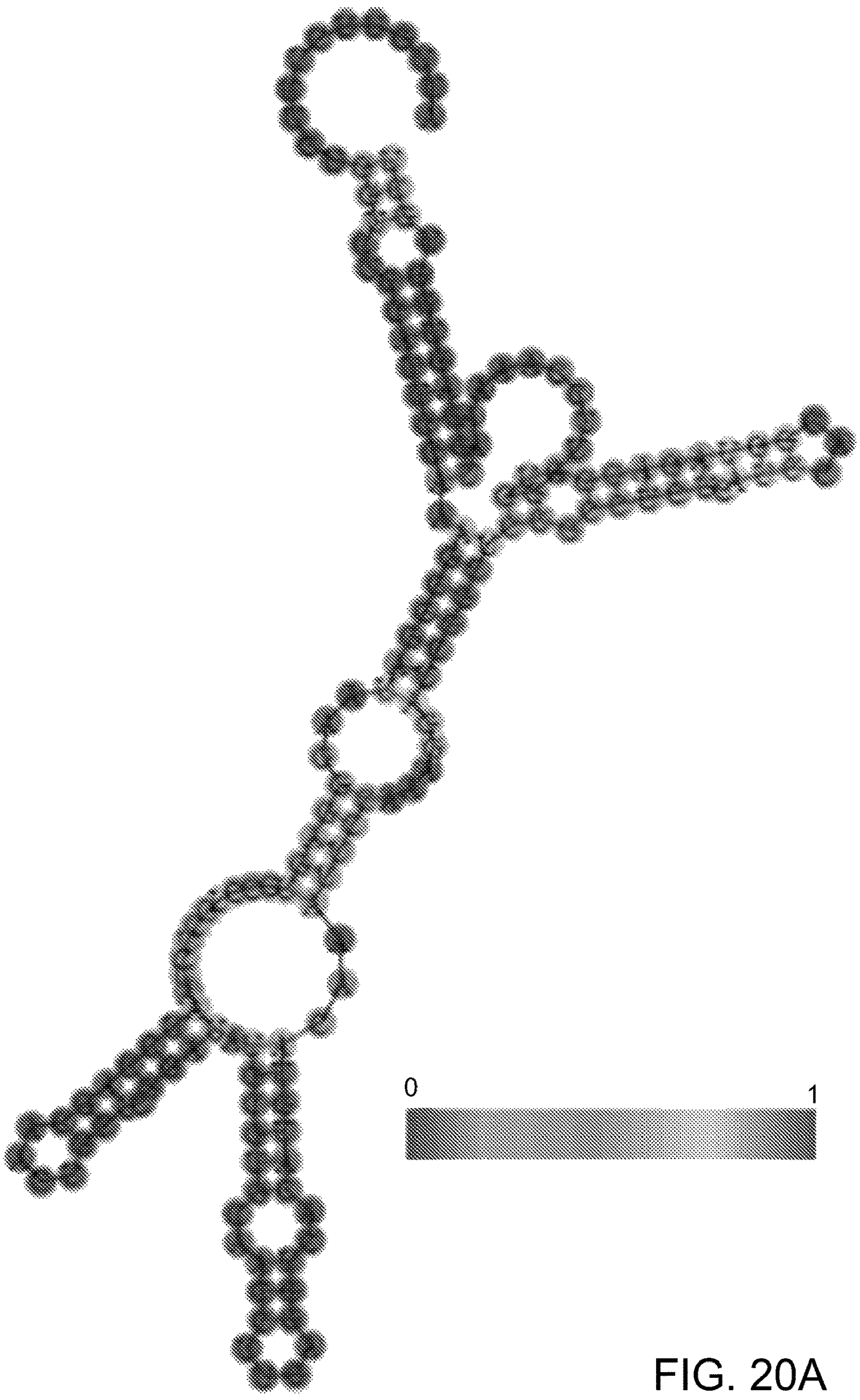
FIG. 20 shows the active sequence of the axolotl MIR secondary structure predictions using RNAfold. Secondary structure prediction for the active region (166 nucleotides) of the axolotl MIR using the RNAfold program resulted in 20A) the minimum free energy (MFE) structure for the axolotl MIR, 20B) the centroid RNA structure for the axolotl MIR, 20C) the minimum free energy (MFE) structure for the mutant axolotl MIR, and 20D) the centroid structure for the mutant axolotl MIR. The only difference between the normal and mutant MIR sequences is a single substitution, but it leads to dissimilar secondary structures The shade bar is for base-pairing probabilities; areas in dark gray are least likely while areas of light gray are most likely.
Figure 20B:
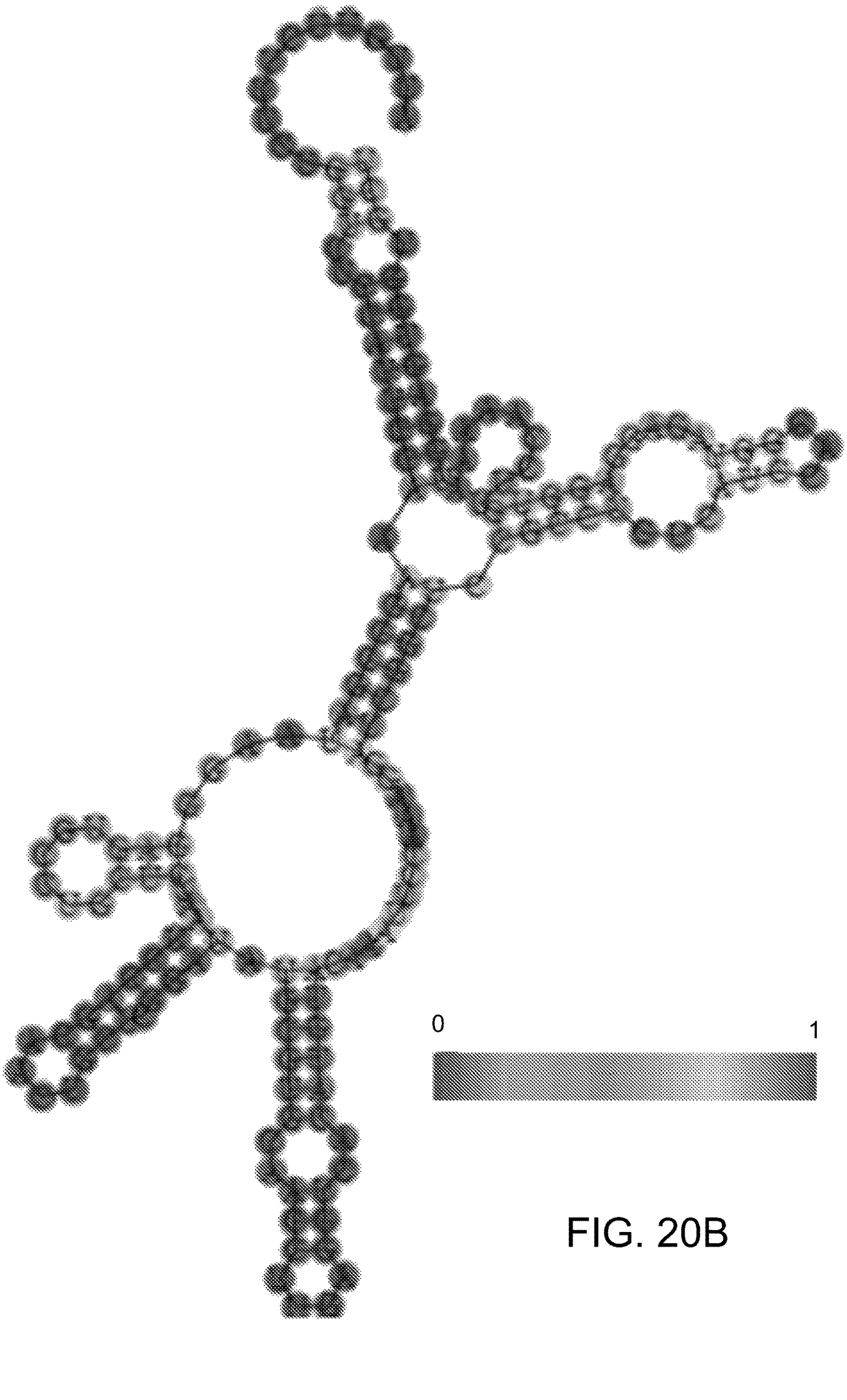
Figure 20C:
Figure 20D:
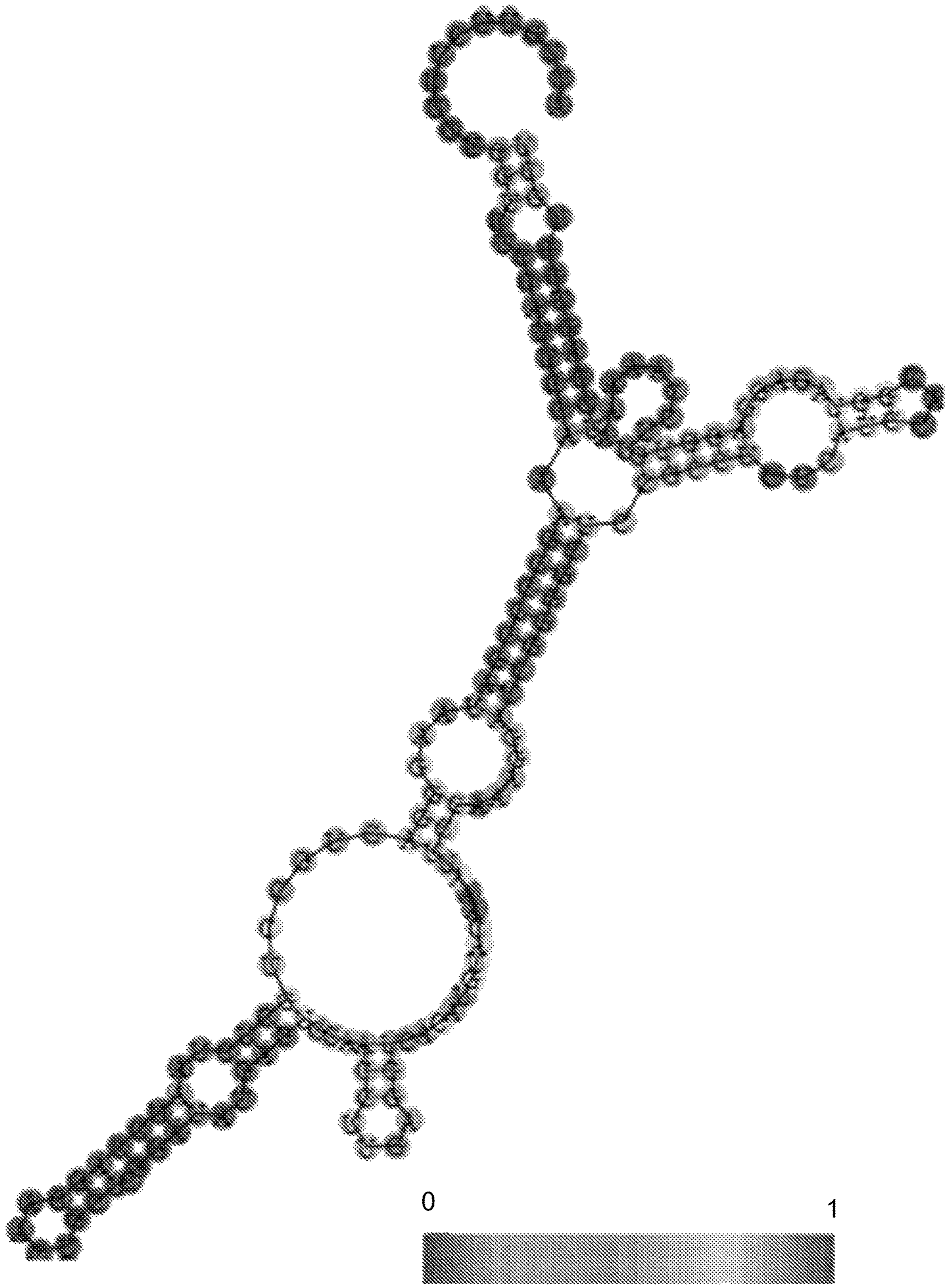
Figure 21A:
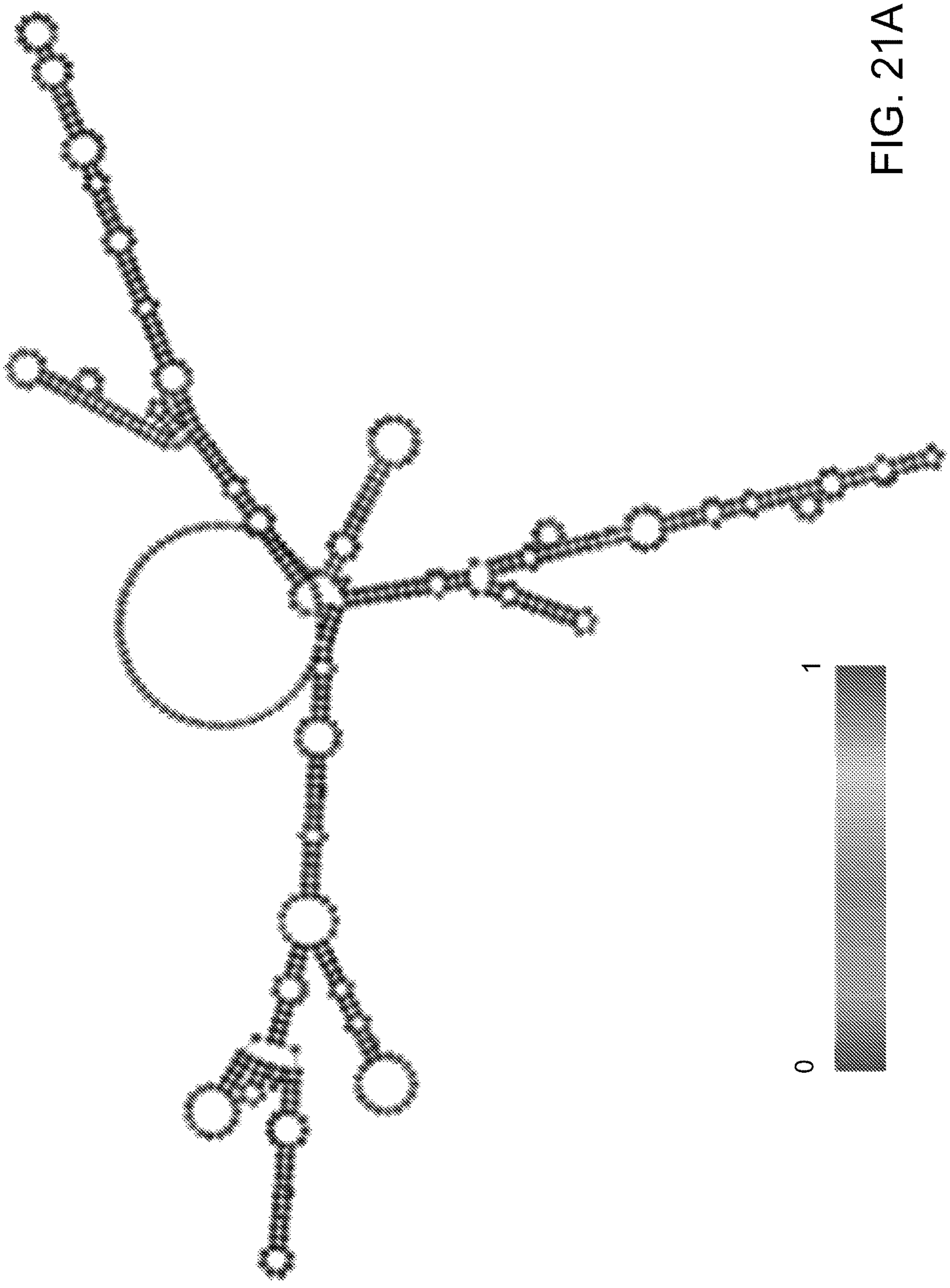
FIG. 21 shows the secondary structure prediction of the RNA sequence of CIR 2. Secondary structure prediction for CIR 2's RNA sequence using the RNAfold program resulted in: 21A) the minimum free energy (MFE) structure for CIR 2 with the poly U tail, 21B) the centroid RNA structure for CIR 2 with the poly U tail, 21C) the minimum free energy (MFE) structure for CIR 2 with the exclusion of the poly U tail, and 21D) the centroid structure for CIR 2 with the exclusion of the poly U tail. The shade bar is for base-pairing probabilities; areas in dark gray are least likely while areas of light gray are most likely.
Figure 21B:
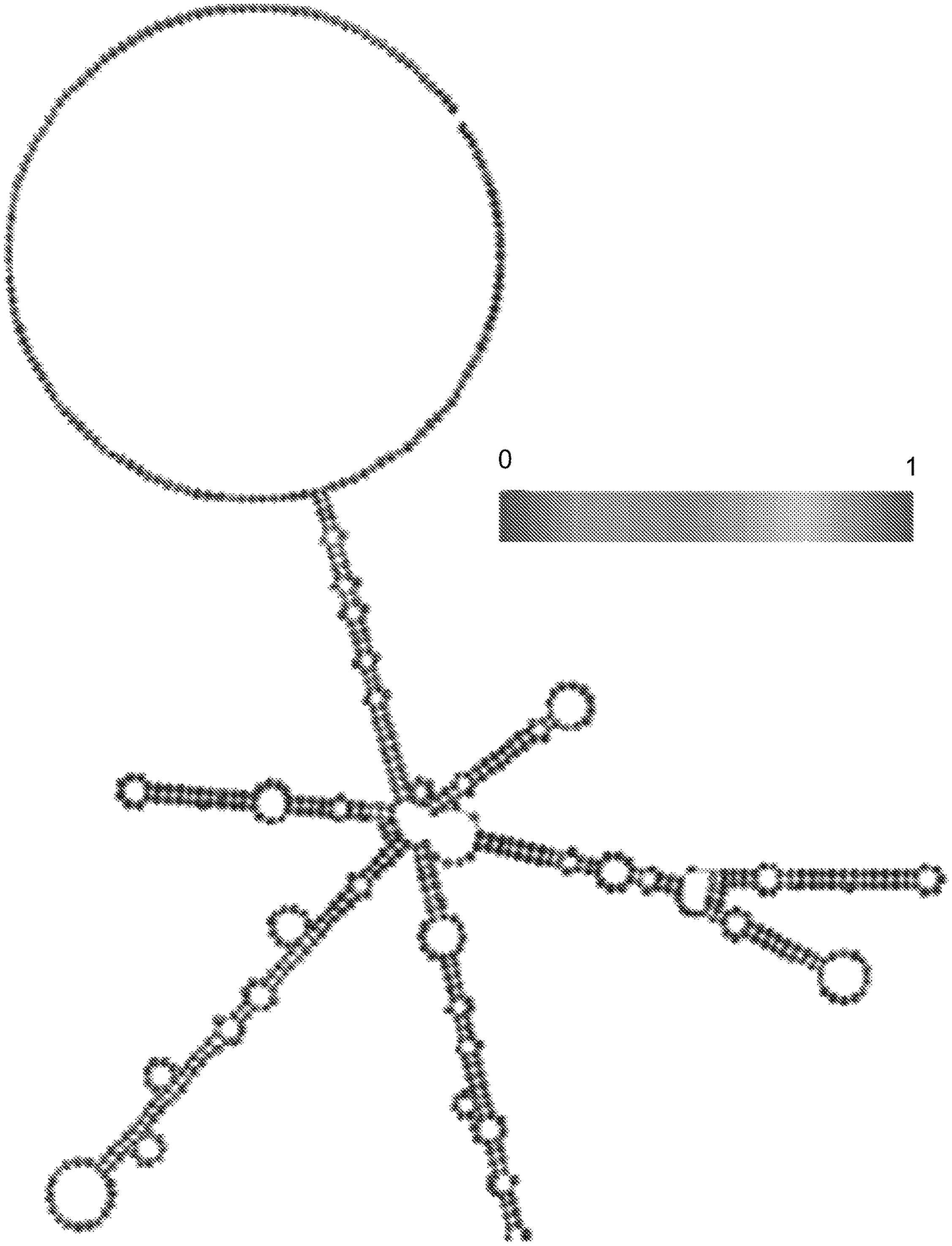
Figure 21C:
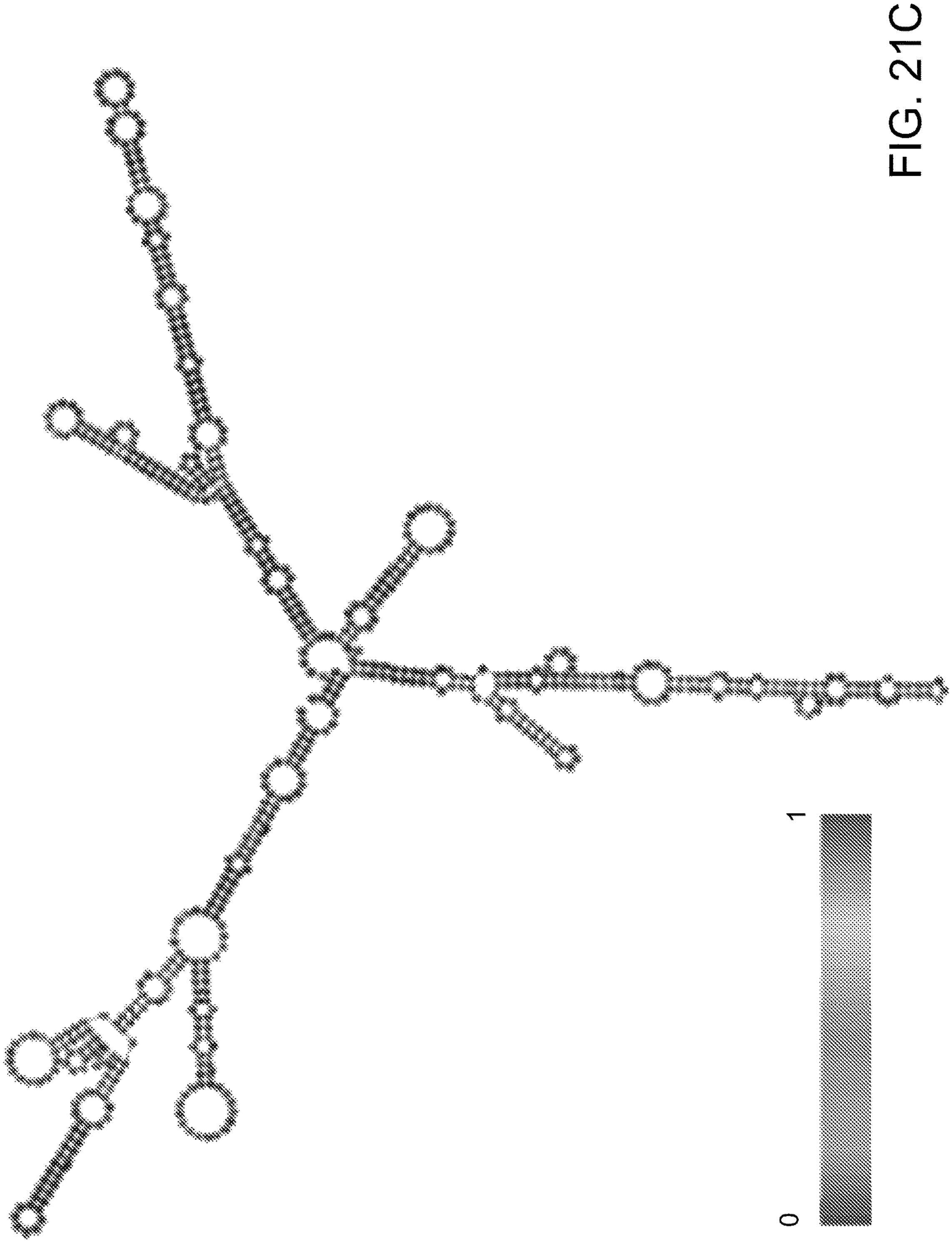
Figure 21D:
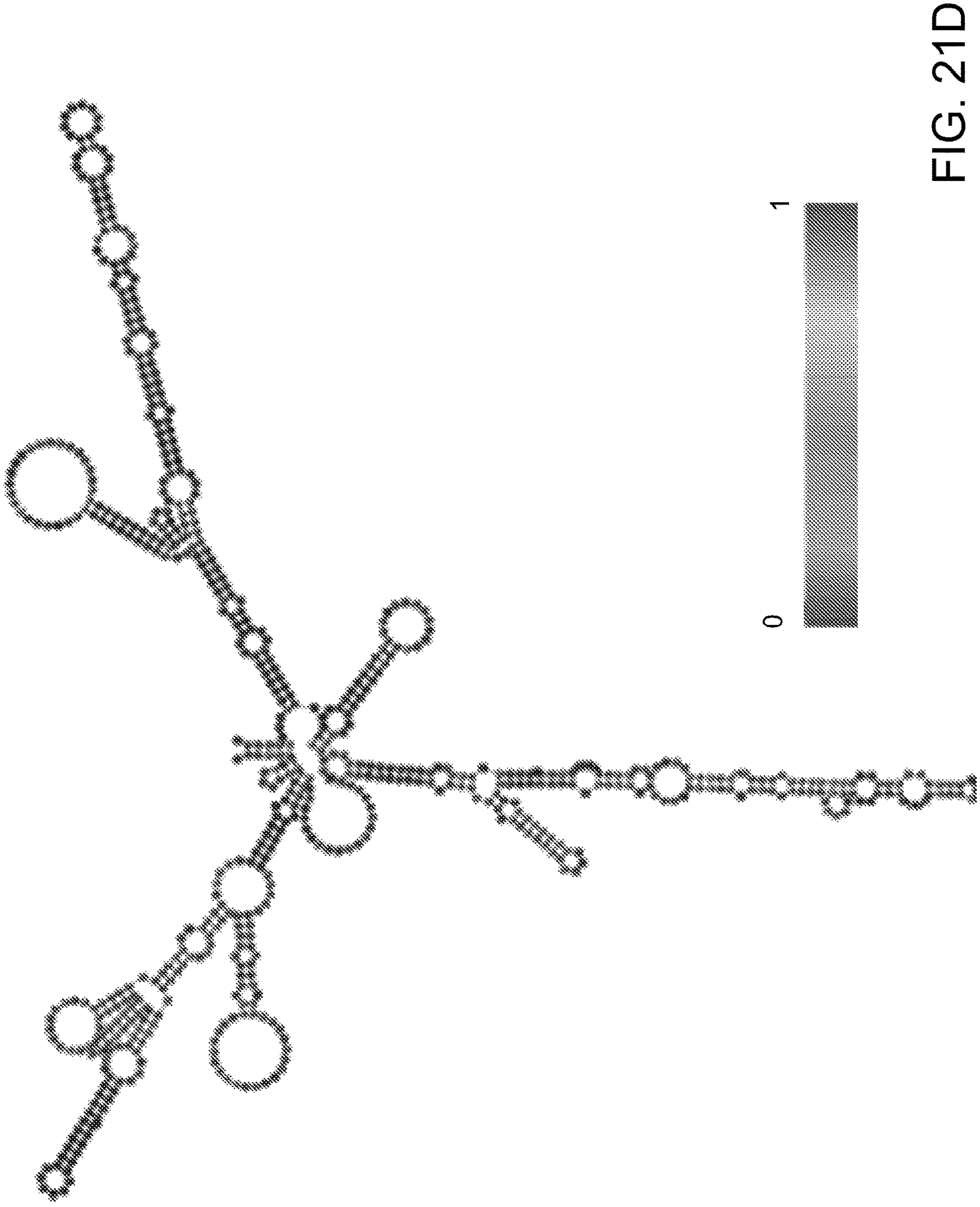

The DNA sequence of CIR 2 was also entered into a NCBI conserved domain search and revealed that the sequence is associated with the COX2 (FIG. 18). This information further supports the idea that the DNA sequence obtained for CIR 2 is linked to the mitochondrial gene for cytochrome c oxidase subunit II. The DNA sequence was then converted into the following RNA sequence using a sequence converter (SEQ ID NO. 16):

```
GGCUCUAGAGGGGGUAGAGGGGGUGCUAUAGGGUAAAUACGGGCCCUAUU
UCAAAGAUUUUUAGGGGAAUUAAUUCUAGGACGAUGGGCAUGAAACUGU
GGUUUGCUCCACAGAUUUCAGAGCAUUGACCGUAGUAUACCCCCGGUCGU
GUAGCGGUGAAAGUGGUUUGGUUUAGACGUCCGGGAAUUGCAUCUGUUUU
UAAGCCUAAUGUGGGGACAGCUCAUGAGUGCAAGACGUCUUGUGAUGUAA
UUAUUAUACGAAUGGGGGCUUCAAUCGGGAGUACUACUCGAUUGUCAACG
UCAAGGAGUCGCAGGUCGCCUGGUUCUAGGAAUAAUGGGGGAAGUAUGUA
GGAGUUGAAGAUUAGUCCGCCGUAGUCGGUGUACUCGUAGGUUCAGUACC
AUUGGUGGCCAAUUGAUUUGAUGGUAAGGGAGGGAUCGUUGACCUCGUCU
GUUAUGUAAAGGAUGCGUAGGGAUGGGAGGGCGAUGAGGACUAGGAUGA
```

-continued

UGGCGGGCAGGAUAGUUCAGACGGUUUCUAUUUCCUGAGCGUCUGAGAUG

UUAGUAUUAGUUAGUUUUGUUGUGAGUGUUAGGAAAAGGGCAUACAGGA

CUAGGAAGCAGAUAAGGAAAAUGAUUAUGAGGGCG.

With the DNA poly A tail attached the following RNA sequence contains a poly U tail (SEQ ID NO. 15):

UUUUUUUUUUUUUUUUUUUUUUUUUUUUUUUUUUUUUUUUUUUUUUUU

UUUUUNUUUGGCUCUAGAGGGGGUAGAGGGGGUGCUAUAGGGUAAAUA

CGGGCCCUAUUUCAAAGAUUUUUAGGGGAAUUAAUUCUAGGACGAUGGGC

AUGAAACUGUGGUUUGCUCCACAGAUUUCAGAGCAUUGACCGUAGUAUAC

CCCCGGUCGUGUAGCGGUGAAAGUGGUUUGGUUUAGACGUCCGGGAAUUG

CAUCUGUUUUUAAGCCUAAUGUGGGGACAGCUCAUGAGUGCAAGACGUCU

UGUGAUGUAAUUAUUAUACGAAUGGGGGCUUCAAUCGGGAGUACUACUCG

AUUGUCAACGUCAAGGAGUCGCAGGUCGCCUGGUUCUAGGAAUAAUGGGG

GAAGUAUGUAGGAGUUGAAGAUUAGUCCGCCGUAGUCGGUGUACUCGUAG

GUUCAGUACCAUUGGUGGCCAAUUGAUUUGAUGGUAAGGGAGGGAUCGUU

GACCUCGUCUGUUAUGUAAAGGAUGCGUAGGGAUGGGAGGGCGAUGAGGA

CUAGGAUGAUGGCGGGCAGGAUAGUUCAGACGGUUUCUAUUUCCUGAGCG

UCUGAGAUGUUAGUAUUAGUUAGUUUUGUUGUGAGUGUUAGGAAAAGGG

CAUACAGGACUAGGAAGCAGAUAAGGAAAAUGAUUAUGAGGGCG

The possible secondary structures of the full length axolotl MIR, full length mutant axolotl MIR, active region of the axolotl MIR, active region of the mutant axolotl MIR, the RNA sequence for CIR 2 with the poly U tail, and the RNA sequence for CIR 2 without the poly U tail were determined using the RNAfold and Genebee RNA secondary structure prediction models (FIGS. 9, 13, 19-21).

Example 13: Mutant Axolotl Heart Bioassays to Identify Active Human RNA Clones As described herein a specific human fetal heart RNA has been discovered, which has the ability to induce myocardial cell formation from mouse embryonic and human induced pluripotent stem cells in culture. In this study, commercially-obtained RNA from human fetal heart was cloned, sequenced and synthesized using our standard laboratory approaches. The stem cells were allowed to form embryoid bodies (EB) in hanging drops, then plated on cultured dishes and transfected with the RNA. Differentiation into cardiomyocytes was evaluated by morphological observation as well as confocal microscopy after immunofluorescent staining for the cardiac specific proteins, cardiac troponin-T, as well as the general muscle proteins tropomyosin and α-actinin. Molecular analyses of the specific fetal Cardiac-Inducing RNA (CIR), revealed that it is a fragment of N-sulphoglucosaminesulphohydrolase and the capase recruitment domain family member 14 precursor. Stem cells transfected with CIRs often form into spindle-shaped cells characteristic of cardiomyocytes, and express the cardiac specific contractile protein marker, troponin-T, in addition to tropomyosin and a-actinin as detected by immunohistochemical staining. Expression of these contractile proteins showed organization into sarcomeric myofibrils characteristic of striated cardiac muscle cells. Computer analyses of the RNA secondary structures of the active MIR previously-evaluated axolotl and the active cloned fetal human heart RNA demonstrates significant similarities in their secondary structures and both promote the mouse embryonic or human induced pluripotent stem cells to differentiate into definitive cardiac muscle cells. Thus, these two RNAs, MIR and the newly-discovered human cloned RNA (CIR), described here, appear to have evolutionarily conserved secondary structures suggesting that both play major roles in vertebrate heart development and, particularly, in the differentiation of cardiomyocytes from non-muscle cells during development.

Methods: qRT-PCR:

RNA was extracted using a NucleoSpin RNAII Kit (Macherey-Nagel, Bethlehem, Pa., USA) from differentiated cells treated with the active RNA, and one control untreated (treated only with lipofectamine). qRT-PCR was performed with a Rotor-Gene machine using a Rotor-Gene SYBR PCR kit (Qiagen #204074, Valencia, Calif., USA) with primers as designed in our earlier studies (Zhang et al., 2009).

Sequencing and Secondary Structure Prediction:

Specific RNA molecules were determined to have rescuing abilities initially by using our mutant axolotl heart bioassay system (Zhang et al., 2009). That specific cloned RNA then was sent to Functional Biosciences (Madison, Wis.) to determine its original DNA sequence.

The DNA sequence associated with the rescuing RNA was screened for vector contamination using the protocols on NIH website www.ncbi.nlm.nih.gov and then it was trimmed to remove contamination. The online NCBI BLAST program was utilized to determine the exact sequence within the human genome and the sequence editor database at www.fr33.net was used to convert the DNA sequence into the RNA sequence. The resulting RNA sequence was entered into the Genebee RNA computational software secondary structure prediction program developed in the Belozersky Institute at Moscow State University, Russia. This software was used to predict likely secondary structures for the RNA. The RNA's secondary structure was then compared to the secondary structure of the axolotl MIR to determine similarities.

Results:

Initial bioassays were conducted by combining and pooling groups of RNAs in which mutant salamander non-beating hearts were organ cultured (Moses-Arms et al., 2014). Control experiments involved organ culturing mutant hearts with no treatment and normal hearts with and without treatment. Pooled RNA groups that caused the treated mutant hearts to begin beating by the 2nd-4th day of treatment were separated into smaller testing groups until each individual RNA had been checked for rescuing ability. Within the 396 clones tested, one clone that showed significant rescuing ability and caused the non-beating mutant hearts to beat vigorously was clone #6 (now called Cardiac Inducing RNA or CIR). In the present study, we describe and characterize the CIR derived from clone #6 and test for the CIR's ability to promote the differentiation of nonmuscle mouse embryonic and human induced pluripotent stem cells into definitive cardiomyocytes.

Confocal Microscopy of Positive Control Axolotl Hearts

Figure 3B:
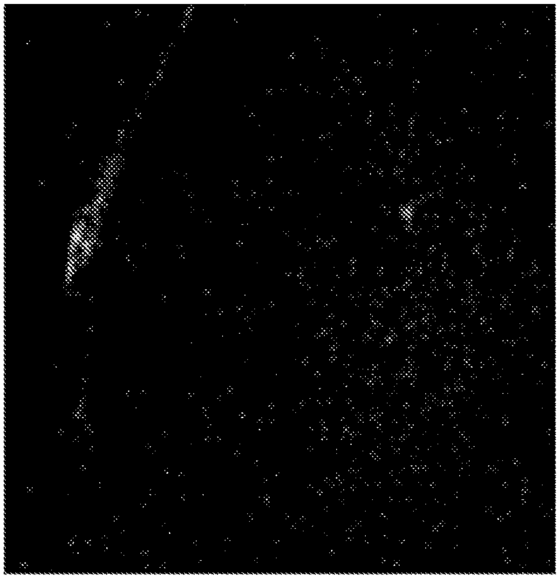
Figure 3A:
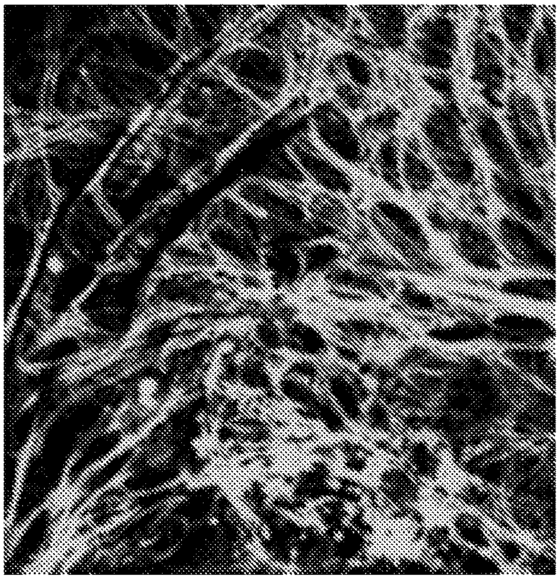

Analysis of normal axolotl embryonic hearts show well-organized sarcomeric myofibrils (FIG. 3A) with antibody staining for tropomyosin. Untreated mutant hearts cultured in Holtfreter's solution without CIR treatment showed virtually no staining with anti-tropomyosin antibodies and no myofibrillar structures could be identified in these untreated mutant hearts (FIG. 3B). Mutant axolotl hearts treated with the CIR fetal heart human RNA showed well-organized myofibrils to the extent that these rescued mutant myocardial cells (FIG. 3C) appeared indistinguishable from the normal control hearts (compare FIGS. 3A and 3C). Thus, the CIR clearly has promoted the differentiation of cardiac mutant axolotl hearts cells from a non-muscle, non-cardiac phenotype into normally-appearing, virgorously-contracting cardiac muscle cells containing myofibrils of normal morphology. The cardiac inducing RNA (CIR) derived from clone #6 rescues the mutant embryonic axolotl hearts in a manner very similar to the myofibril inducing RNA (MIR) derived from normal (+/+ or +/c) axolotl embryos that has been previously described (Zhang et al. 2009). It is very clear that the axolotl MIR and the human clone #6 CIR serve as functional homologs in the cardiac mutant axolotl rescue bioassay and both RNAs have the ability to promote the differentiation of beating cardiac tissue from non-muscle cells.

Sequencing and Secondary Structure of the Active Clone

PCR products and plasmids containing the DNA that corresponded to the CIR (clone #6 RNA) were sent to Functional Biosciences (Madison, Wis., USA) for determination of its DNA sequence (FIG. 24A). The trimmed DNA sequence was entered into the online NCBI BLAST program to determine to what protein the sequence coded and it was identified as a fragment of N-sulphoglucosamine sulphohydrolase and the caspase recruitment domain family member 14 precursor. Using a sequence converter, the DNA sequence was converted to the corresponding RNA sequence (FIG. 24B).

Figure 25A:
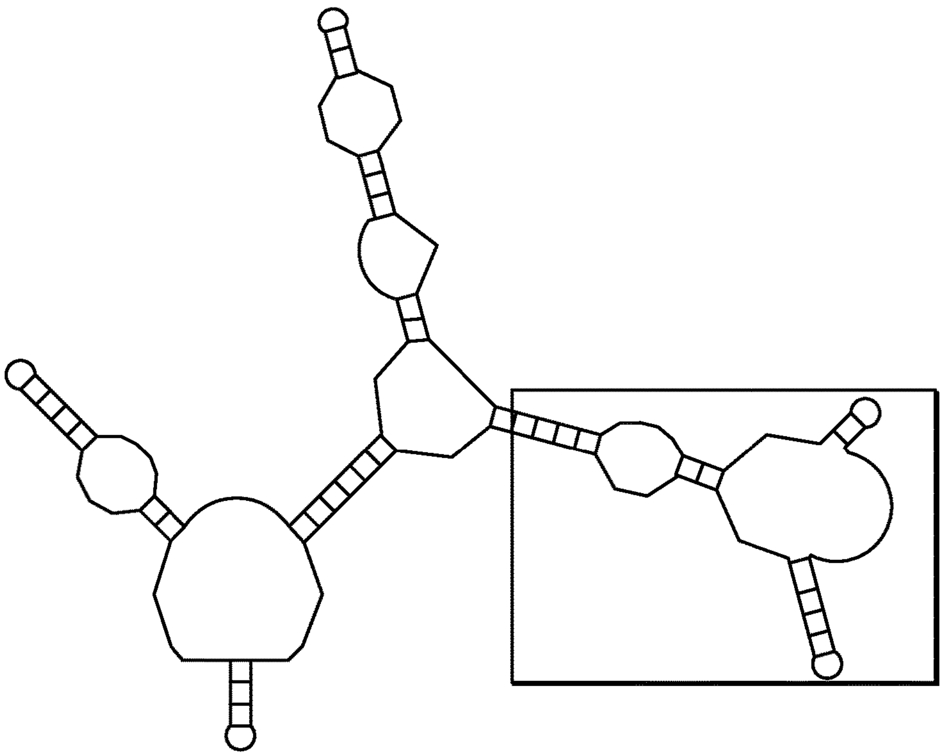
FIG. 25 shows the secondary structures of CIR (FIG. 25A), active normal salamander MIR (FIG. 25B) and non-active mutant MIR (FIG. 25C). The CIR and active normal salamander MIR have regions of similar structure as part of their structure. Both differ from the non-active mutant RNA. Comparable areas are shown in boxes.
Figure 25B:
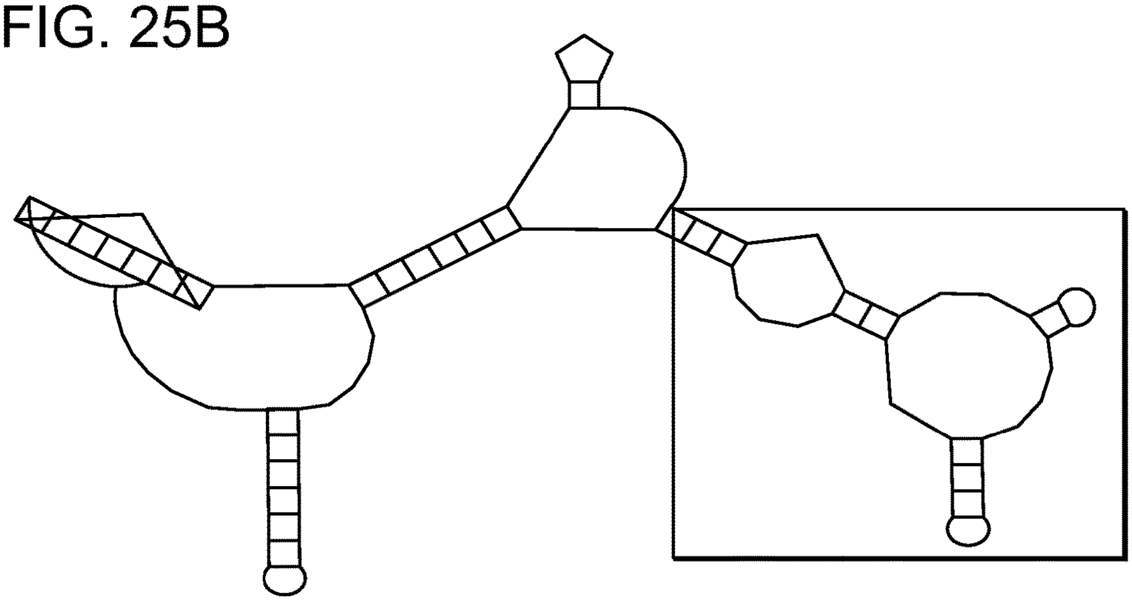
Figure 25C:
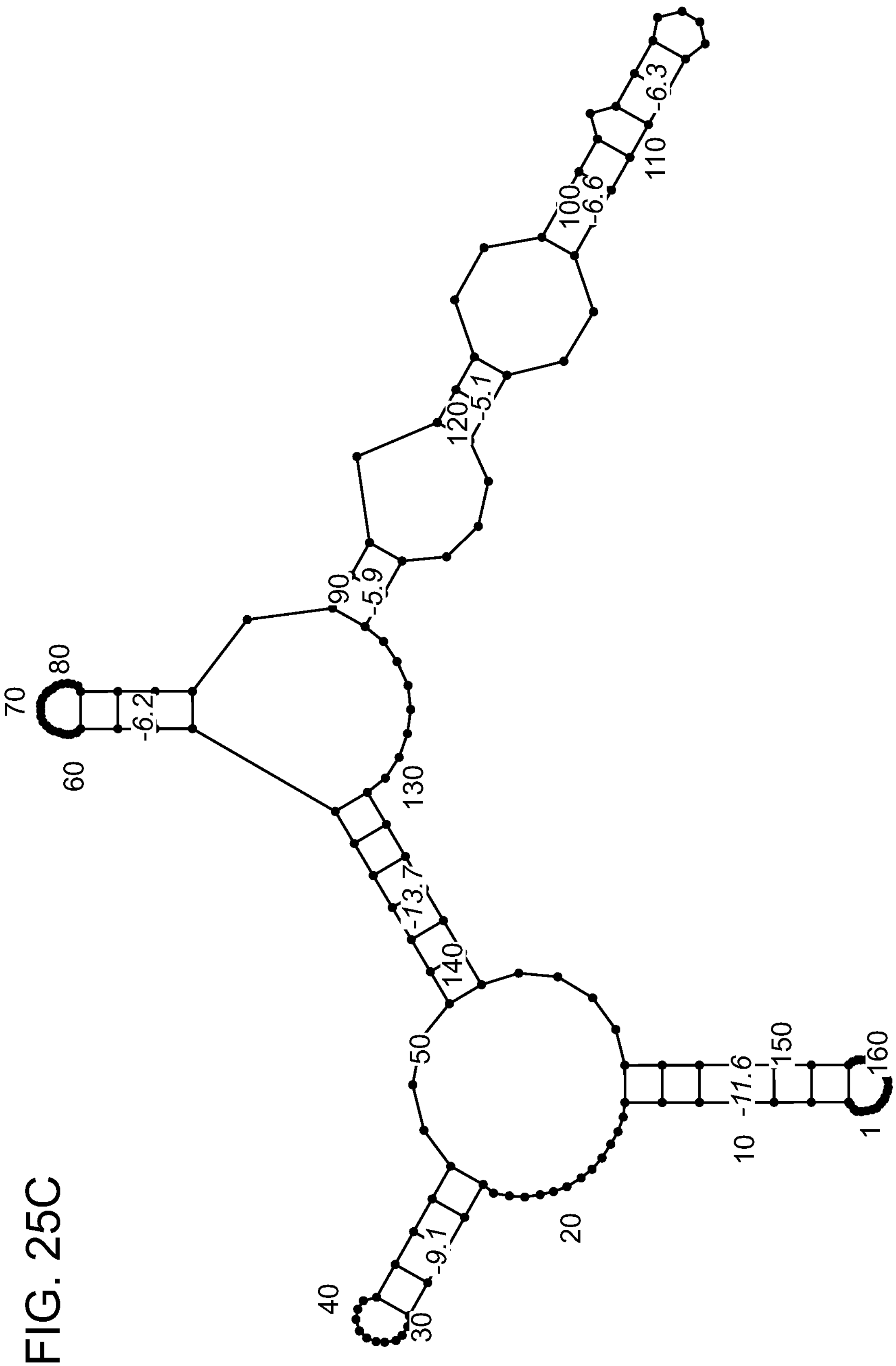

The possible secondary structures of the comparable regions of the human CIR (FIG. 25A), the normal axolotl MIR (FIG. 25B) and the mutant axolotl MIR (FIG. 25C) were determined using the Genebee RNA secondary structure prediction model. In comparing the active CIR from human (FIG. 25A) and the active MIR from normal (+/+ and +/c) axolotl (FIG. 25B), which have very similar secondary structures, with the non-active c/c mutant axolotl MIR (FIG. 25C), both human and normal axolotl have major differences in secondary RNA structure from the mutant. The human CIR and normal MIR both promote myofibril formation in and rescue mutant hearts. The c/c mutant RNA, with its significantly different secondary structure, lacks the capability of promoting myofibrillogenesis and rescuing the mutant hearts. Thus, the secondary structures of the RNAs appear to be a critical factor in the human CIR's and the normal axolotl MIR's ability to rescue the mutant hearts.

Example 14: Analysis of CIR (Cardiac-Inducing RNA) in Promoting Cardiomyocyte Differentiation from Mouse Embryonic Stem Cells and Human Induced Pluripotent Stem Cells Methods: Stem Cell Culture and Differentiation Protocol:

Human induced pluripotent stem cells (iPSCs), DF19-9-11T.H, from WiCell, Inc., (Madison, Wis., USA) and mouse Embryonic Stem Cells (mESCs), Strain 129, OriCell from Cyagen Biosciences, Inc. (Santa Clara, Calif., USA) were incubated and grown at 37° C. in a humidified 5% $CO_2$ atmosphere (FIGS. 22A, 22B), and passaged routinely according to our routine protocols (Lemanski et al., 2012). These cells express the Oct-3/4 pluripotency factor (FIG. 6A) colocalized in the nuclei as shown with DAPI staining (FIG. 6B). To generate embryoid bodies, small drops of cell suspensions of 20 μL volume were placed by micropipette on the inner surface of a Petri dish lid and cultured for 24 h (FIG. 23A). On the second day, the cells were clumped in embryoid bodies (EBs) (FIGS. 23B, 23C). EBs were washed by medium and transferred to gelatin-coated dishes. In a few days EBs attached to the surface and cells started to proliferate and spread (FIG. 23D). To induce differentiation, cells were transfected with active clones of RNA mixed with the transfection reagent, Lipofectamine RNAiMAX, (Life Technologies, Grand Island, N.Y., USA), diluted to a concentration of 50 ng/μl in OPTI-MEM medium (Life Technologies) and incubated for 6 hours.

Fixation, Staining, and Confocal Microscopy of Cultured Stem Cells:

Cardiac Inducing RNA (CIR)-treated and non-inducing RNA treated or untreated control cells in culture were fixed in 4% paraformaldehyde for 30 min, rinsed in PBS with 3% BSA for 3 min, permeabilized in 0.1% Tween-20 and 3% BSA and stained with primary antibody diluted 1:75 with PBS overnight. The cells were then rinsed with PBS and 3% BSA for 3 min and stained with the secondary antimouse antibody diluted to 1:75 with PBS for 1 hr. The cells were immunofluorescently stained for tropomyosin, cardiac troponin T or a-actinin. The primary antibodies used for all three proteins were monoclonal antibodies from mouse and the secondary antibodies were Goat F(ab) anti-mouse polyclonal antibodies with a Fluorescein isothiocyanate (FITC) tag excited at 490 nm (Abcam, Cambridge, Mass., USA). The cells were analyzed using a confocal microscope to identify and localize the presence of tropomyosin, cardiac troponin-T and α-actinin in the cells, including these proteins present in organized sarcomeric myofibrils. The immunofluorescently-stained cells were analyzed using an Olympus BX62 scanning laser confocal microscope.

Figures 26A, 26B, 26C, 26D:
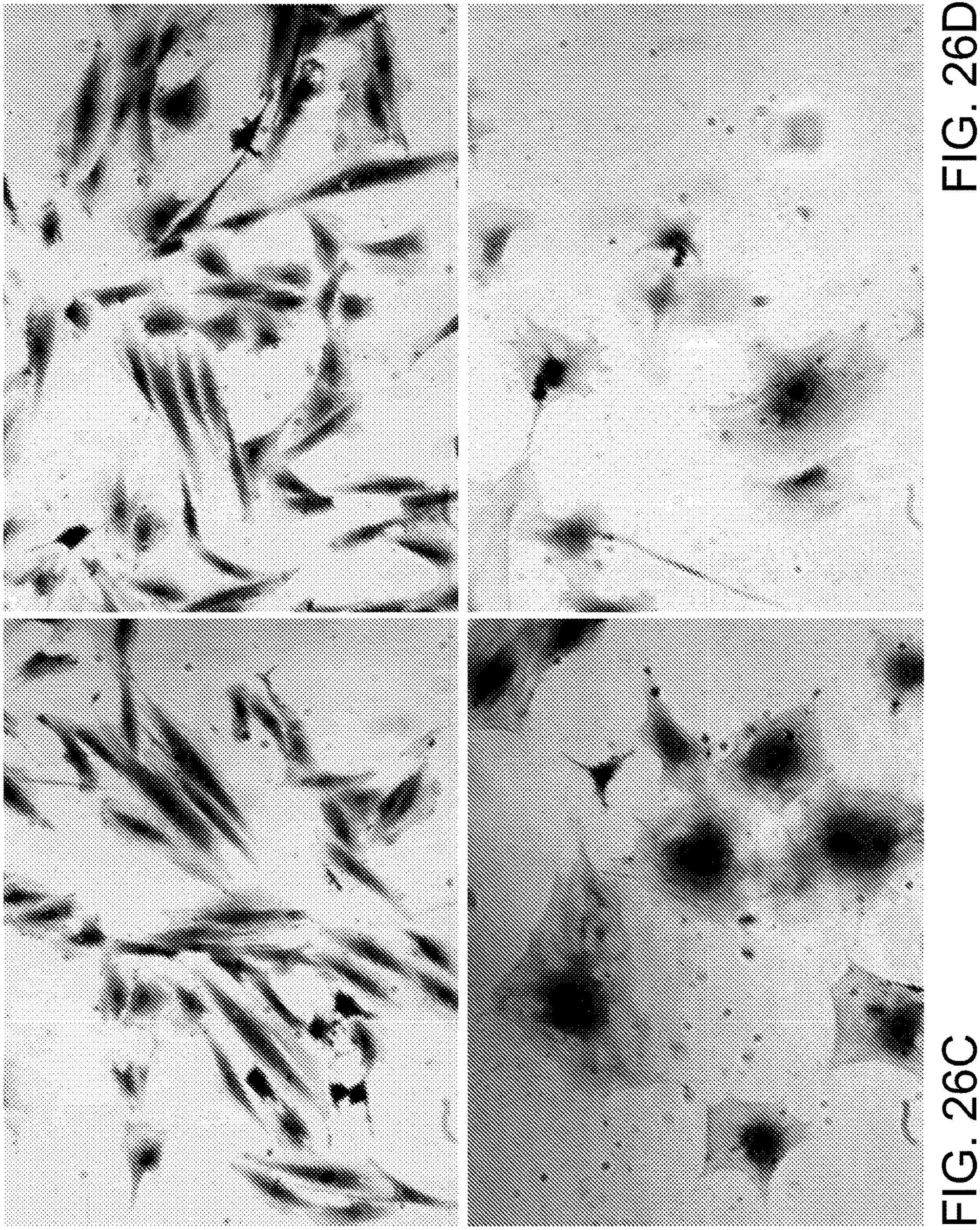
FIG. 26 shows human iPSCs (FIG. 26A) and mouse ESCs (FIG. 26B) differentiated into spindle-shaped cardiomyocytes after transfection with CIR; human iPSCs (FIG. 26C) and mouse ESCs (FIG. 26D) control without transfection.
Figures 27A, 27B, 27C, 27D:
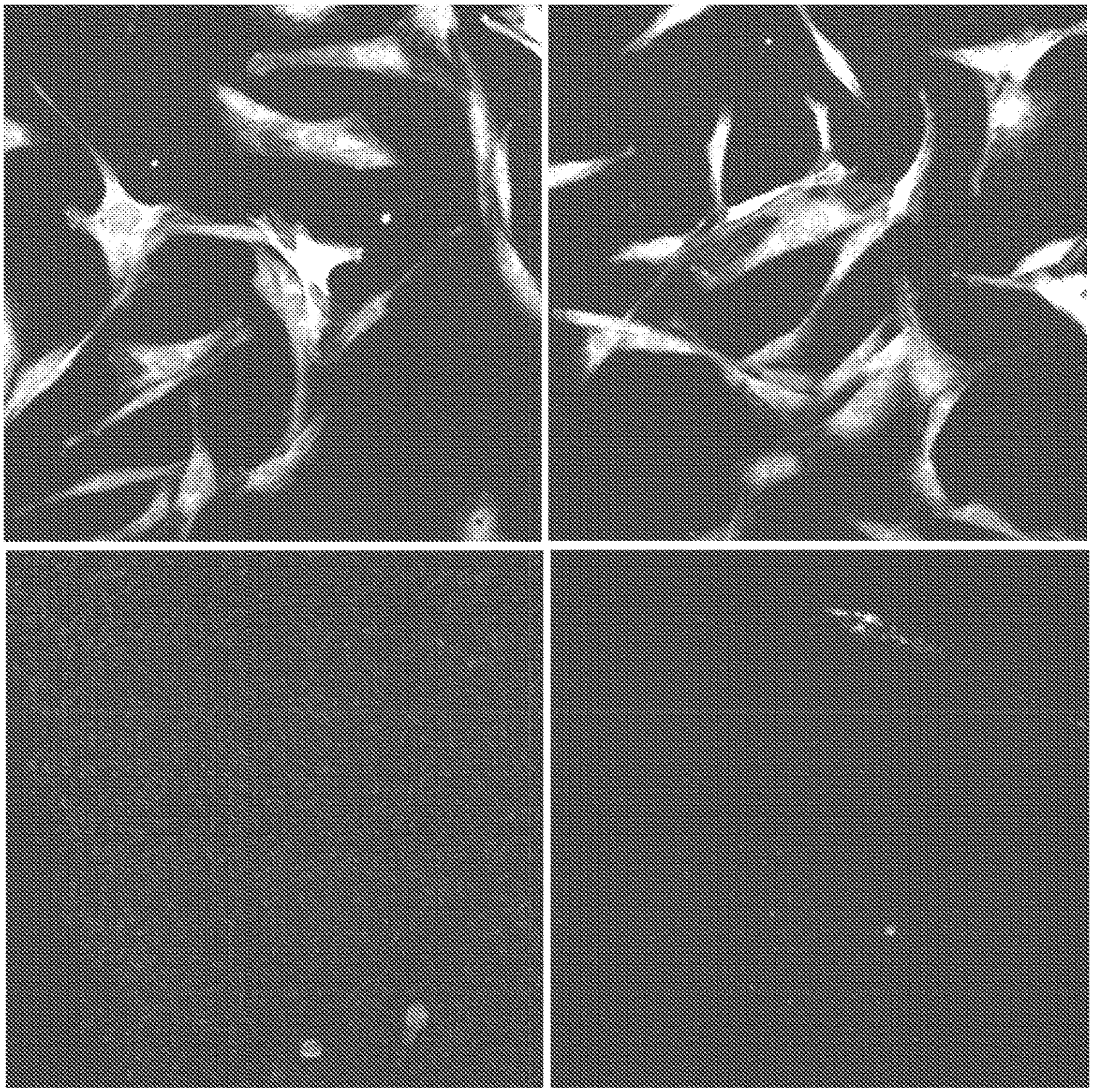
FIG. 27 shows human iPSCs (FIG. 27A) and mouse ESCs (FIG. 27B) derived cardiomyocytes after transfection with CIR; human iPSCs (FIG. 27C) and mouse ESCs (FIG. 27D) control, without transfection.
Figure 28C:
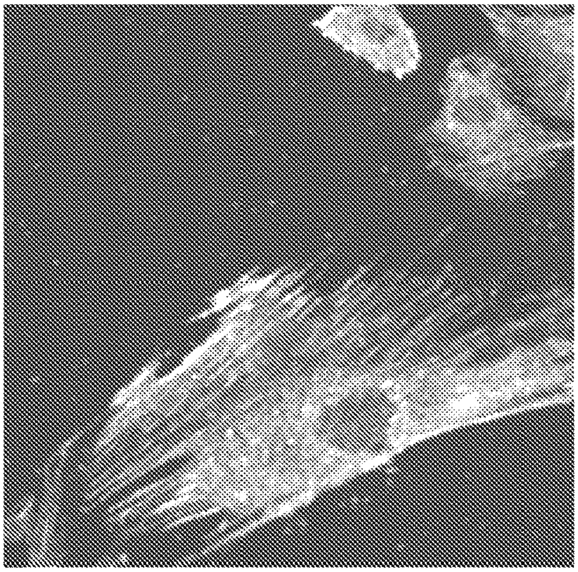
FIG. 28 shows differentiated cardiomyocytes derived from human induced pluripotent stem cells stained with antibodies against cardiac specific troponin T (FIG. 28A), tropomyosin (FIG. 28B) and alpha-actinin (FIG. 28C). Similar results were obtained with mouse embryonic stem cells. Without CIR treatment, very few (9-10%) cardiomyoctye-like cells were evident.
Figure 28B:
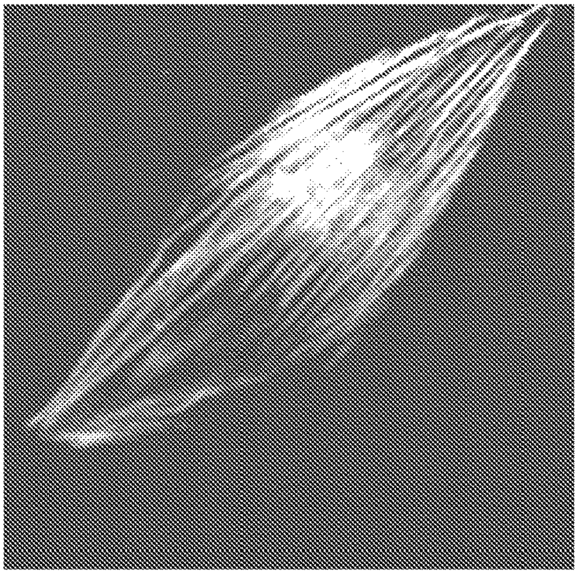
Figure 28A:
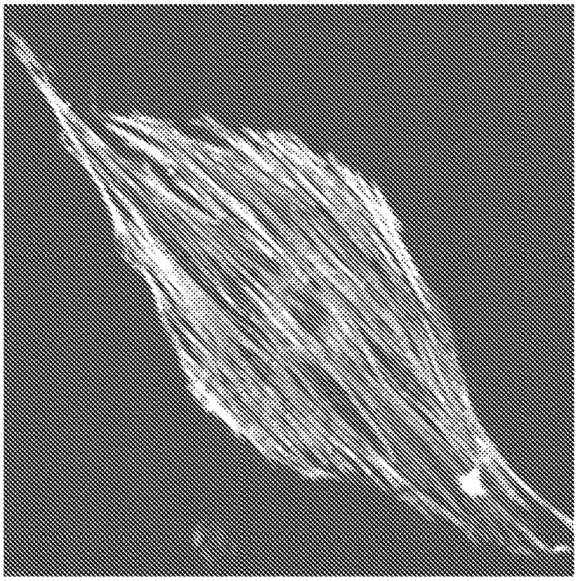

Results:

Spontaneous cardiomyocyte differentiation of mouse and human stem cells has been described previously by Mummery et al, 2002 [2]. In the present study, stem cells were differentiated into cardiomyocytes after formation of embryoid bodies (EBs) by culturing in the presence of CIR. We tested this approach and found that spontaneous "background" cardiomyocyte differentiation without RNA treatment was approximately 9-10%. We passaged stem cells and plated them into small drops as "hanging drops" on Petri dish lids and incubated them for two days. On the second day, stem cells aggregated and formed embryoid bodies (EBs). We plated the EBs on collagen coated dishes and allowed them to attach. Cells from EBs started to grow and proliferate. At this stage we treated them with the CIR and in 7-8 days, 70-80% had differentiated into spindle-shaped cardiomyocytes (FIGS. 26A, 26B) and expressed cardiac specific troponin T as revealed by antibody staining methods (FIGS. 27A, 27B). Non-treated control human iPSCs or mouse ESCs showed only 9-10% of the cells with morphological cardiac traits (FIGS. 26C, 27D) at this 7-8 day stage in culture and there was very little detectable cardiac-staining for cardiac troponin T in any of the non-treated human or mouse stem cells (FIGS. 27C, 27D).

Figure 29B:
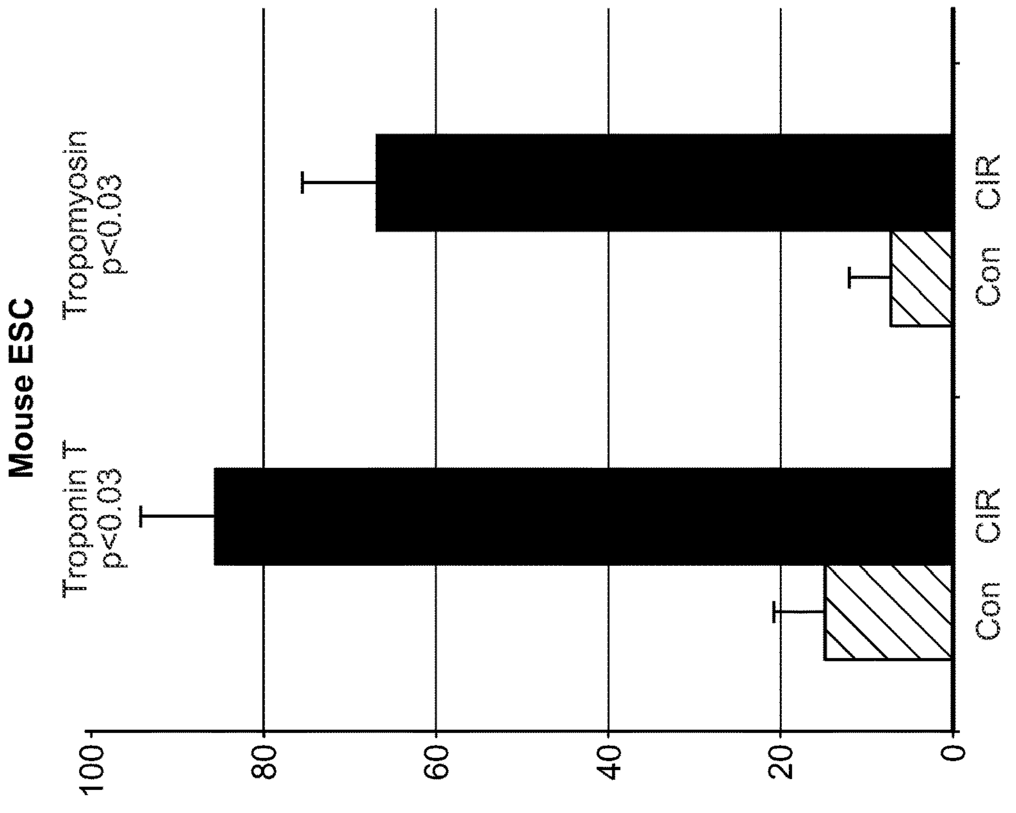
FIG. 29 shows the expression of cardiac-specific mRNA quantified with qRT-PCR in human iPSCs (FIG. 29A) and mouse ESCs (FIG. 29B) derived cardiomyocytes after transfection with CIR compared with control (Con); $p<0.03$.
Figure 29A:
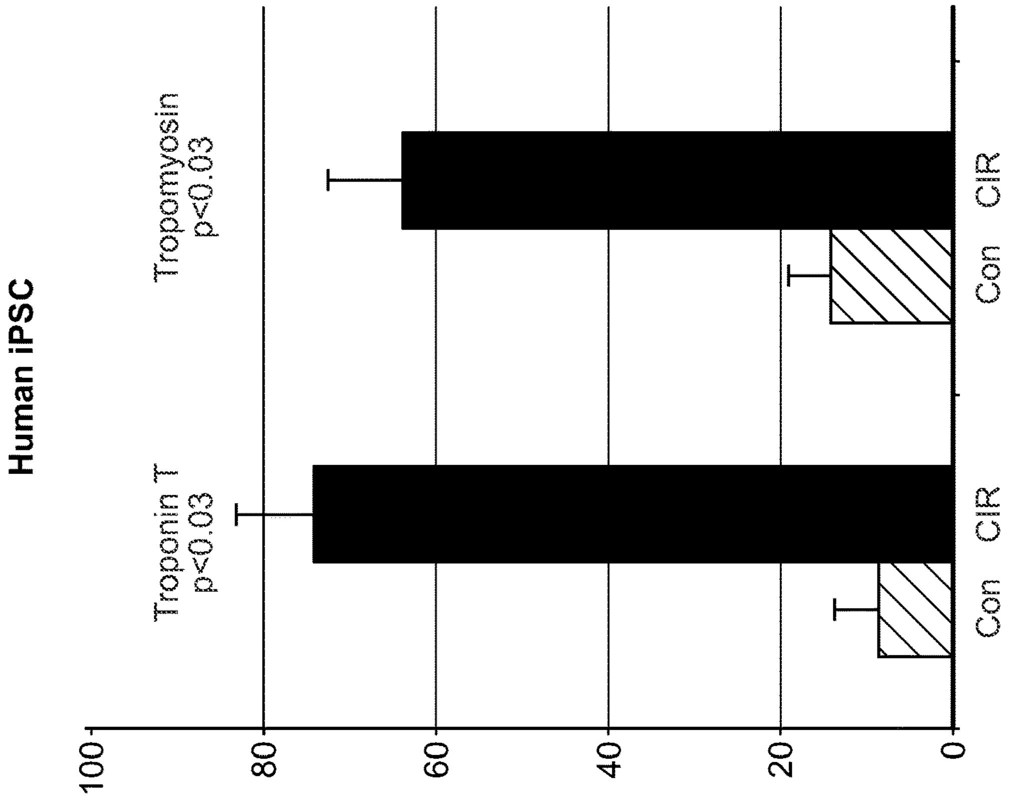

High resolution confocal imaging illustrated sarcomeric myofibril organization in the stem cell-derived cardiomyocytes from human induced pluripotent stem cells (iPSCs) and from mouse embryonic stem cells (ESC) transfected with active CIR when stained with antibodies against cardiac specific troponin T, tropomyosin or alpha-actinin. (FIG. 9A,B,C). When the RNAs from stem cell-derived cardiomyocytes and from non-differentiated stem cells were extracted and expression of cardiac specific mRNA quantified with qRT-PCR (FIG. 29), it was shown that the CIR treatment very significantly increased expression of the cardiac markers, cardiac troponin T and tropomyosin, in comparison with the untreated cells in ESC or iPSC. The expression of cardiac specific troponin T in human stem cells and mouse embryonic stem cells far exceeded the expression in untreated mouse or human cells. In fact, it was in the range of 7-8 fold higher in the CIR-treated cells after only 7-8 days in culture (FIG. 29). Tropomyosin was also significantly higher in the CR-treated stem cells, approximately 5-fold higher (FIG. 29).

Also, when we screened the cloned sequence in the human genome with BLAST at the NCBI database, we found two high score matches with a portion of exon 8 of the human N-sulfoglucosaminesulfohydrolase (SGSH) gene on the sense strand of DNA and with the caspase recruitment domain family, member 14 (CARD14), on the antisense strand. These genes, SGSH and CARD14, partially overlap and belong to opposite DNA strands (forward and reverse) on human chromosome 17.

Discussion:

We have discovered a specific RNA, originally identified from commercially obtained human fetal heart RNA, that has the ability to turn non-muscle cells into definitive cardiomyocytes. This was accomplished by initially preparing 396 human fetal RNA clones and analyzing them in pooled groups to evaluate their ability to promote myocardial cell formation using our published cardiac mutant axolotl heart rescue bioassay system. After these initial experiments to confirm the positive cardiomyogenic effect of clone #6, RNA (now called Cardiac Inducing RNA or CIR, SEQ ID NO. 1), we tested CIR on mammalian stem cells in culture, both mouse embryonic stem cells (ESC) Cyagen Biosciences, Inc (Santa Clara, Calif. USA) and human induced pluripotent stem cells (iPSC) purchased from WiCell, Inc. (Madison, Wis., USA). In the present study, our results confirm that CIR has the ability to promote the differentiation of both Mouse embryonic and human induced pluripotent stem cells into definitive cardiac muscle cells. Immunoflourescent confocal microscopy demonstrates the presence of cardiac myofibrils that contain cardiac-specific troponin-T as well as tropomyosin in 70-80% of the CIR treated cells. In addition, CIR cardiomyocytes often appear spindle-shaped and contain well-organized myofibrils with definitive sarcomeric structures, both strong indicators that these cells indeed are myocardiocytes. Only 9-10% of untreated stem cells express cardiac specific troponin-T and tropomyosin. It is very clear from our results that the CIR has a strong inducing effect in converting these non-muscle stem cells into definitive cardiac muscle cells.

The mechanism for this CIR cardiogenic process will require further analysis to fully understand. However, one interesting observation that suggests a possible mechanism for the action of the CIR relates to our finding that the cloned sequence in the human genome with BLAST at the NCBI database, has two high score matches with a portion of exon 8 of the human N-sulfoglucosaminesulfohydrolase (SGSH) gene on the sense strand of DNA and with the caspase recruitment domain family, member 14 (CARD14), on the antisense strand. These genes, SGSH and CARD14, partially overlap and belong to opposite DNA strands (forward and reverse) on human chromosome 17.

The Caspase recruitment domain (CARD) family was originally characterized based on their involvement in the regulation of caspase activation and apoptosis during inflammation, autoimmune and antiviral responses. CARD protein 14 (CARD14) is a novel CARD-containing protein that belongs to the membrane-associated guanylate kinase (MAGUK) family, a class of proteins that functions as molecular scaffolds for the assembly of multiprotein complexes at specialized regions of the plasma membrane. CARD proteins are associated with caspace-9 which, upon activation, split caspase-3 leading to activation of caspase signaling. Recent studies have found that CARD proteins can also function as components of signaling pathways that lead to activation of the transcription factor NF-κB, which plays a central role in the activation of genes involved in immunity, inflammation, and apoptosis. In unstimulated cells, NF-κB is sequestered in the cytoplasm through interactions with inhibitory IκB proteins. Interestingly, caspase activity was shown to mediate the differentiation of embryonic stem cells by splitting p120 protein. Our data suggests that CIR may function as a signal molecule inducing cardiogenesis including synthesis of cardiac myofilaments and assembly of sarcomeric myofibrils.

Figure 6A:
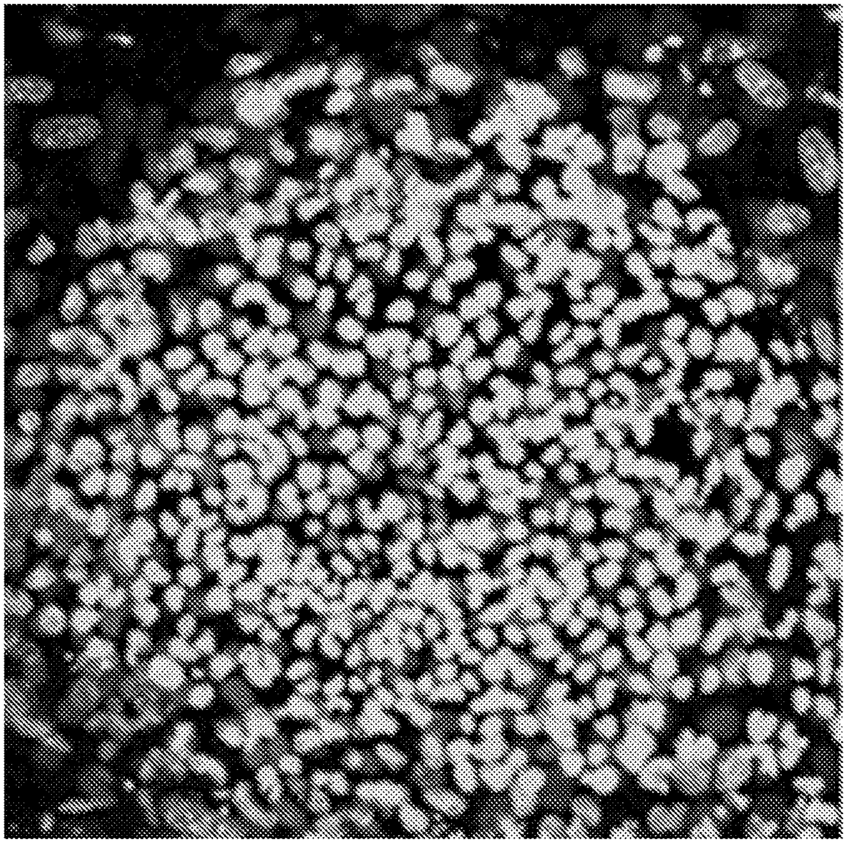

When we compared the sequences of normal axolotl MIR and human CIR, we did not find matches in their sequences, but noted an amazing similarity in their secondary structures generated by using the online computational software GeneBee Program developed at the Belozersky Institute of Moscow State University, Russia (FIG. 6). The human CIR (FIG. 6A) is structurally very similar to the axolotl MIR (FIG. 6B); however, both differ significantly from the non-active mutant MIR (FIG. 6C).

In view of the very significant similarities in secondary structures of the human CIR and the salamander MIR, they likely have the ability to interact with similar regulatory proteins. Thus, these two myocardiogenic RNAs (CIR and MIR) appear to have evolutionarily conserved secondary structures which may be very significant in early embryonic heart development in all vertebrate species, including human. On the basis of our results, we hypothesize that normal human fetal heart expresses CIR, which is a functional homolog of the axolotl MIR, and which is required for human heart development and function. Our results clearly show that if we clone this myocardiogenic RNA (CIR) from human fetal heart and transfect it into mutant axolotl hearts, normal heart development is restored just as with the MIR.

Tropomyosin is an essential protein in sarcomere formation and in muscle contraction. Troponin-T is required to regulate Ca2+-dependent contractions, and has been shown to be essential for sarcomere assembly in cardiac muscle. Increased expression of these mRNAs suggests that the rescue of mutant hearts has taken place when muscle myofilaments start to be expressed and contractile protein assembly into functional sarcomeric myofibrils occurs. The active clone of RNA from human heart, CR, also increased expression of cardiac troponin T and tropomyosin in salamander mutant hearts (FIG. 4). In addition, we treated mouse embryonic and human induced pluripotent stem cells daily for 6 hours with transfection medium containing the active CR. In these experiments, both mouse and human-derived stem cells differentiated into cardiomyocytes in 8 days. Interestingly, during normal in vivo heart embryonic development in mouse, the first cardiac tissue also appears at 8 days post fertilization. Thus, our data clearly and unequivocally demonstrate the ability of the newly-discovered human cardiac-inducing RNA (CIR) to rescue mutant hearts in axolotl embryos, and induce differentiation of both mouse ECS and human iPS cells to differentiate into cardiomyocytes.

Of the 935,000 Americans and many more worldwide, who suffer heart attacks each year, a number are treated by balloon angioplasty, with or without stents, or receive coronary by-pass surgery to reduce their symptoms. While these interventions improve heart function and quality of life for some, many do not significantly recover because connective scar tissue, rather than new muscle, replaces the cardiac muscle in the infarcted area. The findings of the invention may lead to better treatments in the future for patients' recovery from myocardial infarctions or other heart diseases that adversely affect the myocardial muscle tissue. Being able to use the CIR itself, or in combination with induced pluripotent stem cells or fibroblasts derived from that same patient, to repair the damaged muscle tissue or replace the scar tissue with vigorously contracting normal myocardial cells, could lead to a much better prognosis for patients and may very well allow them to return to pre-heart-attack activity levels.

REFERENCES

Bertin J1, Wang L, Guo Y, Jacobson M D, Poyet J L, Srinivasula S M, Merriam S, DiStefano P S, Alnemri E S. CARD11 and CARD14 are novel caspase recruitment domain (CARD)/membrane-associated guanylate kinase (MAGUK) family members that interact with BCL10 and activate NF-kappa B. J Biol Chem 2001; 276(15):11877-82.

Bordzilovskaya N P, Dettlaff T A , Duhon S T, Malacinski G M. (1989) Developmental-stage series of axolotl embryos. In: Armstrong, J. B., and Malacinski, G. M. (Eds), Developmental Biology of the Axolotl. Oxford University Press, New York, 201-219.

Eulalio A, Mano M, Dal Ferro M, Zentilin L, Sinagra G, Zacchigna S, Giacca M. (2012) Functional screening identifies miRNAs inducing cardiac regeneration. Nature 492:376-381.

Fu J D, Rushing S N, Lieu D K, Chan, C W, Kong C W, Geng L, Wilson K D, Chiamvimonvat N, Boheler K R, Wu J C, Keller G, Hajjar R J, Li RA. (2011) Distinct roles of microRNA-1 and -499 in ventricular specification and functional maturation of human embryonic stem cell-derived cardiomyocytes. PLoS One 6:e27417.

"Heart disease facts." (2013). Centers for Disease Control and Prevention. Retrieved Mar. 26, 2013, from http://www.cdc.gov/heartdisease/facts.html Hosoda T, Zheng H, Cabral-da-Silva M, Sanada F, Ide-Iwata N, Ogórek B, Ferreira-Martins J, Arranto C, D'Amario D, del Monte F, Urbanek K, D'Alessandro D A, Michler R E, Anversa P, Rota M, Kajstura J, Leri A. Human cardiac stem cell differentiation is regulated by a mircrine mechanism.Circulation. 2011 Mar. 29; 123(12):1287-96.

Jia, P., C. Zhang, X. P. Huang, M. Poda, F. Akbas, S. L. Lemanski, N. Erginel-Unaltuna, and L. F. Lemanski. (2008). "A novel protein involved in the heart development in *Ambystoma mexicanum* is localized in endoplasmic reticulum." *Journal of Biomedical Science,* 15, 789-799.

Kochegarov A, Moses A, Lian W, Meyer J, Hanna M C, Lemanski L F. (2013) A new unique form of microRNA from human heart, microRNA-499c, promotes myofibril formation and rescues cardiac development in mutant axolotl embryos. J Biomed Sci 20:1-20.

Lafrance, S M, M E Fransen, N. Erginel-Unaltuna, D K Dube, D R Robertson, C. Stefanu, T K Ray, and LF Lemanski. (1993). "RNA from normal anterior endoderm/mesoderm-conditioned medium stimulates myofibrillogenesis in developing mutant axolotl hearts." Cell Mol Biol Res Vol. 39, Issue 6, 547-560.

Lemanski L F. (1973) Morphology of developing heart in cardiac lethal mutant Mexican axolotls, *Ambystoma mexicanum*. Dev Biol 33: 312-333.

Lemanski L F, Nakatsugawa M, Bhatia R, Erginel-Unaltuna N, Spinner B J, Dube D K. (1996) A specific synthetic RNA promotes cardiac myofibrillogenesis in the Mexican axolotl. Biochem Biophys Res Com 229: 974-981.

Lemanski, L. F., F. Meng, S. L. Lemanski, N. Dawson, C. Zhang, D. Foster, Q. Li, M. Nakatsugawa, R. W. Zajdel, D. K. Dube, and X. Huang. (2001). "Creation of chimeric mutant axolotls: a model to study early embryonic heart development in Mexican axolotls." Anatomy and Embryology, 203, 335-342.

Lemanski L F, Zhang C (2007) Promoting Cardiac Cell Differentiation (US Issued Patent [Sep. 18, 2007] 60/462,171).

Lemanski, L. F., C. Zhang, A. Kochegarov, A. Moses, W. Lian, J. Meyer, P. Jia, Y. Jia, K. A. Webster, X. Huang, M. Hanna, M. P. Achary, S. L. Lemanski, and H. Weissbach 2012 Protection of mouse embryonic stem cells from oxidative stress by methionine sulfoxide reductases. In: Oxidative Stress: Molecular Mechanisms and Biological Effects (Eds. V. I. Lushchak and H. M. Semchyshyn, InTech, Rijeka, Croatia) pp. 197-230.

Luis Zambrano, Paola Mosig Reidl, Jeanne McKay, Richard Griffiths, Brad Shaffer, Oscar Flores-Villela, Gabriela Parra-Olea, David Wake. (2010). *Ambystoma mexicanum*. In: IUCN 2011. IUCN Red List of Threatened Species. Version 2011.2. <www.iucnredlist.org>. Downloaded on 9 Jan. 2012.

Kochegarov, A., A. Moses, W. Lian, M. C. Hanna and L. F. Lemanski 2013 A new unique form of microRNA from human heart, microRNA-499c, promotes myofibril formation and rescues cardiac development in mutant axolotl embryos. J. Biomed. Sci., 20(1): 20.

Moses-Arms, A., A. Kochegarov, J. Arms, S. Burlbaw, W. Lian, J. Meyer, L. F. Lemanski. 2014. Identification of a human mitochondrial RNA that promotes tropomyosin synthesis and myocardial differentiation. Invitro Cell Dev Biol, In Press.

Mummery C L, van Achterberg T A, van den Eijnden-van Raaij A J, van Haaster L, Willemse A, de Laat S W, Piersma A H. Visceral-endoderm-like cell lines induce differentiation of murine P19 embryonal carcinoma cells. Differentiation. 1991 February; 46(1):51-60.

Mummery C, Ward D, van den Brink C E, Bird S D, Doevendans P A, Opthof T, Brutel de la Riviere A, Tertoolen L, van der Heyden M, Pera M. Cardiomyocyte differentiation of mouse and human embryonic stem cells. J Anat. 2002 March; 200(Pt 3):233-42. Parker, Steven. (2012). "Cardiovascular disease: the facts." Health Guidance. Retrieved May 8, 2012, from http://www.healthguidance.org/entry/6324/1/Cardiovascular-Disease-The-Facts.html Rueda-de-León E, Kochegarov A, Lian W, Athauda G, Zhang C, Maier J, Huang X, Achary M P, Moses A, Meyer J, Arms J D, Burlbaw S R, Lemanski S L, Lemanski L F. (2011) Human heart RNA promotes tropomyosin synthesis and myofibrillogenesis in mutant axolotl hearts. MD-Med Data 3: 223-227.

Sehnert A J, Huq A, Weinstein B M, Walker C, Fishman M, Stainier D Y. (2002) Cardiac troponin T is essential in sarcomere assembly and cardiac contractility. Nat Genet 31: 106-110.

Sferrazza, G. F., C. Zhang, P. Jia, S. L. Lemanski, G. Athauda, A. Stassi, K. Halager, J. A. Maier, E. Rueda-de-Leon, A. Gupta, S. Dube, X. Huang, H. M. Prentice, D. K. Dube and L. F. Lemanski 2007 Role of myofibril-inducing RNA in cardiac TnT expression in developing Mexican axolotl. Biochem Biophys. Res. Com., 357: 32-37.

Zajdel R W, Thurston H, Prayaga S, Dube S, Poiesz B J, Dube D K. (2007) A reduction of tropomyosin limits development of sarcomeric structures in cardiac mutant hearts of the Mexican axolotl. Cardiovasc Toxicol. 7:235-246.

Zhang C, Dube D K, Huang X, Zajdel R W, Bhatia R, Foster D, Lemanski S L, Lemanski L F. (2003) A point mutation in bioactive RNA results in the failure of mutant heart correction in Mexican axolotls. Anat Embryol 206: 495-506.

Zhang, C., K. M. Pietras, G. F. Sferrazza, P. Jia, G. Athauda, E. Rueda-de-Leon, J. A. Maier, D. K. Dube, S. L. Lemanski, and L. F. Lemanski. (2007). "Molecular and immunohistochemical analyses of cardiac troponin T during cardiac development on the Mexican axolotl, *Ambystoma mexicanum*." Journal of Cellular Biochemistry, 100, 1-15.

Zhang C, Jia P, Huang X, Sferrazza G F, Athauda G, Achary M P, Wang J, Lemanski S L, Dube D K, Lemanski L F. (2009) Myofibril-inducing RNA (MIR) is essential for tropomyosin expression and myofibrillogenesis in axolotl hearts. J Biomed Sci 16:81.

Zhang L L, Liu J J, Liu F, Liu W H, Wang Y S, Zhu B, Yu B. (2012) MiR-499 induces cardiac differentiation of rat mesenchymal stem cells through wnt/β-catenin signaling pathway. Biochem Biophys Res Commun 420: 875-881.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for rescuing a congenitally defective heart of an embryonic axolotl, the method comprising: providing an embryonic axolotl comprising a recessive lethal cardiac mutation in gene “c”, wherein said gene “c” mutation causes development of congenitally defective heart; and introducing into the heart of said embryonic axolotl a composition comprising a cardiogenic inducing RNA nucleic acid (CIR); wherein said CIR is selected from the group consisting of CIR 1 and CIR 2; and wherein said introducing of said composition rescues the heart of said embryonic axolotl from developing into said congenitally defective heart.

2. The method of claim 1, wherein the composition is comprised in and expressed by a cell, and said introducing occurs by injection of the cell into said heart of said embryonic axolotl.

3. The method of claim 1, wherein said introducing occurs by direct injection of the composition into the heart of said embryonic axolotl.

* * * * *